(12) United States Patent
Korogi et al.

(10) Patent No.: US 9,895,526 B2
(45) Date of Patent: Feb. 20, 2018

(54) ANTI-CONTAMINATION COVER FOR FLUID CONNECTIONS

(75) Inventors: Todd M. Korogi, Raleigh, NC (US); Theodore J. Mosler, Raleigh, NC (US); Scott P. Jarnagin, Seattle, WA (US); Bryan Peters, Raleigh, NC (US); David L. Foshee, Apex, NC (US); Nathan R. Snell, Wake Forest, NC (US); Andrew Corson, Apex, NC (US)

(73) Assignee: IVAXIS, LLC, Morrisville, NC (US)

( * ) Notice: Subject to any disclaimer, the term of this patent is extended or adjusted under 35 U.S.C. 154(b) by 180 days.

(21) Appl. No.: 12/205,480

(22) Filed: Sep. 5, 2008

(65) Prior Publication Data
US 2010/0292673 A1    Nov. 18, 2010

Related U.S. Application Data

(63) Continuation-in-part of application No. PCT/US2007/063534, filed on Mar. 8, 2007.

(60) Provisional application No. 60/890,186, filed on Feb. 15, 2007, provisional application No. 60/780,426, filed on Mar. 8, 2006, provisional application No.
(Continued)

(51) Int. Cl.
| | |
|---|---|
| *A61M 25/16* | (2006.01) |
| *A61M 39/20* | (2006.01) |
| *A61M 39/16* | (2006.01) |
| A61M 39/04 | (2006.01) |
| A61M 39/26 | (2006.01) |

(52) U.S. Cl.
CPC .......... *A61M 39/20* (2013.01); *A61M 39/165* (2013.01); *A61M 39/04* (2013.01); *A61M 39/26* (2013.01); *Y10T 29/49826* (2015.01)

(58) Field of Classification Search
CPC .................. A61M 39/26; A61M 39/20; A61M 2039/267; A61M 39/162; A61M 39/165
USPC ........ 604/533–284, 132–133, 96.01, 164.01, 604/523, 174–180
See application file for complete search history.

(56) References Cited

U.S. PATENT DOCUMENTS

| | | |
|---|---|---|
| 1,744,026 A | 1/1930 | Baltzley |
| 1,841,597 A | 1/1932 | Hammer et al. |

(Continued)

FOREIGN PATENT DOCUMENTS

| | | |
|---|---|---|
| DE | 2164821 A1 | 8/1972 |
| EP | 0462355 A1 | 12/1991 |

(Continued)

OTHER PUBLICATIONS

The International Bureau of WIPO, PCT International Preliminary Report on Patentability and Written Opinion of the International Searching Authority for International Application No. PCT/US2007/063534 dated Nov. 21, 2007.
(Continued)

*Primary Examiner* — Phillip Gray
(74) *Attorney, Agent, or Firm* — Christopher J. Knors; Moore & Van Allen PLLC

(57) ABSTRACT

A fluid connector comprising a housing having an access site, and a cover member passively positioned in an initial covering relationship with the access site, the cover member being reversible from an uncovered relationship under load to the initial covering relationship, is described. A method of preventing contamination and aseptically covering an access site of a fluid connector with a cover member is also described.

16 Claims, 33 Drawing Sheets

Related U.S. Application Data

61/132,188, filed on Jun. 16, 2008, provisional application No. 61/068,092, filed on Mar. 4, 2008, provisional application No. 61/011,572, filed on Jan. 21, 2008, provisional application No. 60/967,640, filed on Sep. 6, 2007.

(56) References Cited

U.S. PATENT DOCUMENTS

| | | |
|---|---|---|
| 1,937,492 A | 11/1933 | Merolle |
| 2,322,701 A | 6/1943 | Nesset et al. |
| 2,341,285 A | 2/1944 | Petrullo |
| 2,731,963 A | 1/1956 | Blank |
| 2,740,480 A | 4/1956 | Cox et al. |
| 2,993,612 A | 7/1961 | Trautvetter |
| 3,052,386 A * | 9/1962 | Martorelli .......... B65D 47/0866 222/517 |
| 3,120,879 A * | 2/1964 | Warner .................. F16N 21/02 184/91 |
| 3,199,748 A * | 8/1965 | Bross .................... B65D 47/10 215/307 |
| 3,362,587 A | 1/1968 | Postel et al. |
| 3,391,847 A | 7/1968 | Christine et al. |
| 3,405,831 A | 10/1968 | Hudson et al. |
| 3,431,548 A | 3/1969 | Busier et al. |
| 3,435,978 A | 4/1969 | Wittwer |
| 3,443,686 A | 5/1969 | Raymond et al. |
| 3,651,972 A | 3/1972 | Itoh |
| 3,771,685 A | 11/1973 | Micallef |
| 3,818,627 A | 6/1974 | Lebensfeld |
| 3,979,001 A | 9/1976 | Bogert |
| 3,987,921 A | 10/1976 | Aichinger |
| 3,987,930 A | 10/1976 | Fuson |
| 4,089,463 A | 5/1978 | Babiol |
| 4,169,751 A | 10/1979 | Yen |
| 4,232,677 A | 11/1980 | Leibinsohn |
| 4,257,526 A | 3/1981 | Weits et al. |
| 4,280,632 A | 7/1981 | Yuhara |
| 4,289,248 A | 9/1981 | Lynn |
| 4,335,756 A | 6/1982 | Sharp et al. |
| 4,340,148 A | 7/1982 | Beckham |
| 4,401,227 A | 8/1983 | Pehr |
| 4,432,764 A | 2/1984 | Lopez |
| 4,440,207 A | 4/1984 | Genatempo et al. |
| 4,461,394 A | 7/1984 | Sendel et al. |
| 4,530,726 A | 7/1985 | Montiel |
| 4,564,116 A | 1/1986 | Prohaska |
| 4,572,373 A | 2/1986 | Johansson |
| 4,597,758 A | 7/1986 | Aalto et al. |
| 4,624,664 A | 11/1986 | Peluso et al. |
| 4,655,762 A | 4/1987 | Rogers |
| 4,671,306 A | 6/1987 | Spector |
| 4,674,643 A | 6/1987 | Wilde et al. |
| 4,712,705 A | 12/1987 | Fuehrer |
| 4,752,983 A | 6/1988 | Grieshaber |
| 4,778,447 A | 10/1988 | Velde et al. |
| 4,798,303 A | 1/1989 | Arnold |
| 4,810,241 A | 3/1989 | Rogers |
| 4,991,629 A | 2/1991 | Ernesto et al. |
| 5,065,783 A | 11/1991 | Ogle, II |
| 5,078,693 A * | 1/1992 | Shine .................. A61M 5/3216 604/192 |
| 5,143,104 A | 9/1992 | Iba et al. |
| 5,169,033 A | 12/1992 | Shay |
| 5,184,742 A | 2/1993 | DeCaprio et al. |
| 5,242,425 A | 9/1993 | White et al. |
| 5,263,606 A | 11/1993 | Dutt et al. |
| 5,277,311 A * | 1/1994 | Hollister .................. 206/365 |
| 5,289,930 A * | 3/1994 | Inouye .................. B65D 83/00 206/223 |
| 5,292,020 A | 3/1994 | Narin |
| 5,385,372 A * | 1/1995 | Utterberg ............. A61M 39/20 215/306 |
| 5,385,378 A | 1/1995 | Hakamada et al. |
| 5,398,837 A | 3/1995 | Degrassi |
| 5,409,471 A | 4/1995 | Atkinson et al. |
| 5,445,270 A | 8/1995 | Dratz |
| 5,535,771 A | 7/1996 | Purdy et al. |
| 5,554,135 A | 9/1996 | Menyhay |
| 5,624,402 A | 4/1997 | Imbert |
| 5,694,978 A | 12/1997 | Hellmann et al. |
| 5,702,017 A | 12/1997 | Goncalves |
| 5,743,884 A * | 4/1998 | Hasson .............. A61B 17/3462 137/247.17 |
| 5,743,894 A | 4/1998 | Swisher |
| 5,792,120 A | 8/1998 | Menyhay |
| 5,807,345 A | 9/1998 | Grabenkort |
| 5,807,347 A | 9/1998 | Bonaldo |
| 5,947,954 A | 9/1999 | Bonaldo |
| 5,951,519 A | 9/1999 | Utterberg |
| 5,954,957 A | 9/1999 | Chin-Loy et al. |
| 5,989,227 A | 11/1999 | Vetter et al. |
| 6,004,299 A | 12/1999 | Arai et al. |
| 6,027,482 A | 2/2000 | Imbert |
| 6,036,672 A | 3/2000 | Allen et al. |
| 6,045,539 A * | 4/2000 | Menyhay ............. A61M 39/162 138/89 |
| 6,102,223 A | 8/2000 | Montgomery |
| 6,116,468 A | 9/2000 | Nilson |
| 6,190,364 B1 | 2/2001 | Imbert |
| 6,196,998 B1 | 3/2001 | Jansen et al. |
| 6,227,391 B1 | 5/2001 | King |
| 6,250,315 B1 | 6/2001 | Ernster |
| 6,293,293 B1 | 9/2001 | Wrigley et al. |
| 6,299,131 B1 | 10/2001 | Ryan |
| 6,364,862 B1 | 4/2002 | Bonilla |
| 6,394,983 B1 | 5/2002 | Mayoral et al. |
| 6,520,935 B1 | 2/2003 | Jansen et al. |
| 6,523,686 B1 | 2/2003 | Bae |
| 6,524,295 B2 | 2/2003 | Daubert et al. |
| 6,527,751 B2 | 3/2003 | Fischer et al. |
| 6,622,882 B2 * | 9/2003 | Smith .................. B01L 3/50825 215/253 |
| 6,821,267 B2 | 11/2004 | Veillon, Jr. et al. |
| 6,880,801 B2 | 4/2005 | Matkovich et al. |
| 6,911,025 B2 | 6/2005 | Miyahara |
| 6,913,157 B2 | 7/2005 | Oh |
| 7,083,605 B2 | 8/2006 | Miyahara |
| 7,090,191 B2 | 8/2006 | Matkovich et al. |
| 7,118,560 B2 | 10/2006 | Bonaldo |
| 7,188,623 B2 * | 3/2007 | Anderson et al. ....... 128/207.16 |
| 7,198,611 B2 | 4/2007 | Connell et al. |
| 7,282,186 B2 | 10/2007 | Lake, Jr. et al. |
| 7,316,669 B2 | 1/2008 | Ranalletta |
| 7,329,235 B2 | 2/2008 | Bertron et al. |
| 7,329,249 B2 | 2/2008 | Bonaldo |
| 7,427,275 B2 | 9/2008 | DeRuntz et al. |
| 7,452,349 B2 | 11/2008 | Miyahara |
| 7,500,964 B2 | 3/2009 | Shaw et al. |
| 7,530,977 B2 | 5/2009 | Lodi |
| 7,682,561 B2 | 3/2010 | Davis et al. |
| 7,704,002 B2 | 4/2010 | Fisher et al. |
| 7,780,794 B2 | 8/2010 | Rogers et al. |
| 7,857,793 B2 | 12/2010 | Raulerson et al. |
| 7,922,701 B2 | 4/2011 | Buchman |
| 7,931,618 B2 | 4/2011 | Wyrick |
| 7,931,877 B2 | 4/2011 | Steffens et al. |
| 7,967,779 B2 | 6/2011 | Bertron et al. |
| 7,985,302 B2 | 7/2011 | Rogers et al. |
| 7,988,676 B1 | 8/2011 | Gray |
| 8,061,544 B2 | 11/2011 | Frishman |
| 8,105,293 B2 | 1/2012 | Pickhard |
| 8,162,899 B2 | 4/2012 | Tennican |
| 8,167,847 B2 | 5/2012 | Anderson et al. |
| 8,172,813 B2 | 5/2012 | Janish |
| 8,177,768 B2 | 5/2012 | Leinsing |
| 7,780,794 C1 | 6/2012 | Rogers et al. |
| 8,197,749 B2 | 6/2012 | Howlett et al. |
| 8,206,514 B2 | 6/2012 | Rogers et al. |
| 8,231,587 B2 | 7/2012 | Solomon et al. |
| 8,277,422 B2 | 10/2012 | Oliver et al. |
| 8,287,491 B2 | 10/2012 | Burns et al. |
| 8,296,893 B2 | 10/2012 | Vinci et al. |
| 8,303,548 B2 | 11/2012 | Ito et al. |

(56) References Cited

U.S. PATENT DOCUMENTS

| | | |
|---|---|---|
| 8,641,681 B2 | 2/2014 | Solomon et al. |
| 8,647,326 B2 | 2/2014 | Solomon et al. |
| 8,832,894 B2 | 9/2014 | Rogers et al. |
| 8,834,650 B2 | 9/2014 | Rogers et al. |
| 2001/0003150 A1 | 6/2001 | Imbert |
| 2002/0133124 A1 | 9/2002 | Leinsing et al. |
| 2004/0024357 A1 | 2/2004 | Pelkey et al. |
| 2004/0030321 A1 | 2/2004 | Fangrow, Jr. |
| 2004/0039341 A1 | 2/2004 | Ranalletta |
| 2004/0138626 A1 | 7/2004 | Cote et al. |
| 2004/0171993 A1 | 9/2004 | Bonaldo |
| 2004/0172006 A1 | 9/2004 | Bonaldo |
| 2004/0195136 A1 | 10/2004 | Young et al. |
| 2004/0258560 A1 | 12/2004 | Lake et al. |
| 2005/0124970 A1 | 6/2005 | Kunin et al. |
| 2005/0147524 A1 | 7/2005 | Bousquet |
| 2005/0147525 A1 | 7/2005 | Bousquet |
| 2005/0214185 A1 | 9/2005 | Castaneda |
| 2006/0030827 A1 | 2/2006 | Raulerson et al. |
| 2006/0048313 A1 | 3/2006 | Yamaki |
| 2006/0189961 A1 | 8/2006 | Miyahara |
| 2006/0253103 A1 | 11/2006 | Utterberg et al. |
| 2007/0106205 A1 | 5/2007 | Connell et al. |
| 2007/0106229 A1 | 5/2007 | Wong |
| 2007/0112333 A1 | 5/2007 | Hoang et al. |
| 2007/0156118 A1 | 7/2007 | Ramsey et al. |
| 2007/0176117 A1 | 8/2007 | Redmond et al. |
| 2008/0019889 A1 | 1/2008 | Rogers et al. |
| 2008/0027399 A1 | 1/2008 | Harding et al. |
| 2008/0038167 A1 | 2/2008 | Lynn |
| 2008/0039803 A1 | 2/2008 | Lynn |
| 2008/0086091 A1 | 4/2008 | Anderson et al. |
| 2008/0095680 A1 | 4/2008 | Steffens et al. |
| 2008/0128646 A1 | 6/2008 | Clawson |
| 2008/0132880 A1 | 6/2008 | Buchman |
| 2008/0147047 A1 | 6/2008 | Davis et al. |
| 2008/0177250 A1 | 7/2008 | Howlett et al. |
| 2009/0005759 A1 | 1/2009 | Chelak |
| 2009/0008393 A1 | 1/2009 | Howlett et al. |
| 2009/0028750 A1 | 1/2009 | Ryan |
| 2009/0062766 A1 | 3/2009 | Howlett et al. |
| 2009/0099529 A1 | 4/2009 | Anderson et al. |
| 2009/0137969 A1 | 5/2009 | Colantonio et al. |
| 2009/0149819 A1 | 6/2009 | Chelak |
| 2009/0163876 A1 | 6/2009 | Chebator et al. |
| 2009/0205151 A1 | 8/2009 | Fisher et al. |
| 2010/0000040 A1 | 1/2010 | Shaw et al. |
| 2010/0047123 A1 | 2/2010 | Solomon et al. |
| 2010/0049170 A1 | 2/2010 | Solomon et al. |
| 2010/0050351 A1 | 3/2010 | Colantonio et al. |
| 2010/0172794 A1 | 7/2010 | Ferlic et al. |
| 2010/0174162 A1 | 7/2010 | Gough et al. |
| 2010/0199448 A1 | 8/2010 | Vazales et al. |
| 2010/0312197 A1 | 12/2010 | Sano et al. |
| 2010/0313366 A1 | 12/2010 | Rogers et al. |
| 2011/0213341 A1 | 9/2011 | Solomon et al. |
| 2011/0265825 A1 | 11/2011 | Rogers et al. |
| 2011/0277788 A1 | 11/2011 | Rogers et al. |
| 2012/0039764 A1 | 2/2012 | Solomon et al. |
| 2013/0019421 A1 | 1/2013 | Rogers et al. |
| 2013/0237911 A1 | 9/2013 | Von Schuckmann |
| 2014/0101876 A1 | 4/2014 | Rogers et al. |
| 2014/0228773 A1 | 8/2014 | Burkholz |

FOREIGN PATENT DOCUMENTS

| | | |
|---|---|---|
| EP | 1061000 A2 | 12/2000 |
| EP | 1977714 A1 | 10/2008 |
| EP | 2135626 A1 | 12/2009 |
| JP | 07-047137 | 2/1995 |
| JP | 07-043674 | 9/1995 |
| JP | 09-206370 A | 8/1997 |
| JP | 2001-527441 | 12/2001 |
| JP | 2002-291906 A | 10/2002 |
| JP | 4234777 B1 | 3/2009 |
| WO | WO-94/11474 A1 | 5/1994 |
| WO | 98/48872 A1 | 11/1998 |
| WO | WO-00/24442 A1 | 5/2000 |
| WO | 2007/103998 A2 | 9/2007 |
| WO | WO-2007/137056 A2 | 11/2007 |
| WO | WO-2008/100950 A2 | 8/2008 |
| WO | WO-2009/136957 A1 | 11/2009 |
| WO | WO-2009/153224 A1 | 12/2009 |
| WO | WO-2011/056221 A1 | 5/2011 |
| WO | WO-2011/120017 A1 | 9/2011 |

OTHER PUBLICATIONS

Japanese Patent Office, Japanese Notice of Reasons for Rejection for Japanese Patent Application No. 2008-558527 dated Apr. 12, 2012.

European Patent Office, Supplementary Partial European Search Report and Opinion for EP Application No. 07 75 8117 date of completion of the search Nov. 22, 2012, 6 pgs.

U.S. Appl. No. 60/815,806, filed Jun. 22, 2006, Anderson et al.

U.S. Appl. No. 60/832,437, filed Jul. 21, 2006, Rogers.

Byington "Spontaneously Generating Life in Your Classroom? Pasteur, Spallanzani & Science Process," *The American Biology Teacher*, vol. 63, No. 5 (May 2001). pp. 340-345. Published by University of California Press on behalf of National Association of Biology Teachers.

International Search Report and Written Opinion dated Jul. 22, 2009, PCT/US2008/053744.

International Search Report and Written Opinion dated Nov. 9, 2012, PCT/US2012/025517.

International Standard ISO 594-2. "Conical Fitting with 6% (Luer) Taper for Syringes, Needles and Certain Other Medical Equipment—Part 2: Lock Fittings". Reference No. ISO 594-2:1998(E). Second edition. (Sep. 1, 1998)1:11.

Japanese Patent Office, Japanese Notice of Reasons for Rejection for Japanese Patent Application No. 2008-558527 dated Apr. 2, 2013.

Material Properties of Polyamide (Nylon), www.madeitfrom.com, pp. 1-2. Retrieved Sep. 23, 2012.

Material Properties of Polycarbonate, www.madeitfrom.com, pp. 1-3. Retrieved Sep. 23, 2012.

Material Properties of Polypropylene, www.madeitfrom.com, pp. 1-2. Retrieved Sep. 23, 2012.

Menyhay et al. "Disinfection of Needleless Catheter Connectors and Access Ports with Alcohol May Not Prevent Microbial Entry: The Promise of a Novel Antiseptic-Barrier Cap". *The University of Chicago Press on behalf of the Society for Healthcare Epidemiology of America. Infect Control Hosp Epidemiol* vol. 27(2006):23-27.

Menyhay Healthcare Systems LLC available at http://www.menyhaymedical.comimenyhay.html (retrieved Nov. 8, 2013).

PCT Search Report and Written Opinion dated Oct. 16, 2013 for PCT application No. PCT/US2013/044167.

Value Plastics Inc, Luer Connectors, http://www.valueplasctics.com/search/search.aspx, pp. 1-2. Retrieved Sep. 23, 2012.

U.S. Appl. No. 12/791,809, filed Jun. 1, 2010, US 2010-0306938.

U.S. Appl. No. 13/072,653, filed Mar. 25, 2011, US 2011-0232020.

U.S. Appl. No. 13/553,627, filed Jul. 19, 2012, US 2013-0019421.

European Patent Office, European Search Report and Opinion for EP Application No. EP 10 78 3956, date of completion of the search Mar. 12, 2014, 7 pgs.

International Search Report and Written Opinion issued in International Application No. PCT/US2014/026716, dated Jun. 12, 2014.

U.S. Appl. No. 13/099,324, filed May 2, 2011, US 2011-0265825.

U.S. Appl. No. 13/466,976, filed May 8, 2012, US 2012-0216360.

U.S. Appl. No. 13/844,687, filed Mar. 15, 2013, US 2014-0261581.

U.S. Appl. No. 13/910,053, filed Jun. 4, 2013, US 2014-0150832.

U.S. Appl. No. 14/285,526, filed May 22, 2014, US 2014-0261558.

PCT/US2013/044167, Jun. 4, 2013, WO 2013-184716.

PCT/US2014/026716, Mar. 13, 2014, WO 2014-151949.

\* cited by examiner

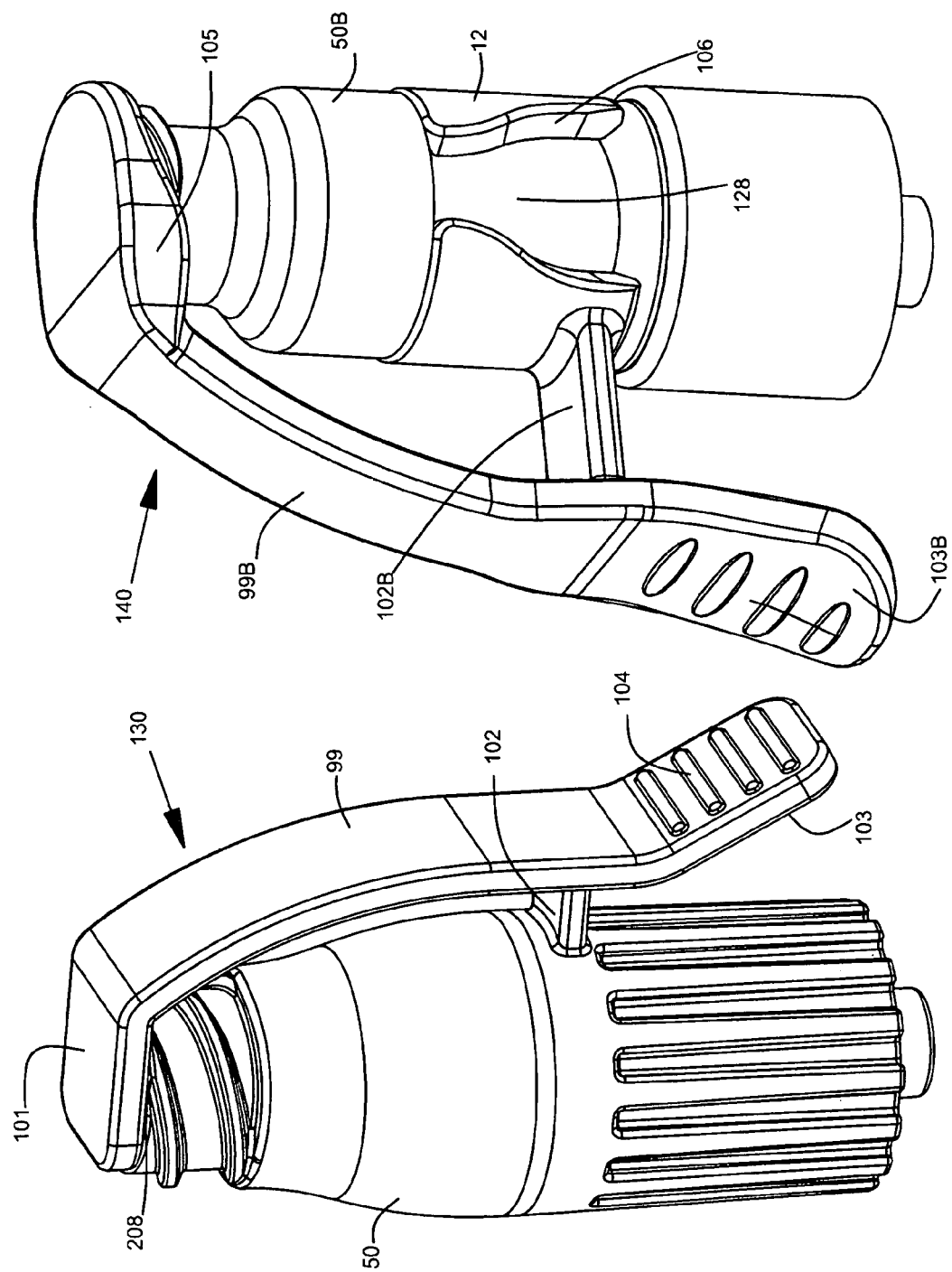

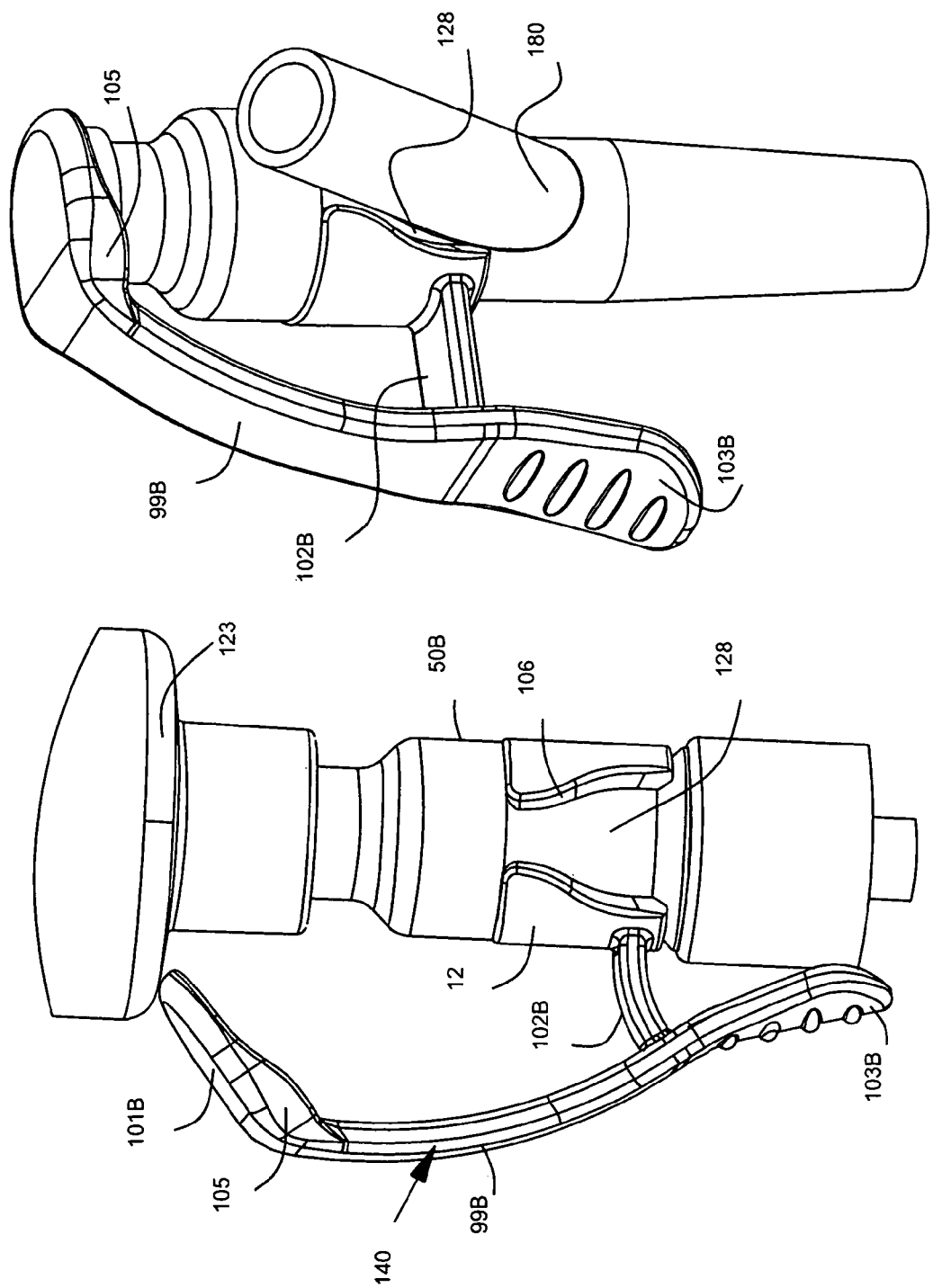

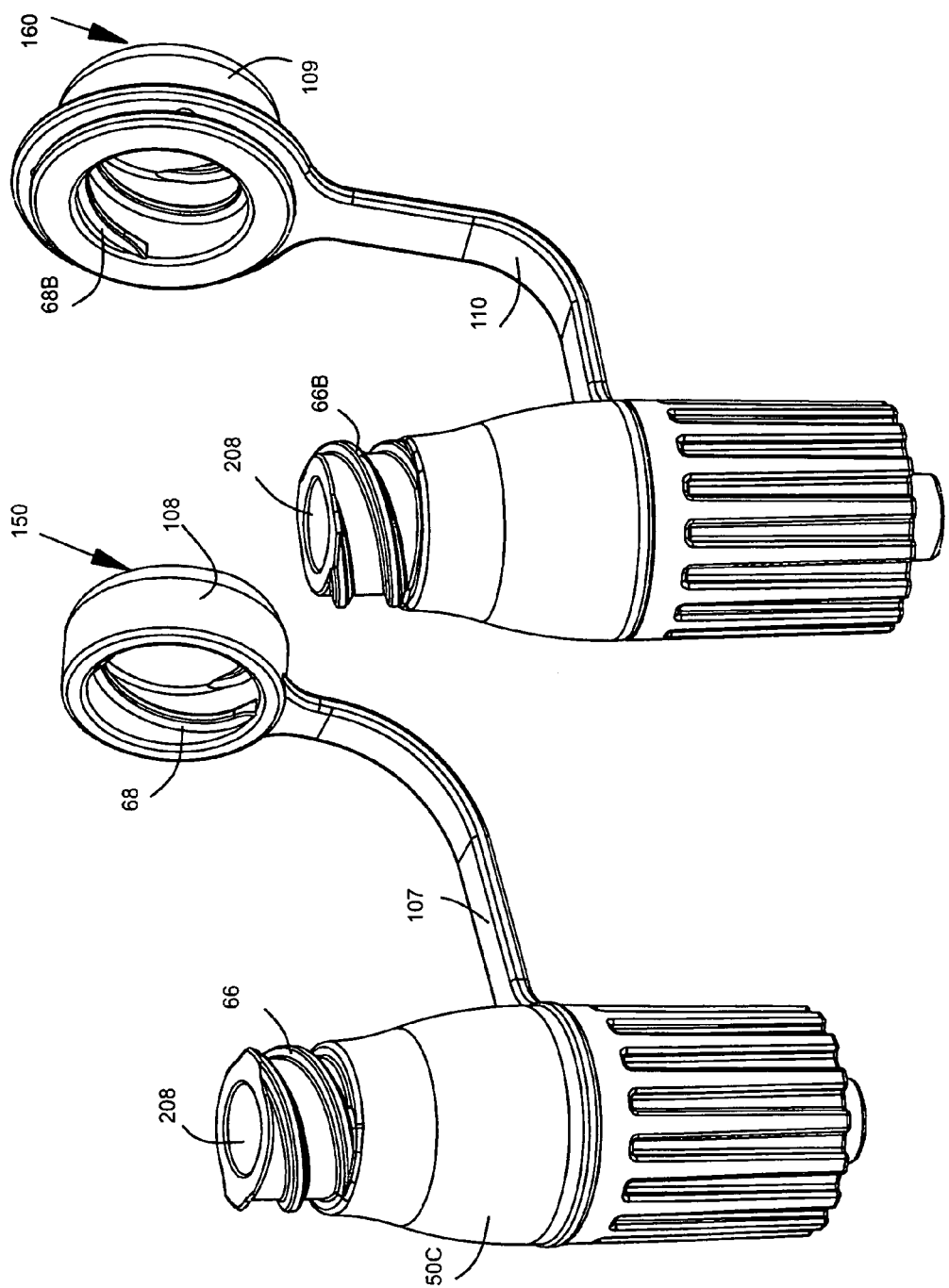

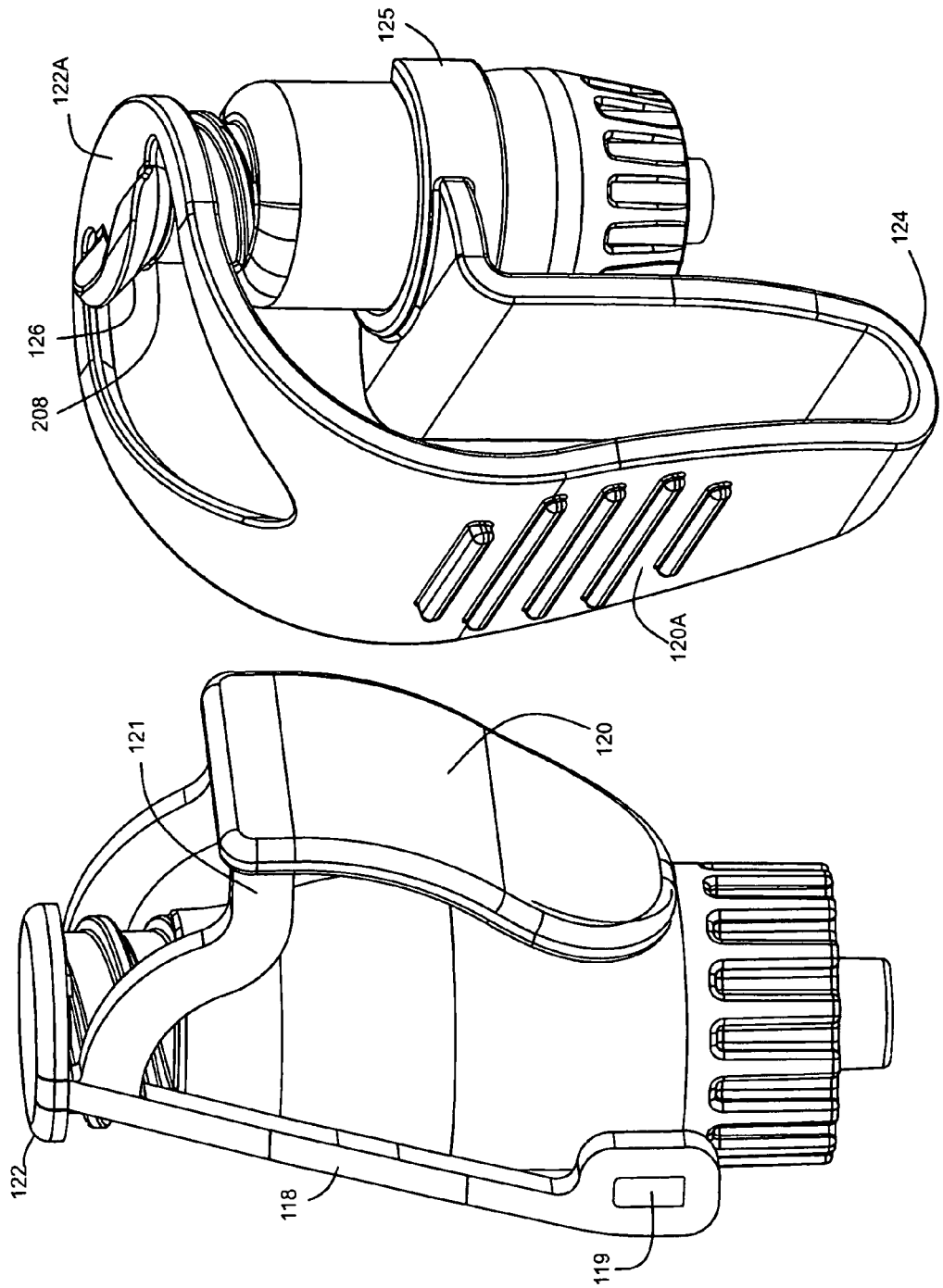

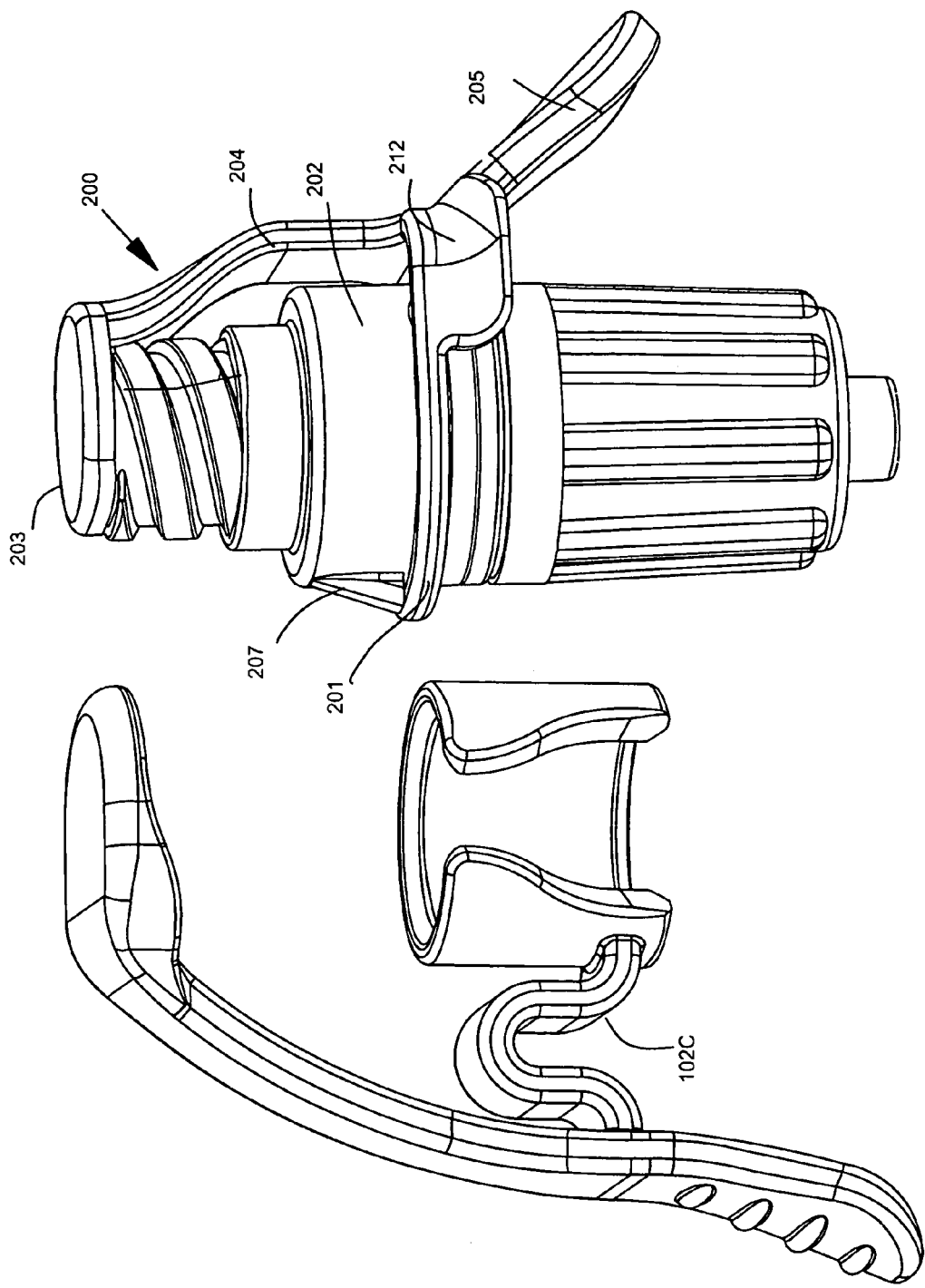

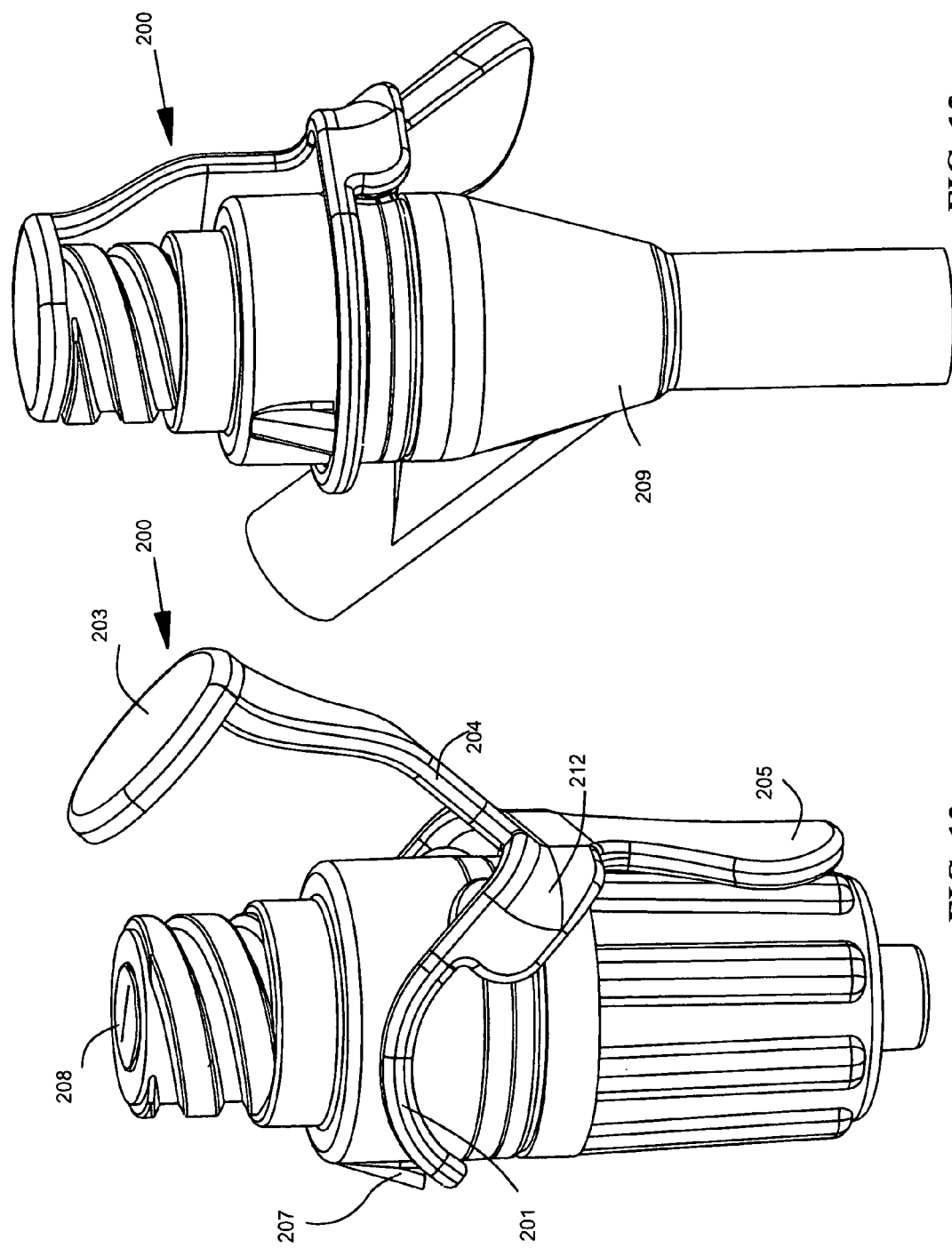

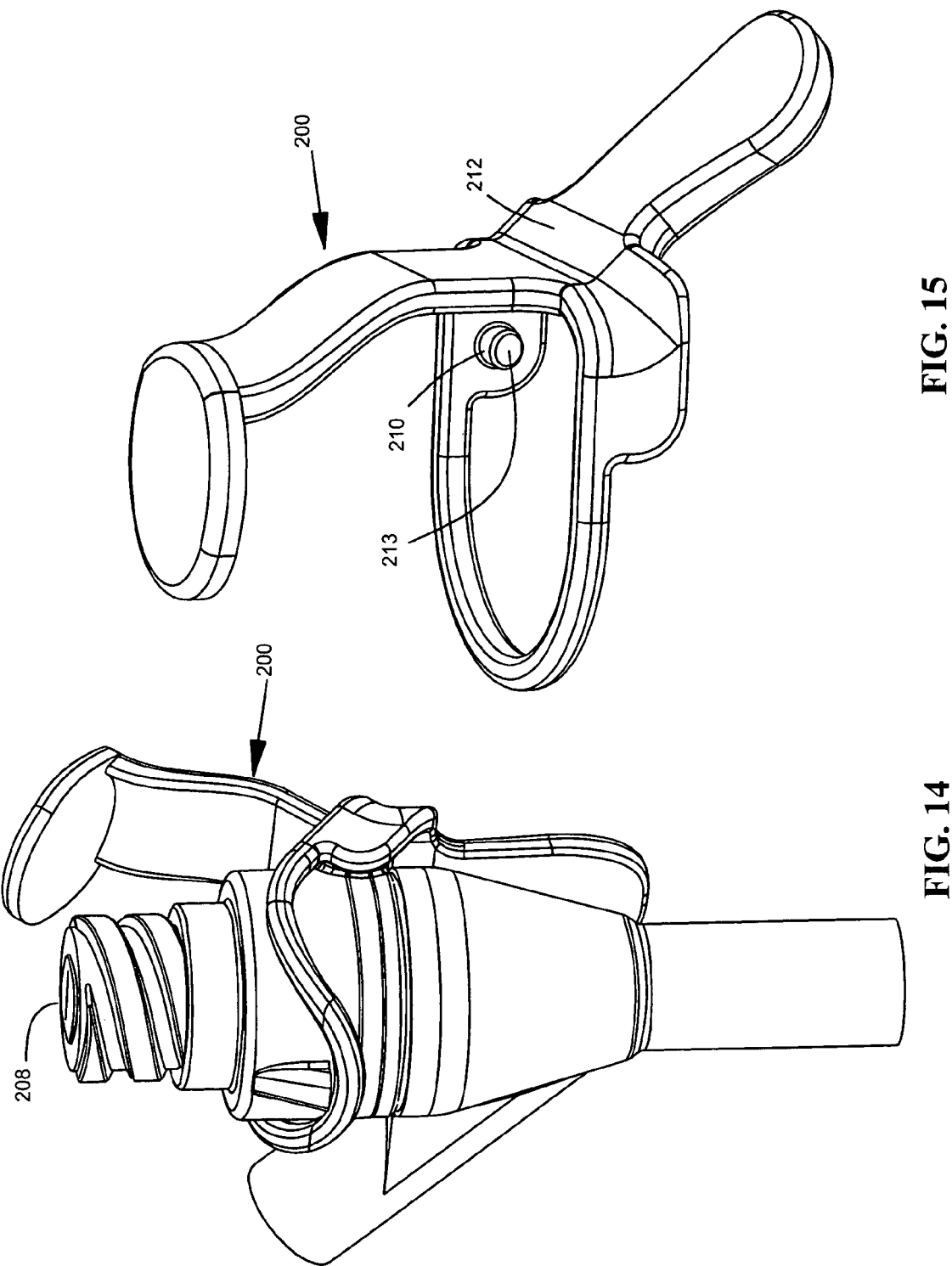

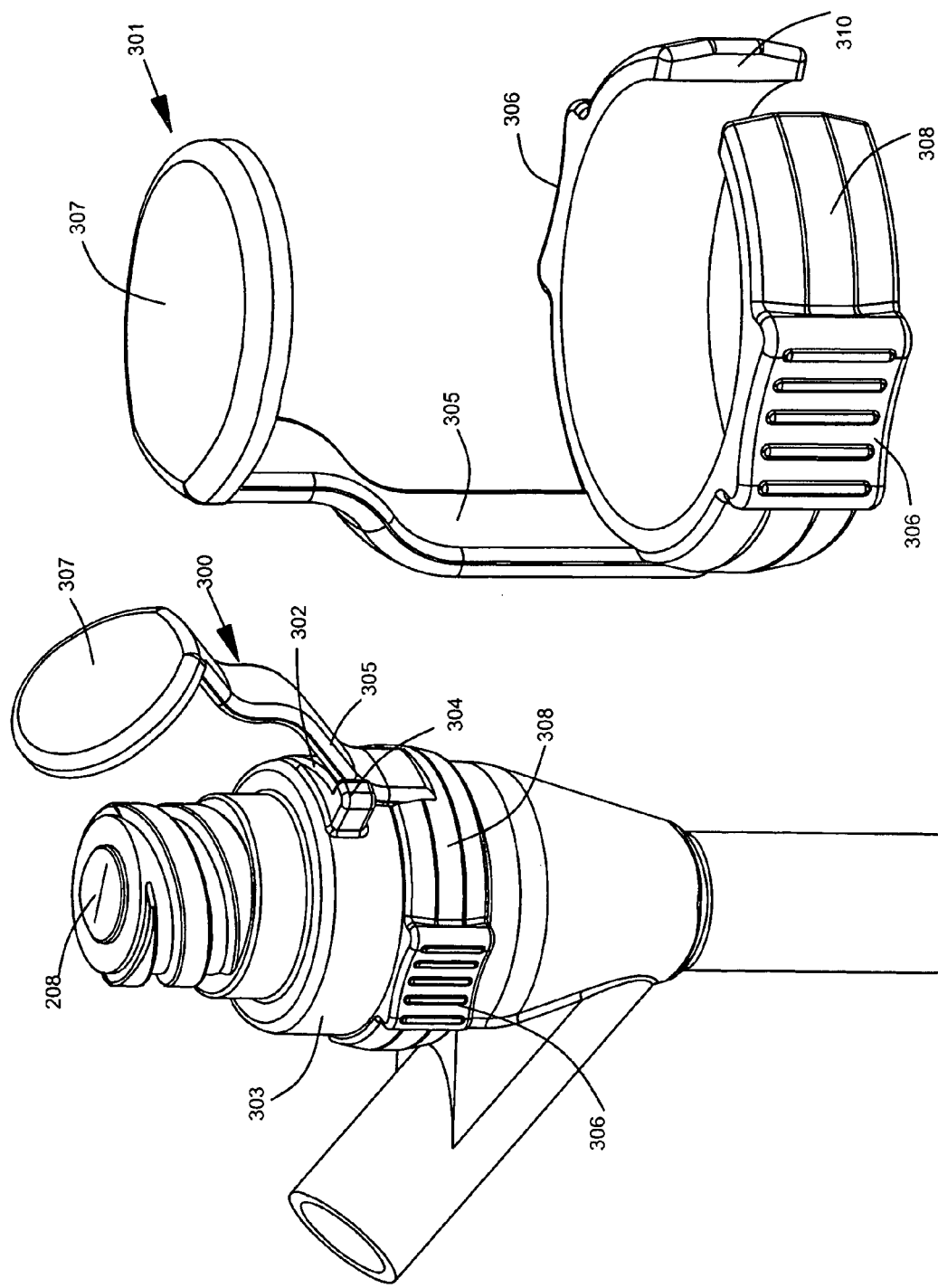

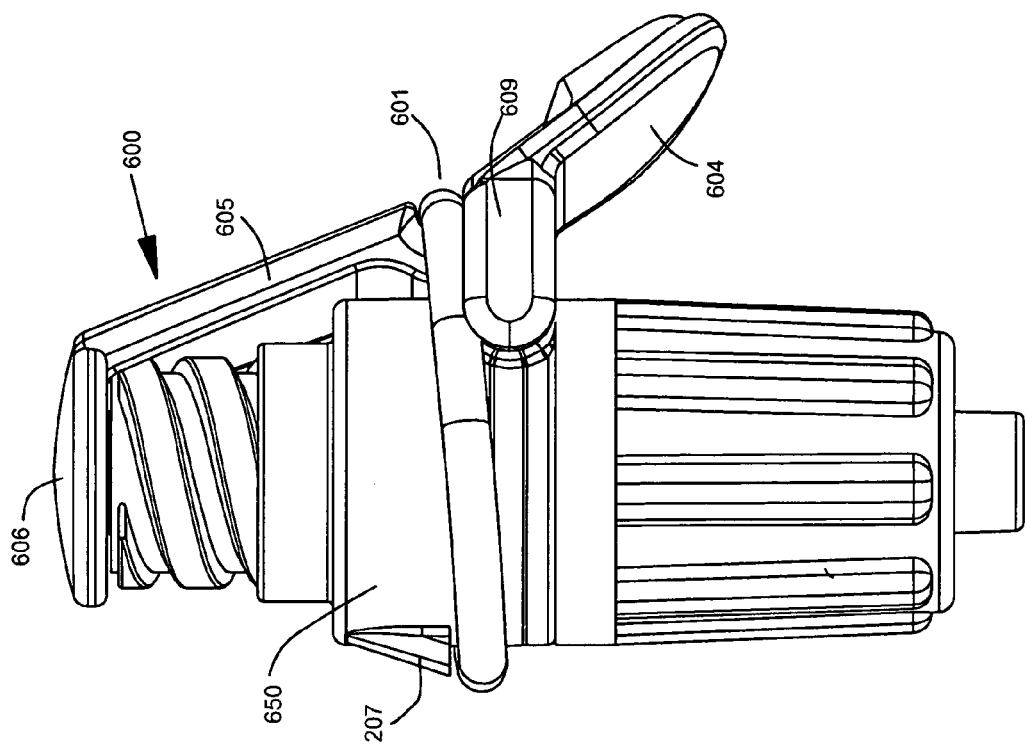
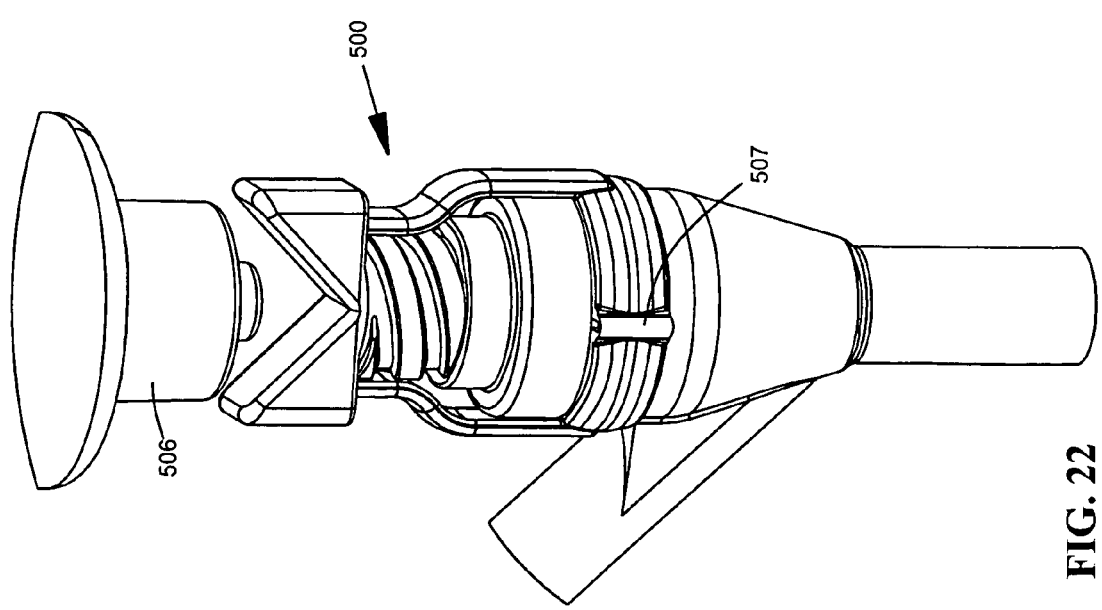
FIG. 23
FIG. 22

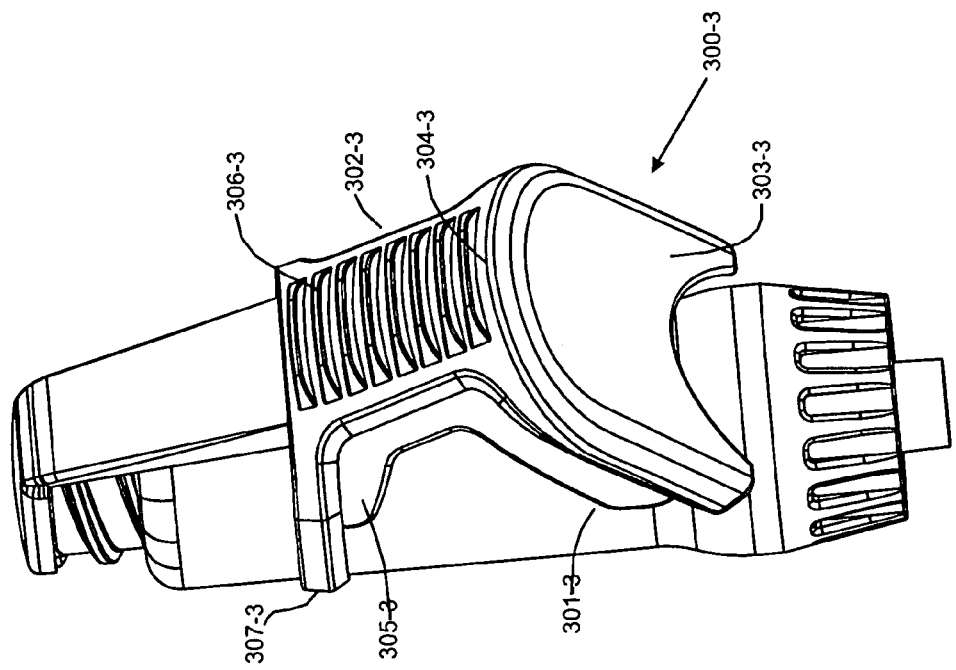
FIG. 39
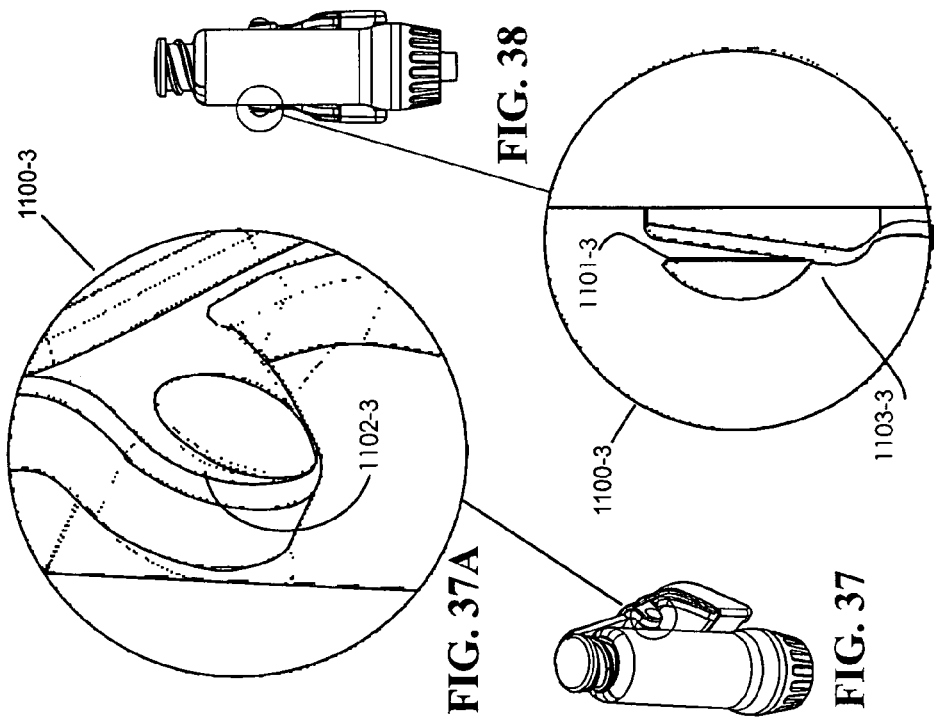
FIG. 37A
FIG. 38A
FIG. 37
FIG. 38

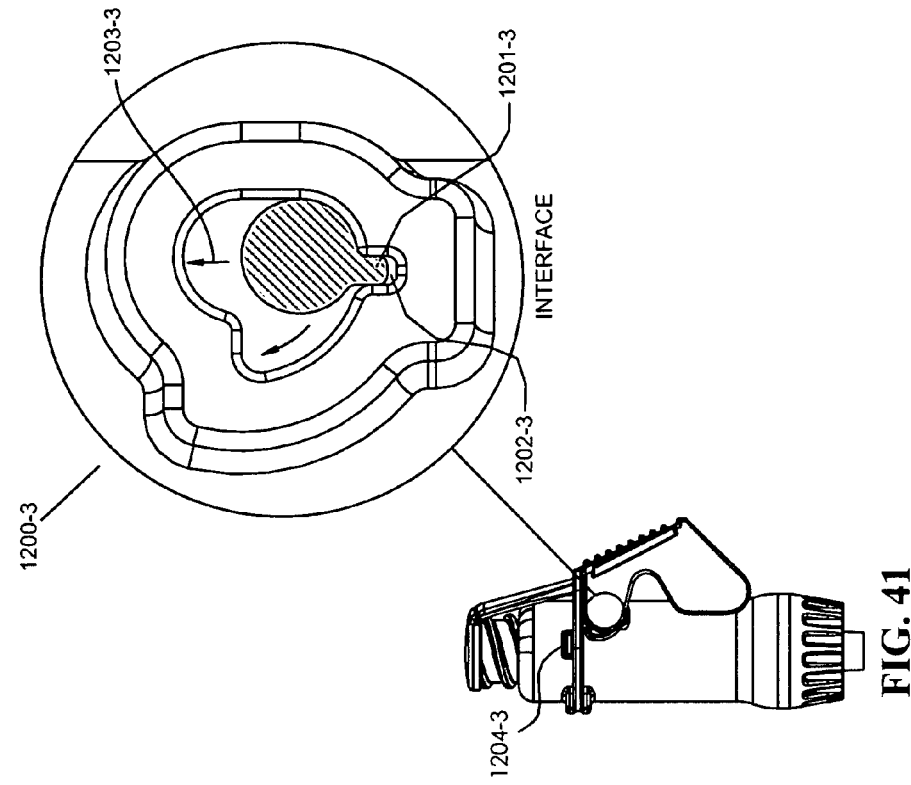
FIG. 41A
FIG. 41
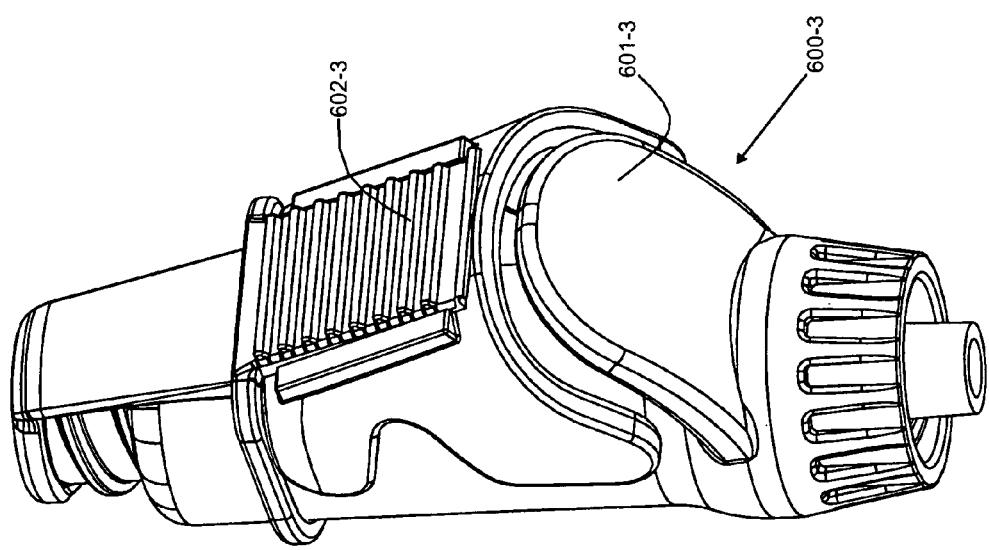
FIG. 40

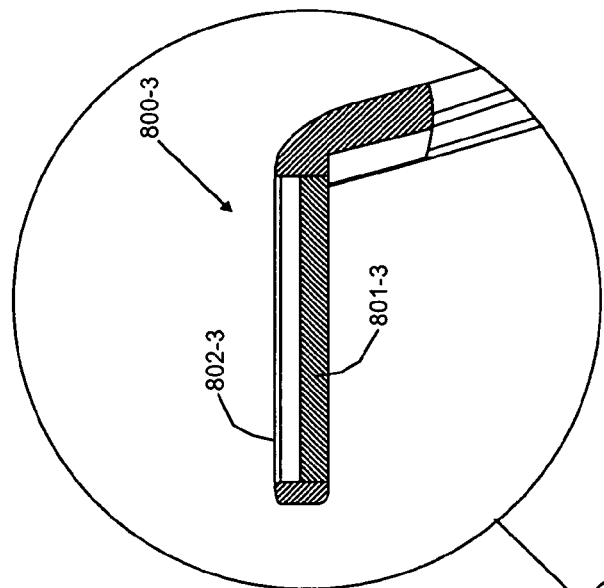
FIG. 43A
FIG. 43
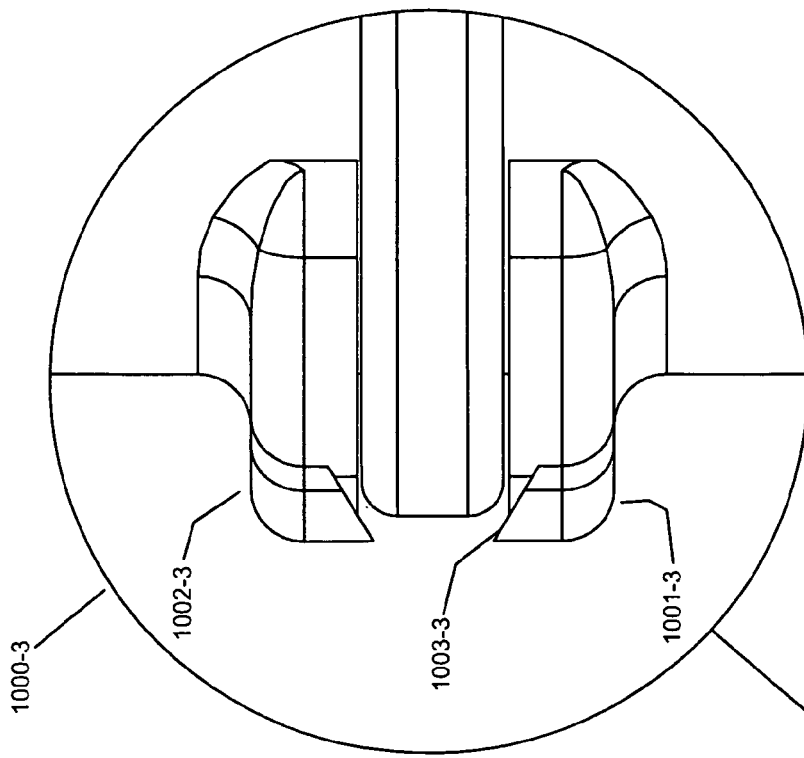
FIG. 42A
FIG. 42

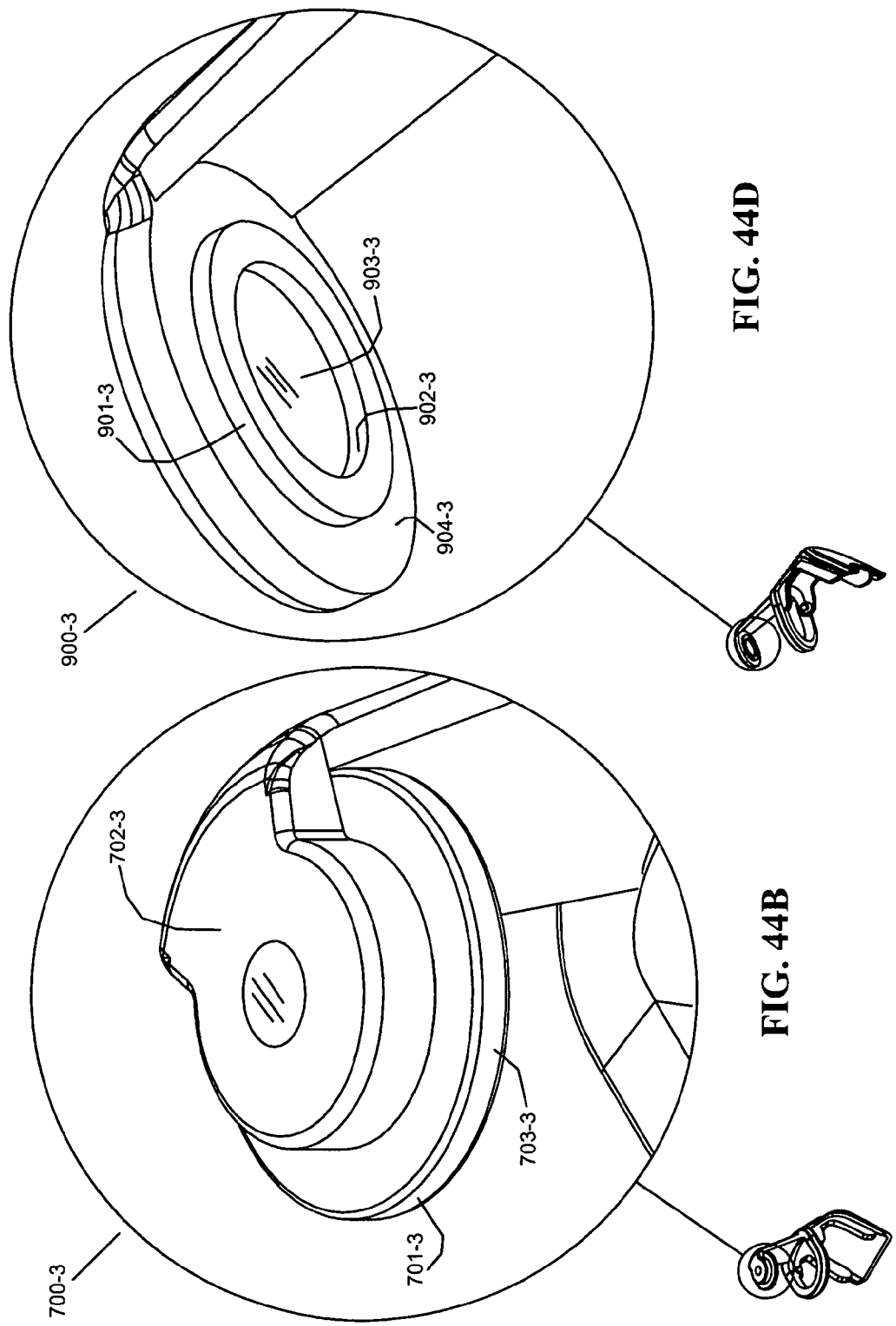

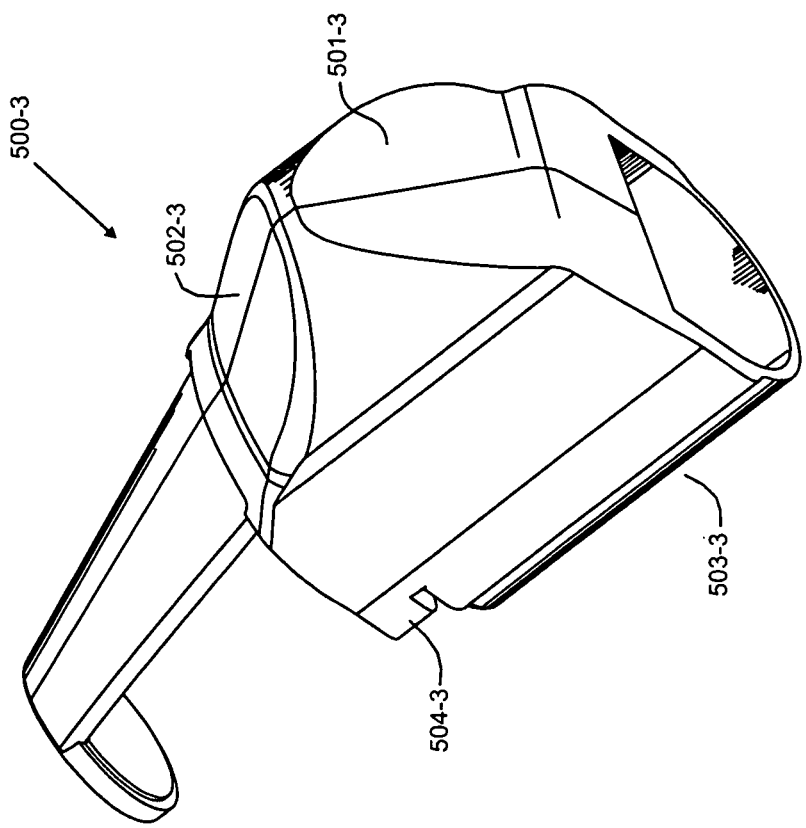
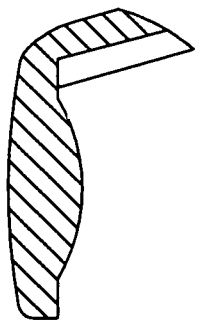
FIG. 45A
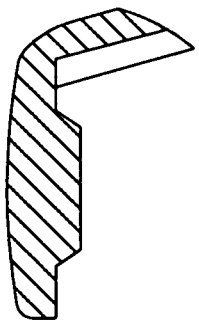
FIG. 45B
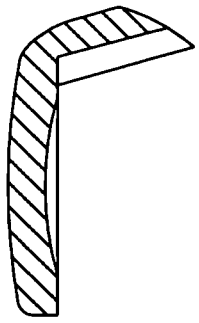
FIG. 45C
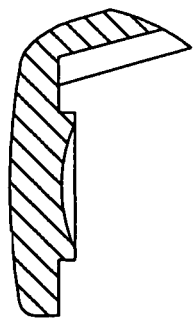
FIG. 45D
FIG. 46

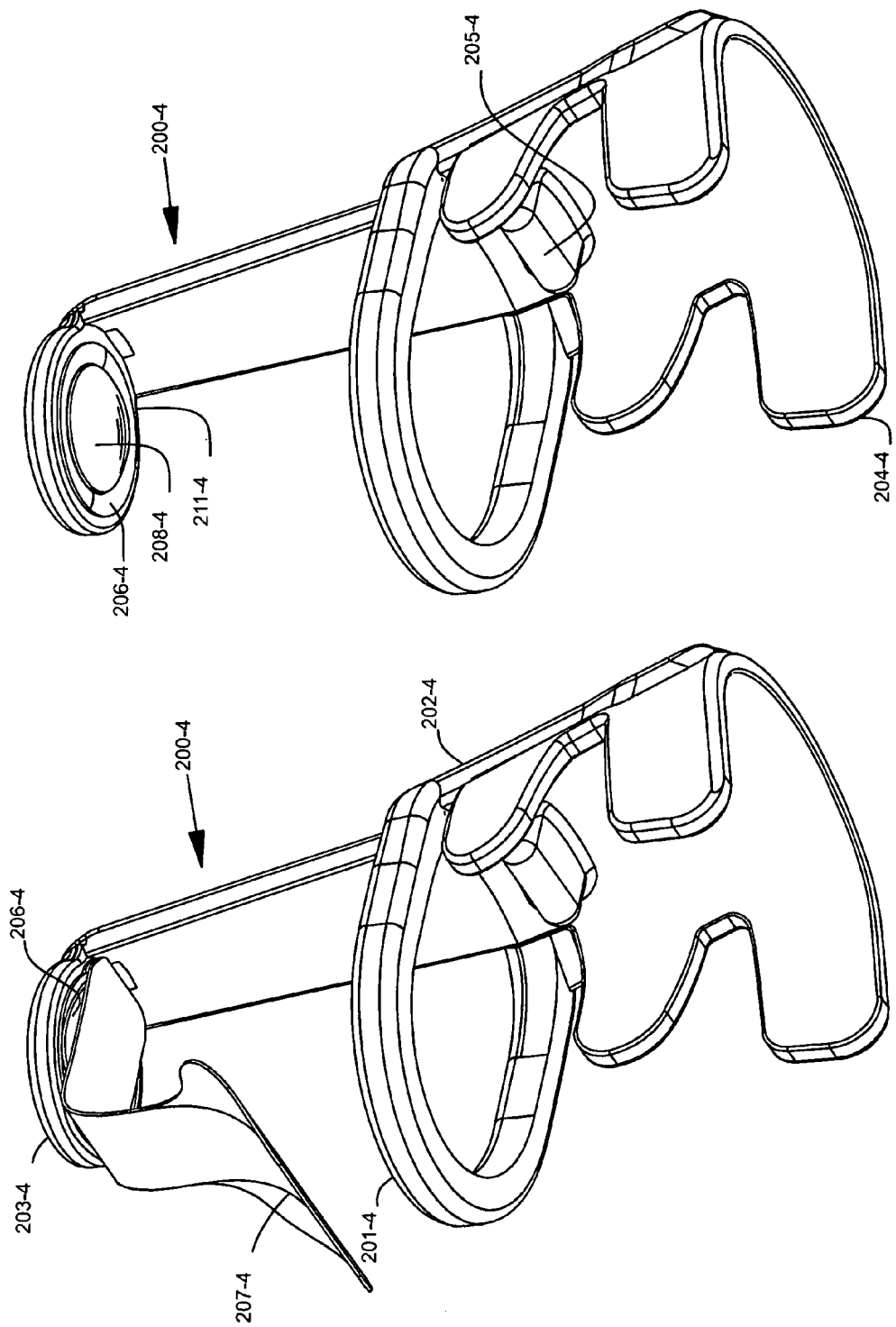

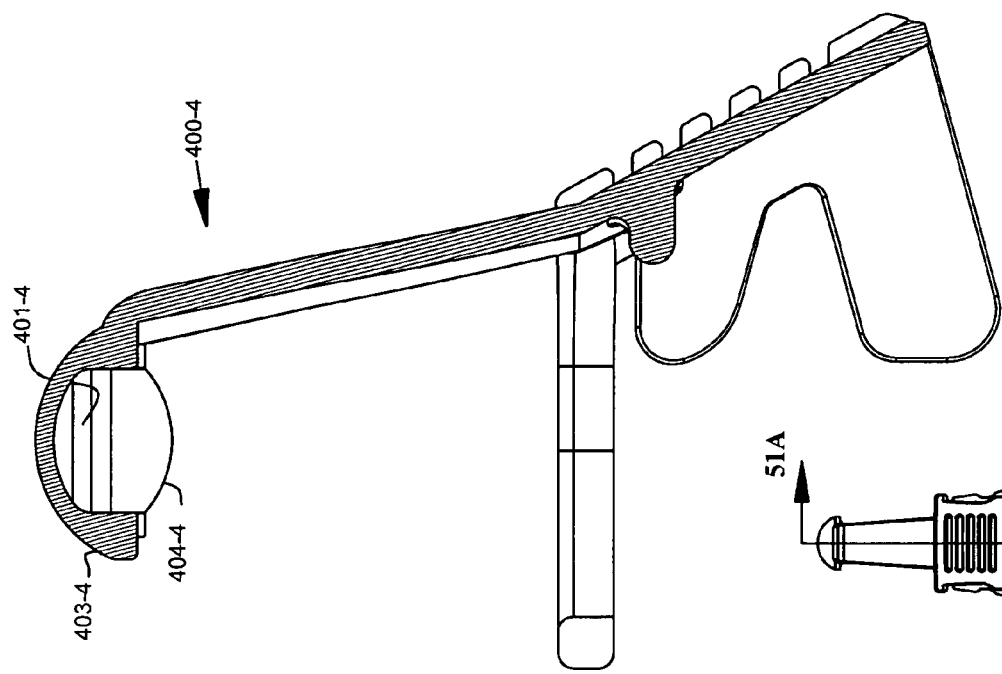
FIG. 51A
FIG. 51
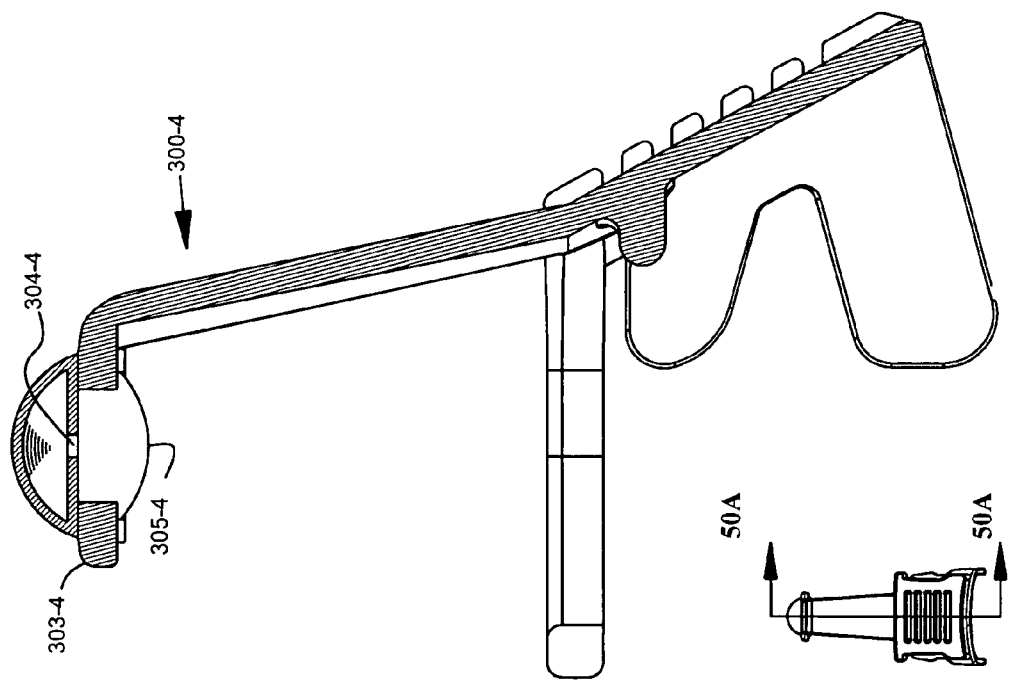
FIG. 50A
FIG. 50

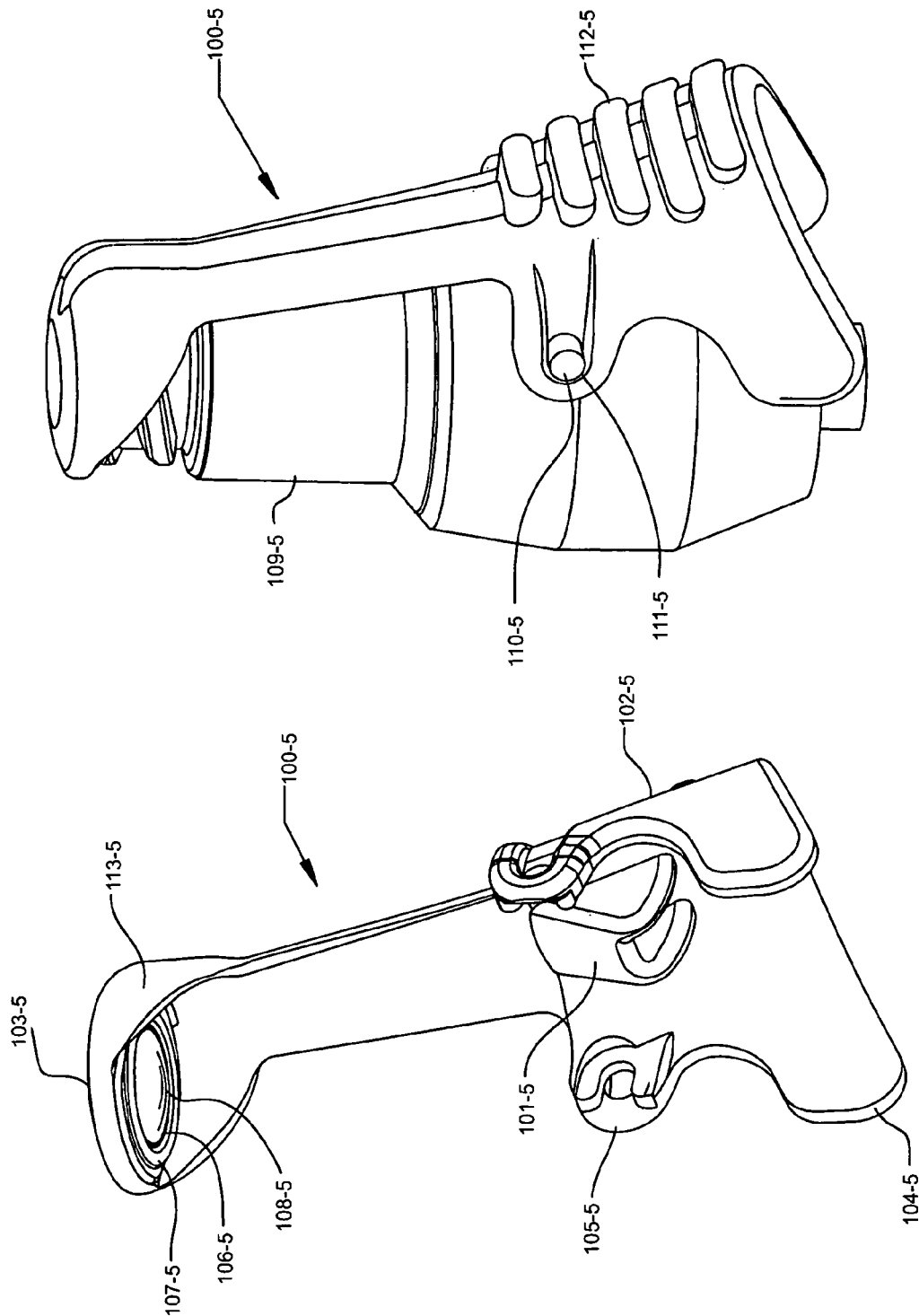

ANTI-CONTAMINATION COVER FOR FLUID CONNECTIONS

CROSS-REFERENCE TO RELATED APPLICATION

This application claims the benefit under 35 U.S.C. 119(e) of U.S. Provisional Application No. 61/132,188, filed Jun. 16, 2008, U.S. Provisional Application No. 61/068,092, filed Mar. 4, 2008, U.S. Provisional Application No. 61/011,572, filed Jan. 21, 2008, U.S. Provisional Application No. 60/967,640, filed Sep. 6, 2007, and is a continuation-in-part of PCT/US2007/063534, filed Mar. 8, 2007, which claims the benefit of U.S. Provisional Application No. 60/780,426, filed Mar. 8, 2006, and U.S. Provisional Application No. 60/890,186, filed Feb. 15, 2007, the entire disclosures of which are incorporated herein by reference in their entirety.

TECHNICAL FIELD

This invention relates to fluid connector covers adaptable to fluid connectors and more particularly to passively activated fluid connector covers. The covers may be impregnated or contain an aseptically effective agent to eliminate or reduce contamination of an access site of the fluid connector.

BACKGROUND

Existing fluid connectors are typically designed without a covering for protecting the access site while it is not in use. Some access sites include screw threads which allow them to more easily be connected to IV tubing during lengthy accesses. However, most external fluid connectors normally remain uncovered and completely exposed with little or no barrier to potential contaminants. Contaminants may include, but are not limited to, germs, bacteria, air, dirt, clothing, skin and perspiration.

Because of the exposure of the fluid connector and access site to contaminants, the use of an aseptic cleansing procedure is typically required prior to accessing the site. Using currently accepted techniques, the cleansing process alone involves several steps and the use of numerous materials for each port access. In order to assure an aseptic environment, a second person may be needed to assist the first with the cleansing process. The clinician may not disinfect the access site for various reasons, including forgetting to do so, not having the appropriate disinfectant swab readily available, being in a hurry, not understanding the importance or a combination of these issues.

When access to the fluid connector is complete, it will again come into contact with the patient's skin or clothing and immediately become susceptible to contamination, requiring repetition of the above procedure the next time the access site is accessed. The cleansing procedure, even if properly followed, is very time consuming. Materials must be gathered prior to access, and an assistant may be required before the procedure can be started. The more frequent the access, the greater the risk of subsequent contamination.

Recent scientific studies suggest that the external access site of a fluid connector may be the place of origin of bacteria infecting the fluid connector. These studies recommend that manipulation of the access site be kept at a minimum, and that a more rigorous approach to aseptic technique be undertaken such as the time consuming, expensive and difficult measures as discuss above. While studies have suggested that the hub of catheter devices be properly covered, such studies fail to propose any cover design apart from indicating covers are needed to protect against contamination.

While external injection port covers directed to maintaining sterility of catheter hubs have been disclosed, these external injection port cover designs require that the cover include threaded elements to securely cover the corresponding threaded elements of the fluid connector. Thus, the cover requires manual manipulation for removal and replacement thereof on the fluid connector and may require a unique design for each fluid connector. Moreover, the covers are often lost or discarded and not replaced. Minimization of such manipulation, and eliminating loss of the cover, and providing a universal, passive design of an aseptic cover for fluid connectors would improve the compliance and sterility of the fluid connector manipulations.

SUMMARY

To address the aforementioned problems, a fluid connector cover for fluid connectors is herein described, adaptable to or integrated with swabable, luer-activated needle-free valves of various forms (e.g. luer locking adapters, y-sites, vial adapters), as well as pre-slit septums accessible by blunt cannula, and septums accessible by needles. The cover may passively cover the access site of fluid connectors of various shapes and types. The cover may provide anti-contamination material to the access site. After access, the cover is passively re-positioned over the access site to provide a clean and aseptic condition at the access site. The fluid connector cover creates a protective cover over the connector housing access site preventing or eliminating contamination, thus preventing or reducing contamination at the injection site of infusion devices. The fluid connector cover operates essentially passively, using pre-loaded return means allowing the cover to return to the connector housing access site immediately upon disconnect of objects accessing the connector housing. This return force also creates a preload condition where the access site will remain covered and/or sealed while not being accessed.

In one aspect, a fluid connector comprising a housing having an access site, and a cover member passively positioned in an initial covering relationship with the access site, the cover member being reversible from an uncovered relationship under load to the initial covering relationship, is described.

In another aspect, a fluid connector comprising a housing having an access site, a rigid arm with a proximal and distal end, a flexible member joining the rigid arm to the housing, and a cover member integral with the distal end of the rigid arm and positioned to cover the access site, is described. The cover member is reversibly displaceable from an initial position covering access site to a second position uncovering the access site upon displacement of the rigid arm.

In another aspect, a cover adapter comprising a cover adapter body securable to a fluid connector having an access site, a rigid arm with a proximal and a distal end, a flexible member joining the rigid arm to the cover adapter body between the proximal and the distal end of the rigid arm, and a cover member integral with the distal end of the rigid arm and positioned to cover the access site of the connector is provided. The cover member is reversibly displaceable from an initial position covering the access site to a second position uncovering the access site upon displacement of the proximal end of the rigid arm In another aspect, a fluid connector comprising a housing comprising at least one fluid access site and attachment members, a rigid arm having a proximal end and a distal end, the rigid arm attached to the housing with corresponding attachment members between the proximal end and the distal end, a flexible member secured to the rigid arm and contacting the fluid connector, is provided. The flexible member provides a load to the rigid arm; and a cover member secured to the distal end of the rigid arm and covering the access site.

In another aspect, a cover adapter comprising a cover adapter body having attachment members securable to a fluid connector, a rigid arm having a proximal end and a distal end, the rigid arm joined to the cover adapter body, a flexible member secured to the cover adapter body or rigid arm and adapted to contact the fluid connector and to provide a load to the rigid arm, is provided. A cover member is secured to the distal end of the rigid arm positioned to cover the access site.

In another aspect, a fluid connector comprising a reservoir is provided in proximity to the cover member. The reservoir comprises an aseptically effective agent. The reservoir may comprise an elastomer, plastic, foam, sponge-like material or any combination thereof adjacent or integral with the cover member. The reservoir may comprise a user-releasable lidding. The lidding may include a tab for assisting removal.

In another aspect, a method of preventing or eliminating contamination of an access site of a fluid connector is provided. The method comprises providing a fluid connector cover comprising a housing, at least one access site, and a rigid member. A cover member is cooperatively connected to the rigid member to provide a covering relationship between the access site and the cover member.

BRIEF DESCRIPTION OF THE FIGURES

FIG. 1 is a perspective view of an embodiment of the fluid connector cover.

FIG. 2A is a perspective view of an embodiment of the fluid connector cover.

FIG. 2B is a perspective view of the embodiment of FIG. 2A with external device engaged.

FIG. 3 is a perspective view of an embodiment of the fluid connector cover on a y-body connector.

FIG. 4 is a perspective view of an embodiment of the fluid connector cover.

FIG. 5 is a perspective view of an embodiment of the fluid connector cover.

FIG. 8 is a perspective view of an embodiment of the fluid connector cover.

FIG. 9 is a perspective view of an embodiment of the fluid connector cover.

FIG. 10 is a perspective view of an embodiment of a cover adapter.

FIG. 11 is a perspective view of an embodiment of the fluid connector cover.

FIG. 12 is a perspective view of an embodiment of the fluid connector cover of FIG. 11 in an activated state.

FIG. 13 is a perspective view of an embodiment of the fluid connector cover on a y-body connector.

FIG. 14 is a perspective view of the embodiment of FIG. 13 in an activated state.

FIG. 15 is a perspective view of an embodiment of a cover adapter.

FIG. 18 is a perspective view of the embodiment of the fluid connector cover of FIG. 17 in an activated state.

FIG. 19 is a perspective view of an embodiment of a cover adapter.

FIG. 22 is a perspective view of the embodiment of FIG. 21 prior to engaging an external device.

FIG. 23 is a perspective view of an embodiment of the fluid connector cover.

FIGS. 37, 37A, 38 and 38A are profile and exploded views, respectively, of attachment means for securing a cover adapter to a connector housing.

FIG. 39 is a perspective view of a cover adapter embodiment assembled with a connector housing.

FIG. 40 is a perspective view of an anti-snag embodiment of a cover adapter.

FIGS. 41 and 41A are profile and exploded views, respectively, of locking means for a cover adapter connected to a connector housing in an initial position.

FIGS. 42 and 42A are profile and exploded views, respectively, of attachment means for securing a flexible member to a connector housing.

FIGS. 43 and 43A are profile and exploded views, respectively, of a cover member embodiment of a cover adapter.

FIGS. 44A-D are profile and exploded views of the top and bottom, respectively, a cover member embodiment of a cover adapter.

FIGS. 45A-D are profile views, respectively, of cover member geometries of a cover adapter.

FIG. 46 is a perspective view of a cover adapter embodiment.

FIGS. 47 and 47A are a perspective view of a cover adapter embodiment with and without user-releasable lidding tab, respectively.

FIGS. 50 and 50A are sectional plane and cross-sectional view, respectively of a cover adapter with reservoir element embodiment.

FIGS. 51 and 51A are sectional plane and cross-sectional view, respectively of a cover adapter with reservoir element embodiment.

FIG. 54 is a perspective view of a first embodiment cover adapter.

FIG. 55 is a perspective view of a cover adapter embodiment secured to a connector housing in a closed, assembled state.

DETAILED DESCRIPTION

Figure 7:
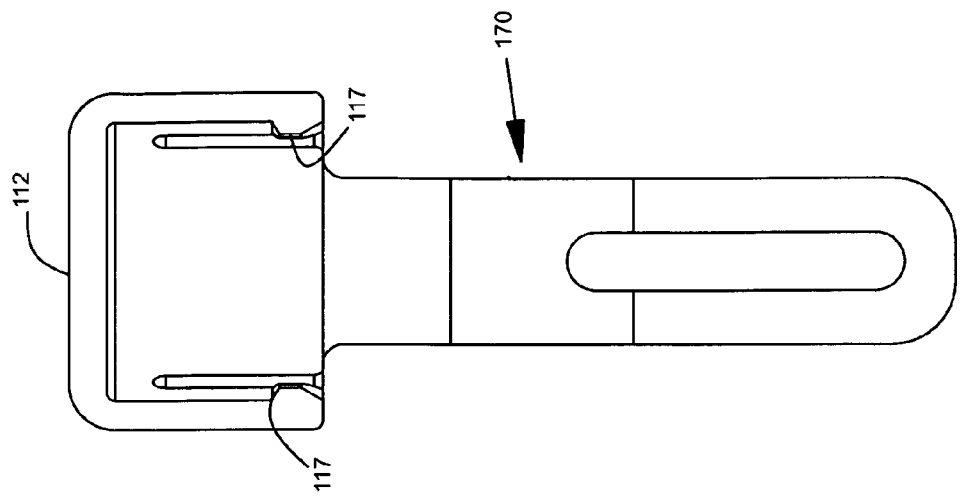
FIG. 7 is a side cross-section view of the cover portion of the embodiment of FIG. 6.

A fluid connector cover for fluid connectors is herein described, which may be adaptable to swabable, leer-activated needle-free valves of various forms e.g. luer locking adapters, y-sites, vial adapters, penetetrable septums accessible by blunt cannula or by needles. The cover passively covers the access site of a fluid connector such that a user must intervene to expose the access site. The cover subsequently returns essentially to a covering position after disconnecting from the fluid connector. The cover may provide aseptically effective agents to the access site. This may be accomplished by several features of the cover, as described herein and summarized in the figure descriptions that follow.

As used herein, the term "access site" refers generally to a fluid port providing entry by a piercing, penetrating, or inserting device. By way of example, an access site includes the female port of a needle-free valve and a penetetrable septum accessible by cannula, e.g., blunt cannula. Penetrable septum may include pre-slit and un-slit septum. The access sit includes the adjacent area in proximity to the access site.

As used herein, the term "fluid" refers to a gas, a liquid or a combination of a gas and a liquid.

As used herein, the term "aseptically effective agent" refers to chemicals or compositions of matter that either kill or prevent growth of virulent organisms. A preferred aseptically effective agent is an anti-microbial agent. Anti-microbial agents include antibacterial agents which kill bacteria, antiviral agents which kill viruses, antifungal agents which kill fungi, and anti-parasitic drugs which kill parasites. Aseptically effective agents include biocides and antibiotics.

As used herein, the phrase "microorganisms," refers to, for example, Gram positive and Gram negative bacteria, including resistant strains thereof, for example methicillan-resistant Staphylococcus aureus MRSA, vancomycin-resistant Enterococci VRE and penicillin-resistant Streptococcus pneumoniae PRSP strains. Preferably, it is defined to include all bacteria Gram+, Gram– and acid fast strains and yeasts such as Candida albicans. Most preferably, it is defined to include all bacteria Gram+, Gram–, and acid fast, yeasts, and both envelope and naked viruses such as human influenza, rhinovirus, poliovirus, adenovirus, hepatitis, HIV, herpes simplex, severe acute respiratory syndrome SARS, H5N 1 viruses, and avian flu.

As used herein, the term "biocides" refers generally to a chemical agent which inactivates living microorganisms. Biocides include, for example, agents of broad spectrum activity, agents that inhibit growth e.g., bacteriostatic, fungistatic, or sporistatic and agents that kill the target organism e.g., bactericidal, fungicidal, sporicidal, or virucidal.

As used herein, the term "containing," when referenced in regard to an aseptically effective agent, refers to any method of incorporating the agent to a fluid connector cover. This may include, for example, melt addition of the agent to a polymer melt during extrusion or manufacturing; topical application methods; absorbable impregnated pads; and other non-standard methods such as plasma treatment, electrostatic attachment, vapor deposition, radiation surface graft co-polymerizations using for example UV, gamma rays and electron-beam radiation sources, or the use of chemical initiation to produce graft copolymerized surfaces having anti-microbial activity, etc.

The cover member of the cover adapter at least partially covers the access site of the connector, providing a covering relationship with the access site. The covering relationship includes direct contact or being in close proximity to the access site. This may prevent many of the infections typically caused by touch contamination, for example, at the injection site of infusion devices.

The fluid connector cover may function passively. Functioning "passively" means that unless a practitioner actively forces the cover off of the access site, the fluid connector cover remains in a covering relationship with the access site, at least until and before the first use of the connector. By way of example, the natural state of the fluid connector cover is covering the access site, which generally refers to a requirement that a user actively forces the cover off of the access site, thus, the fluid connector cover will be positioned at or over the face of the access site in its natural state. This feature may guard against misuse and provide for the face of the access site remaining protected from possible contamination. For example, using the fluid connector cover herein described, nurses, clinicians or other medical professionals may not need to re-cover the fluid connector. Therefore, the possibility of the cover falling off or being lost and/or discarded and exposing the access site is reduced or eliminated. The passive functionality includes, for example, a pre-loaded returning force allowing the cover to return to the access site upon disconnect. The returning force may include a preload condition e.g., a load where the access site will remain covered in the event that the returning force yields under normal operation. By way of example, the returning force may be supplied with a spring, elastomeric material or cantilevered or lever beam. The pre-load force may create a condition where the access site will remain covered should the pre-load elements yield or take a set under normal operation.

The fluid connector cover herein described may be designed such that a minimal number of components are added to an existing fluid connector. These designs and other features of the fluid connector cover herein described may utilize many of the parts already found in fluid connectors, such as needle-free valves. This may limit additional parts and associated costs as well as new or complicated assembly procedures. In addition, changes to current needle-free valve parts may be done without complicating tooling, and many of the herein disclosed designs may be made with an open/close mold action, minimizing production cost.

The fluid connector cover may operate substantially automatically upon engagement by an external device with the access site without user intervention of the fluid connector cover. For example, the cover member may comprise extending flexible arms which provide for deflection of the cover member when the external device engages the access site. The cover member may be comprised of two or more mating sections which form a cover over the access site when in an initial state. The mating section may be deflected away during engagement. Flexible arms may provide a load to the mating sections in the initial state such that upon disengagement of the external device the segments may return to the initial state covering the access site.

The fluid connector cover herein described may be integrated with connectors comprising access sites. The fluid connector cover herein described may be integrated into the connector housing, by way of example, through a flexible beam connection, strap connection, or snap means. Other ways of integrating the fluid connector cover to the connector housing may include a cylindrical clip adapted to secure around at least a portion of the housing of the connector, or a strap fitted around the housing. The fluid connector cover herein described may provide for a mating hole and lug configuration such that activation of the cover is provided by a pivoting action. The fluid connector cover herein described may be adapted to connectors comprising integrated standard threads to provide connection with a female luer, and/or snap on or rest over an access site of a fluid connector. The fluid connector cover herein described may comprise cutouts such as to allow snap-fit-like flexibility for variable sized valves.

The fluid connector cover herein described may stay external to a fluid connector housing and may touch the surface of the access site. The cover may require removal before accessing the access site and to actuate the fluid pathway. The cover may deform to account for misalignment and feature variation of the connector housing access site so that the cover adequately returns and adequately seals the access site preventing bacterial ingress. Elastomeric portions of the cover may be used for this purpose and such elastomeric portions may be joined to any other portion of the device.

A fluid connector cover may comprise a housing. The housing and other components attached or adapted for attachment thereto may be of plastic construction or may be fabricated out of one or more materials designed to withstand chemical attack from substances, such as solvents and IV drugs. Materials include for example, thermoplastics, engineering thermoplastics, filled or unfilled, and composites. Thermoplastics include materials such as polybutylene terephthalate PBT, cyclic olefinic copolymers COC's, thermoplastic polyurethanes TPU, rigid polyvinyl chloride PVC, and polycarbonate PC.

In one aspect, the fluid connector cover comprises a cover adapter body. The cover adapter body may be integral with the fluid connector housing. The cover adapter body may provide attachment means for securably attaching to the fluid connector housing. In one aspect, the fluid connector cover comprises a rigid member. The rigid member may be integral with the fluid connector housing or may be integral with the cover adapter body. The rigid member may be cooperatively coupled with a cover member that provides for covering the access site.

In one aspect, the fluid connector cover comprises a flexible member. The flexible member may join the rigid member to the cover adapter body or may join the rigid member to the connector housing. The flexible member may comprise a thinned wall or narrowed width section of the rigid member. The flexible member may be connected to the rigid member and be positioned to contact the fluid connector housing. The flexible member may provide a load to the rigid member. In one aspect, at least a portion of the flexible member is tensioned to provide load or pre-load, for example, stretched and/or bent. In another aspect, the flexible member is compressed to provide load or pre-load.

The use of the phrases "flexible member" and "rigid member" are to be taken in context as elements used together in the operation of the fluid connector cover and not necessarily a representation of a material property of the members. For example, rigidity and flexibility of the members may be provided by varying thickness and cross-sectional area of a single material, or the rigidity and flexibility of the members may be provided by using a thermoplastic material and an elastomeric material.

In one aspect, the fluid connector cover comprises a threaded cover member with an integrated strap, the strap having at its opposite end the cover member. The strap may be attached, for example, to the connector housing such that the strap is free to rotate around the connector housing body. The rotation of the strap about the connector housing may provide for facile threaded engagement or disengagement of the cover member. In another aspect, the threaded cover member includes having the strap integrated with the connector housing while the cover member, located at the opposite end of the strap, is free to rotate relative to the strap.

In one aspect, the fluid connector cover herein described is integrated with a fluid connector housing such that the cover member may be vertically translatable and arcuately rotatable about the connector housing. In this configuration, the cover may be pushed down over the access site and/or any threaded elements. Thus, the cover member may comprise integral projecting flexible arms, the arms comprising tracks which securably attach to the housing to provide vertical and arcuate motion to the cover member relative to the connector housing. The cover member may be of a cup-like shape. The cover member may be adapted to snap-fit on the access site, for example to keep the underside covering surface of the cover member flush against the face of the access site. The cover member may also utilize the thread forms on the access site as the mating snap elements.

Passive, Pre-Loaded Return Means

In one aspect, fluid a connector cover utilizes pre-loaded return force allowing the cover to return to the connector housing access site upon disconnect of objects accessing the connector housing and removal of external forces. This return force also creates a pre-load condition where the access site will remain covered under normal operation. The pre-loaded return force may be generated by compressing an elastomeric component or similar material as in rubber, foam, compression spring, torsion spring, or the like.

In one aspect, the fluid connector cover herein described integrates a cover member with a cover adapter body or fluid connector housing by way of a flexible member. The flexible member may be shaped as a beam, lever, cantilever, a loop or arm. The cover member may be positioned at a distal end of the arm, the arm being connected to the flexible beam connected to the body or the housing, for example, in a lever arm-fulcrum flexible beam relationship. Pressing the proximal portion of the arm activates the cover adapter by flexing the beam, which moves the cover away from the access site in an arc-like motion.

In one aspect, the cover member may be configured with a rigid arm positioned between the flexible member and the fluid connector housing, for example, by looping the flexible member over the housing. A looped flexible member may also provide a pre-load to the cover member. In this configuration, moving the cover away from the access site in an arc-like motion tensions the loop, which provides the return load.

In one aspect, the fluid connector cover herein described comprises one or more flexible arms proximally integral with a fluid connector housing, or the flexible arms are adapted to securably attach thereto. The flexible arm is cooperatively coupled with the cover member at the distal end of the flexible arm such that applied force upon the flexible arm toward the connector housing translates the cover member from the access site to provide access thereto.

The fluid connector cover may further comprise a flexible member that surrounds the housing and may be cooperatively coupled to the fluid connector cover. In one aspect, the flexible member provides a restoring force to the fluid connector cover such that the fluid connector cover returns to its initial state covering the access site. The flexible member may be combined with the previously described embodiments. Thus, for the fluid connector cover comprising rigid arm and beam elements, the flexible member may be used to provide a restoring force for or load to the rigid arm. For example, applied force, such as digital pressure from a user, to the lower portion of the rigid arm provides rotation about a clip-like means and, in turn, the beam flexes and creates the restoring force returning the cover over the access site. The connector housing may be a connection point for the clip-like means, and may also restrict the movement of the beam, causing the part of the beam to flex and/or creating or complementing the restoring force to re-cover the access site. The flexible member may snap-on to corresponding lugs integral with the fluid connector housing. The lugs may be designed such that the flexible member deflect when the clip is activated. The flexible member may be, for example, straight or of a U-, V-, or W-shape. Other shapes may be used.

Attachment Means

The fluid connector cover herein described comprises a cover adapter having attachment means for securely fastening with the fluid connector housing. For example, the cover body may comprise a ball/pin and socket, interference-type snap-on structure, a clip or combinations thereof. The fluid connector cover herein described may comprise a clip member formed of the cover adapter body for surrounding at least a portion of the connector housing. The clip member may provide for securing the cover adapter onto the connector housing and may further utilize joining methods, such as adhesives or ultrasonic welding, to prevent relative motion between the connector housing and the cover adapter. The cover adapter may further comprise a flexible beam and arm as described above, such that pressing the lower portion of the arm moves the cover away from the access site of the connector housing in an arc-like motion.

In one aspect, the attachment means include a rotatable clip-like means to provide for rotation of the fluid connector cover body around the outside surface of the connector housing. The cover body may include a flexible segment joining a rigid arm to the cover body, the rigid arm distally terminating in a cover member. The connector housing may comprise a connection point for the clip-like means and a ramp element cooperatively engage the rotatable clip-like means to provide deflection of the flexible segment. The flexible segment may provide a load when the clip-like means are rotated and cooperatively engaged with the ramp element. Deflection of the flexible segment moves the cover member from the access site. The load may re-position the cover member after the clip-like means are disengaged with the ramp element.

In one aspect, fluid connector housing attachment members and corresponding attachment members of the cover adapter are adapted to interact with respect to each other to provide pivotable motion. For example, the cover adapter attachment members and corresponding fluid connector attachment members may, independently, comprise at least one shaft and a generally cylindrical bearing surface.

In another aspect, connection geometry for attachment means that do not integrate with the connector housing may be optimized for manufacturability of the connector. For example, an injection-molded connector housing may comprise attachment members positioned such that the mold tool only requires simple modification rather than retooling. As a means of cost reduction, embodiments of this concept may be integrated into the intended access site. The fluid connector cover may comprise a cover member connected to a distal end of a rigid member, the rigid member joined to the connector by a flexible member arm. Applied force to the rigid member provides flex which moves the cover away from the access site in an are-like motion.

The fluid connector cover may be integrated with a connector housing for example, using a flexible beam connection, strap connection, or snap means. Other ways of integrating are through a cylindrical clip that fits around the body of the housing or a strap fitted around the housing or a strap adapted for connection to any proximal device or object, such as a catheter hub or extension set tubing. Standard threads may be integrated into the fluid connector cover to provide a securable connection with a female luer, or may snap-on or rest over the access site. For example, cutouts in the fluid connector cover body may allow sufficient flexibility for snap-fitting onto any size fluid connector housing.

The cover member may be integrated with the connector housing or may be a separate component of the fluid connector cover. The cover member may be cooperatively joined or integral with a rigid or flexible member, for example, having the shape of an arm connected to the connector housing.

In aspects utilizing an elastomeric closed loop that encircles or surrounds the connector housing when assembled, the band forming the elastomeric closed loop may be surrounded on one or more sides for some length by features integrated or attached to the connector housing. This anti-tampering/secure attachment feature or set of features help reduce the possibility of tampering or unintended removal of the cover adapter from the connector housing by entrapping or otherwise limiting access to the closed loop/connector housing interface.

In one aspect, a stake/swage operation is employed as a means of secure attachment. Thus, extrusions from the connector housing pass through receptacles in the cover adapter. A secondary process may be used to swage, stake or otherwise create an interference that reduces the possibility of the cover adapter from being removed from the connector housing. Other secure attachment means include, but are not limited, to a ball and socket joint and a snap-fit arrangement between the cover adapter and the connector housing.

The cover may be adaptable to commercially available connectors including, but not limited to, Cardinal Health SmartSite® and SmartSite® Plus, ICU Medical Clave®, CLC2000®, and TEGO™, BD Posiflow™ and Q-Syte™, Baxter FLOLINK, CLEARLINK, and INTERLINK, B|Braun ULTRASITE®, Medegen MaxPlus™, Halkey-Roberts Swabable Luer Valve, RyMed Technologies InVision Plus®, Vygon Bionector®, and Borla bSite™. Additionally, the cover may be adaptable to female connectors of stopcocks and IV manifolds.

Elastomeric Material

In one aspect, the fluid connector cover comprises an elastomeric material. The elastomeric material may—secure the cover member over the access site and/or provide a returning force. The elastomeric material may be combined with the previously disclosed embodiments. The elastomeric material may be integrated with the clip-like means or other attachment members. The elastomeric material may be integrated, for example, over-molding or adhesive bonding. Attachment means connecting the fluid connector cover body to the connector housing access site may be a pivoting connection. The lower portion of the attachment means may be covered with the elastomeric material to improve tactile feel, finger control, and/or ergonomic stability. The attachment means may be made entirely of an elastomeric material such that the rigid member and flexible member functioning may be controlled by material thicknesses and cross-sections. The elastomeric material may provide for improved sealing between the cover member and the access site by reducing or eliminating any gaps between the access site and cover member. The elastomeric material may provide for conformal sealing between the cover member and a non-planar access site, for example. Various elastomeric materials may be used, such as, but not limited to, reaction-injection molded RIM elastomers, silicones, polyurethanes, thermoplastic elastomers TPE e.g., SANTOPRENE™, and synthetic polyisoprenes.

Shroud

The fluid connector cover herein described may include shroud elements. In one aspect a cover member shroud element at least partially surrounds the cover member such as to cover the sides of the access site. A portion of the cover member shroud element may provide for accepting and/or securing of the access site upon return of the cover member to its initial state. In addition, the cover member shroud may keep the access site and/or access site threads free from debris. The portion of the cover member shroud may include a cut out or missing section, for example, positioned opposite the rigid member attachment point to cover member. In another aspect, an anti-snagging shroud may be incorporated into the cover adapter or connector housing to reduce the risk of the cover adapter becoming snagged on items in its environment. Anti-snag features include for example, protrusions from the finger pad portion of the cover or fully cover the space between the finger pad and the connector port. Anti-snag features preferably are incorporated without compromising user activation. The shroud elements may either be plastic or elastomeric.

Aseptically Effective Agents

The fluid connector herein described may comprise an aseptically effective agent to provide infection controlling properties to the connector. Medical articles are frequently fabricated from polymeric materials such as polypropylene, silicone rubber, ABS, or polyurethane by molding and extruding techniques. Imparting aseptically effective properties to such medical devices made from polymeric materials includes, for example, incorporating an aseptically effective agent into the material during the process of forming the cover adapter. In one aspect, the aseptically effective agent is an anti-microbial agent.

The aseptically effective agent containing fluid connector cover preferably rapidly inhibits and controls the growth of microorganisms. For example, an anti-microbial agent may provide a reduction in the concentration of a broad spectrum of microorganisms by a magnitude of at least 1 $\log_{10}$ as measured by shaker flask method, liquid droplet challenge test, and/or aerosol challenge test within about 30 minutes. The anti-microbial agent containing fluid connector cover may lead to a reduction in microbial concentration by a factor of 3 $\log_{10}$ i.e., reduction by $10^3$ colony forming units per gram of material cfu/g within about 30 minutes, The anti-microbial agent containing fluid connector cover may lead to a reduction in microbial concentration by a factor of 4 $\log_{10}$ or more within about 30 minutes.

The anti-microbial agent containing fluid connector cover may provide at least a 1 $\log_{10}$ reduction in the transfer of a broad spectrum of viable microorganisms when contacting another surface as compared to an untreated control item as measured by the contact transfer protocol, for example, as outlined in U.S. Patent Application Publication No. 2004/0151919, incorporated herein by reference. The anti-microbial agent containing fluid connector cover may be non leaching. "Non-leaching" anti-microbial surface is one that passes ASTM E2149-01 testing protocol entitled "Standard Test Method for Determining the Anti-microbial Activity of Immobilized Anti-microbial Agents Under Dynamic Contact Conditions." The lack of a zone of inhibition with the treatment agents chosen may demonstrate the active species does not leach from the treated substrate.

Aseptically effective agents may be compounded in thermoplastic resins or elastomers to produce a concentrate which is then dry blended with the virgin resin and co-molded or overmolded. For example, an anti-microbial agent may be generally distributed throughout the bulk of the cover such that enough of the anti-microbial agent is present on or near the access site surface to provide anti-microbial activity. Concentration of the anti-microbial present on or near the surface of the access site may depend on several factors including anti-microbial concentration in the melt relative to the main body of resin or type of resin, processing conditions and thermal history, crystallinity of the resin, and relative thermodynamic compatibility of the resin and the anti-microbial. The anti-microbial may be compatible with thermoplastic resin in the melt for proccesability, and yet may be less compatible with the resin at ambient conditions so that the anti-microbial agent may migrate to a certain extent to the surface of the cover. Processing aids may be used to assist migration of the anti-microbial agent to the surface of the cover in contact with the access site.

Aseptically effective agent that may be used in the fluid connector cover as herein described to provide anti-microbial action, include, but are not limited to, 1-alkyl-1,5-diazapentane, alexidine, alkyl-amino-alkyl glycine, alkyl sulfosuccinate, anatase $TiO_2$, bamboo extract, benzalkonium chloride, bromo-compound, cetrimide, cetylpyridium chloride, chitosan, chlorhexidine, chlorhexidine biguanide, chlorhexidine diacetate, chlorhexidine digluconate, citric acid, cyanobutane, dialkyl-dimethyl-phosphonium salt, dithiocarbamate, hexachlorophene, hydrogen peroxide, hydrotropes strong emulsifiers and chaotropic agents alkyl polyglycosides, isothiazolin, neem oil, poly-hexamethylene biguanide, polyphenols from green or black tea extract, polyquaternary amine; metal-containing species and oxides thereof, quaternary ammonium compound, quaternary ammonium compounds benzalkonium chloride, quaternary ammonium siloxane, quaternized cellulose and other quaternized polymers, silver salts such as silver sulfadiazine either in particle form or incorporated into support matrix or polymer, stabilized oxidants such as chlorine dioxide, stabilized peroxide urea peroxide, mannitol peroxide, sulfites sodium metabisulfite, thiazole, thiocynate, thione, tourmaline, light-activated porphyrins, triclocarban, triclosan, and salts thereof, and lower alcohols such as ethanol and isopropanol. Depending on the particular material used and the method of incorporation of the aseptically effective agent into the product, many of the above agents may be used alone or synergistically to achieve product properties of interest. To reduce the evaporation rate of the aseptically effective agent, a carrier such as oil or the like may be used in combination with the aseptically effective agent. In the embodiments where the cover member comprises an absorbent such as polyurethane hydrophilic foam, antimicrobial materials may be impregnated in the absorbent material, or liquid solutions of the antimicrobial materials in isopropyl alcohol, povidone iodine, chlorhexidine, or the like may be contacted with the absorbent material.

Any surface or combination of surfaces of fluid connector cover herein described may include and/or be impregnated, and/or otherwise covered, with an aseptically effective material. The aseptically effective material may comprise an anti-microbial agent. The cover member may comprise separate and/or replaceable element containing an anti-microbial agent. The separate element may be adapted to absorb new or additional anti-microbial agents. For example, the separate element may include a sponge, foam or absorbable material sized to be received by the cover member. The separate element may be secured temporarily or permanently to the cover member. The separate element may be secured by one or more securing elements integral with the cover member or shroud. The cover member may comprise an elastomer, plastic, foam, sponge-like material or any combination thereof.

Cover Member

The cover member may comprise portions constructed of elastomeric, plastic, absorbent e.g. sponge or foam or any combination thereof and may comprise any geometry determined to be advantageous for effectively disinfecting its corresponding access site of a connector housing. This may be, but is not limited to geometries that exactly or closely replicate the geometry of the access site geometries of the connector housing. The cover portion may comprise a reservoir which may provide aseptically effective media to the access site of the connector housing. Aseptically effective media may be metered, for example, either passively or actively through a sponge-like or foam or it may alternatively be metered through a small orifice. The cover portion may extend beyond the top surface of the fluid connector housing to provide a more tortuous path for potential contamination.

Aseptically Effective Agent Reservoir

The cover member may comprise a reservoir for containing the aseptically effective agent. The reservoir is most useful and suitable when the valve is left in the open position for extended periods of time. Upon passive return of the cover member to the access site, the reservoir is available to administer additional disinfecting solution to the cover portion. The reservoir may comprise an elastomer, a plastic, a foam, a sponge-like material or any combination thereof adjacent or integral with the cover member. In the embodiments utilizing a reservoir, the cover member can be sealed with a user-removable lidding tab while the product is on the shelf prior to its use, as discussed herein.

Cooperative Access Port and Cover Member Seals

The cover member may include sealing rings, which may be elastomeric, so that a seal is generated about the mating fluid connector housing access site. Sealing rings may act to reduce the evaporation rate of an antimicrobial agent present at the cover member and may also serve as a barrier to bacteria when in its assembled, closed state. In one aspect, the cover adapter seals with the top surface of the fluid connector housing via a continuous sealing surface, herein described as an elastomeric ring. The ring can be of varying cross-sections, such as triangular, flat rectangular, circular, curved, a combination of these shapes, and the like. This sealing feature can be integrated with either the fluid connector housing or the cover adapter. Similarly, the cover portion may come down beyond the top surface of the fluid connector housing to provide a more tortuous path for potential contamination. The cover adapter may seal with the access site of a fluid connector housing via a continuous seal. This may prevent, or otherwise reduce, the evaporation of antimicrobial fluids where used as well as the opportunity for contaminants to migrate onto the access site.

Locking Means

The fluid connector cover may comprise an lock providing tamper resistance or to avoid accidental opening of the cover. Integrated locks or tamper resistance features keep the cover from being opened inadvertently e.g., by a patient rolling over or keeping a patient from "playing with it". In one aspect, a lock feature may be utilized in the fluid connector cover to prevent unintended activation. For example, interference requiring the user to push the cover adapter up and away from the connector housing access site with respect to the connector housing central axis may be required. In this un-locked position, the user is then free to activate the cover adapter by providing a force at the finger pad area of the rigid member.

In another aspect, a locking member can be attached to the finger pad area of the cover adapter. The locking member is comprised of a push pad area at one end and a second terminated end. The locking member and finger pad of the cover adapter couple together such that the locking member is free to rotate about a pivot point and the terminated end of the locking member contacts the connector housing while the cover adapter is in the normal state. The finger pad of the cover adapter may have an integrated stop that the locking member rests against in the locked state defined as angle in which the locking member must be set to in order to prevent activation. When the user presses the push pad of the locking member towards the finger pad, the lock is released thereby freeing the cover adapter for activation. When the cover adapter is then activated, the locking member is further free to rotate so as not to prevent adequate activation. To lock, the push pad is pulled back to the locking angle. The terminated end of the locking member may be a U-shape or a flat pad. The locking member may have elastomer to act as friction for locking at the terminated end.

Mount and Locking Device for Anti-Contamination Cover and Fluid Connector Housing In one aspect, a mounting and locking device is provided which securely holds the fluid connector housing with cover adapter as described herein. The fluid connector housing with a cover adapter is held securely by retention features of the mount and locking device. In one aspect, the connector housing profile or protrusion distance from the surface of the skin is minimized. In one aspect, the mount and locking device is securable in one of two positions, locked closed, or open/access. In the locked closed position, the cover adapter maintains constant contact between the integrated cover adapter and the fluid port access site. Maintaining contact between the integrated cover adapter and the fluid port access site reduces the potential for infectious organisms to come into contact with the access surface of the connector housing. In the open or access position, the cover adapter maintains the fluid port accessibility for connection with other devices.

In one aspect, the mount and locking device securely holds an IV extension set after the catheter has been inserted into the patient, constraining the catheter and IV extension set. More importantly, the mount and locking device restricts movement of the catheter/needle, reducing the potential for "pistoning." For example, the retention features may be configured for a IV set with male luer or catheter hub to restrict the catheter from moving axially, thereby reducing pistoning. Reduction in pistoning decreases the potential for infection.

Methods of preventing or eliminating contamination of an access site of a fluid connector are provided. As used herein, the term "prevent" and its grammatical equivalents refer to any reduction of the level and/or virulence contamination of the access site. As used herein, the term "contamination" and its grammatical equivalents refer to material not intended to be present on or in the access site. Preventing or eliminating contamination of an access site of a fluid connector may include, for example, providing a passive cover member positioned in a covering relationship with the access site. The cover member may prevent or eliminate contact of the access site with the user, material and/or surfaces that may contain virulent material. The cover member may passively cover the access site until user intervention provides access to the access site, for example, using digital pressure applied to the fluid connector cover.

Referring now to the drawings, various illustrative embodiments will be described. Referring now to FIG. 1, fluid connector cover 130 may be integrated into fluid connector housing 50 comprising an access site 208. When proximal end 103 of the rigid arm 99 is pushed towards the housing, the distal end of the arm comprising cover member 101 pulls away from the access site of the housing in an arc-like motion, allowing for insertion of a mating connector. Cantilevered flexible member 102 bends to provide a load or force to substantially return the distal end of the arm and cover member 101 back over the access site, for example, upon disconnection of the mating connection. Finger grips 104 may be added for finger stability and ergonomic control.

Referring now to FIGS. 2A and 3, fluid connector cover 140 comprises cover adapter body 12 non-integrated with fluid connector housing 50b. The body attachment members 106 provide for clip-on and/or adhesion onto different shaped connector housing bodies. Cut-out 128 in the cover adapter body may provide attachment on connectors with external geometry protruding from the intended access site body, such as Y-shaped valve 180, as shown in FIG. 3. Shroud 105 may be provided for additional access site coverage and stability of the cover member. The shroud may extend past the access site.

Referring now to FIG. 2B, mating connector 123 attaches to fluid connector housing 50B with fluid connector cover of FIG. 2A. Flexible member 102B bends to provide a load as digital force is applied to the proximal end 103B of rigid member 99B. Upon disconnection of the mating connection body, the load in the rigid member returns cover member 101B to the access site.

Referring now to FIGS. 4-5, fluid connector cover 150 comprises cover member 108 with threaded element 68, the cover member integrated with strap 107 having annular clearance around fluid connector housing 50C. Cover member 108 may be screwed onto the threaded element 66 of the fluid connector housing to cover access site 208 while the strap 107 may rotate around the housing. Fluid connector cover 160 comprises threaded cover member 109 fitted with annular clearance to flexible strap 110 integrated into the fluid connector housing. Cover member 109 may turn or spin freely in the strap, for example, while screwing onto threaded elements 66B of connector housing.

Figure 6:
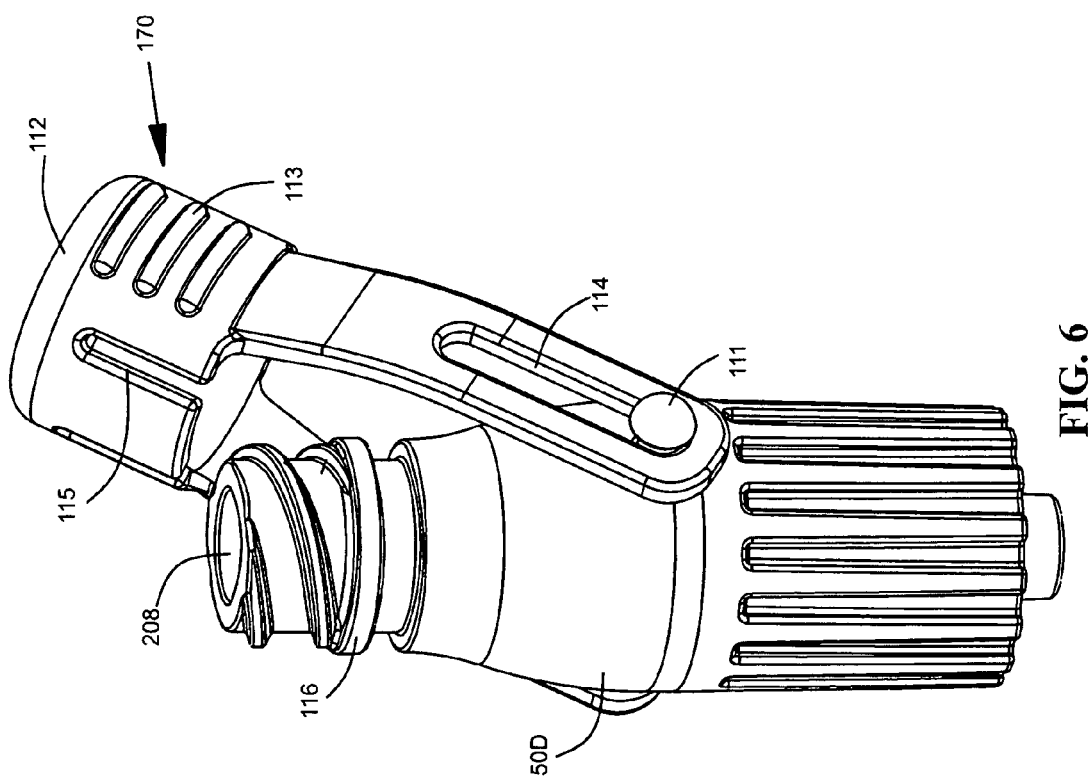
FIG. 6 is a perspective view of an embodiment of the fluid connector cover.

Referring now to FIGS. 6-7, fluid connector member 170 comprise cover member 112 which provides for snap-on functionality of cover member 112 onto corresponding receiving elements or set of elements 116 of fluid connector housing 50D. Cutouts 115 allow the cover member walls to flex when engaging elements 116. Groove 114 of the cover member securely attaches onto corresponding attachment members 111 of connector housing 50D. The grooves allow the cover member to be lifted and swung away from access site 208 in an arc-like motion and provide a load to return cover member to a position over access site. Finger grips 113 integrated into cover member 112 provide for application and removal of the cover member. Undercuts 117 on cover member 112 secure to corresponding engaging elements 116 on housing.

FIGS. 8 and 9 depict fluid connector covers where the translation of the cover member corresponds to the direction of the applied force. Thus, referring now to FIG. 8, actuator 120 is joined to rigid arm members 121 and flexible arm members 118. Flexible arm members 118 secure to housing with snap-on attachment means 119. Arm members 121 transmit load to flexible linking arms 118 when pressed inward, moving cover member 122 away from the access site. Upon disconnecting, tension in the flexible arm 118 provides force for the cover member 122 to return back and cover the access site.

In FIG. 9, actuator 120A comprises a continuous element 124 having attachment means, such as clip-like element 125, securing actuator 120A to fluid connector housing, terminating at cover member 122A. Continuous element 124 comprises opening providing access to access site 208. Continuous element 124 may be U-, V, or W-shaped to provide a load to passively translate cover member 122A back to initial state covering access site. Cover member 122A includes an angled lead-in element 126 to aid in seating cover member 122A upon returning to its initial state.

Referring now to FIG. 10, flexible member 102C is shown with alternate beam geometry. The "s" shaped geometry may minimize stress and/or reduce the actuation force. Other shapes and configurations are envisaged such as to provide a force for passively returning the cover member to the access site. Referring now to FIGS. 11-12, fluid connector cover 200 is shown. Cover adapter body 212 comprising flexible member 201 at least partially surrounds fluid connector housing 202. Rigid arm 204 attaches to cover adapter body between cover member 203 and proximal end 205. Digital force to the proximal end 205 translates cover member 203 off access site 208 in an arc-like motion to expose the access site. Housing retaining means 207 on fluid connector housing 202 restricts the movement of flexible member 201 providing flexation and load for returning cover member to the access site.

Figure 16:
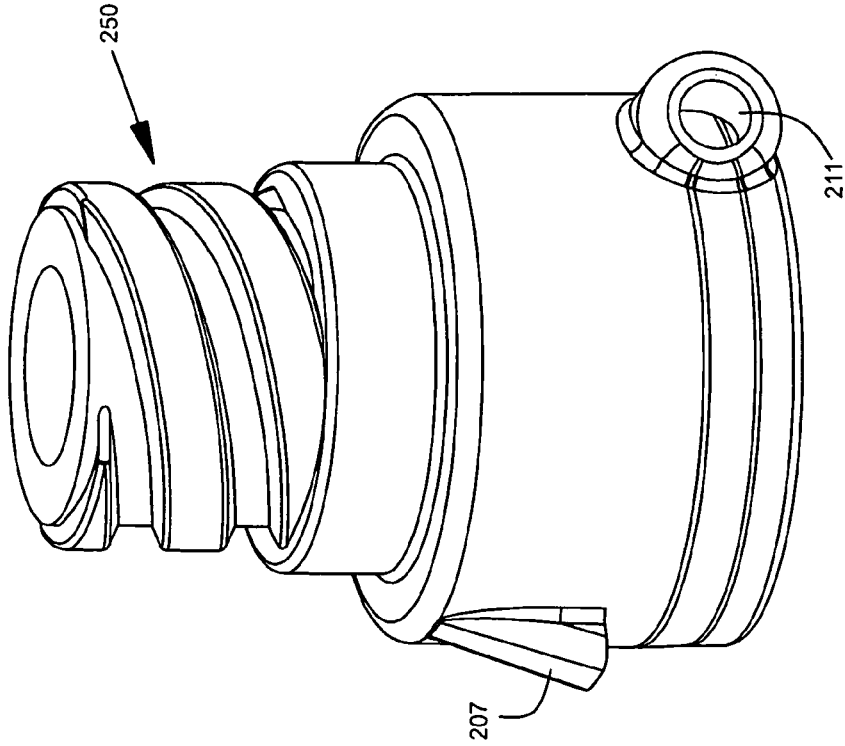
FIG. 16 is a perspective view of an embodiment of a fluid connector housing.

Referring now to FIGS. 13-14, fluid connector cover 200 is shown attached to a y-configuration connector housing 209 in an initial state and in a user-activated state exposing access site 208. Referring now to FIG. 15, cover adapter 200 of FIGS. 11-14 is shown. Attachment members 210 may create a pivot point for the cover adapter body 212. Lead-in chamfers 213 aid in vertical z-axis assembly of cover adapter to housing. Referring now to FIG. 16, fluid connector housing 250, with corresponding attachment members 211 to attachment members 210 of FIG. 15, are shown. Attachment members 211 provide snap-in-place and pivoting of cover adapter 200.

Figure 17:
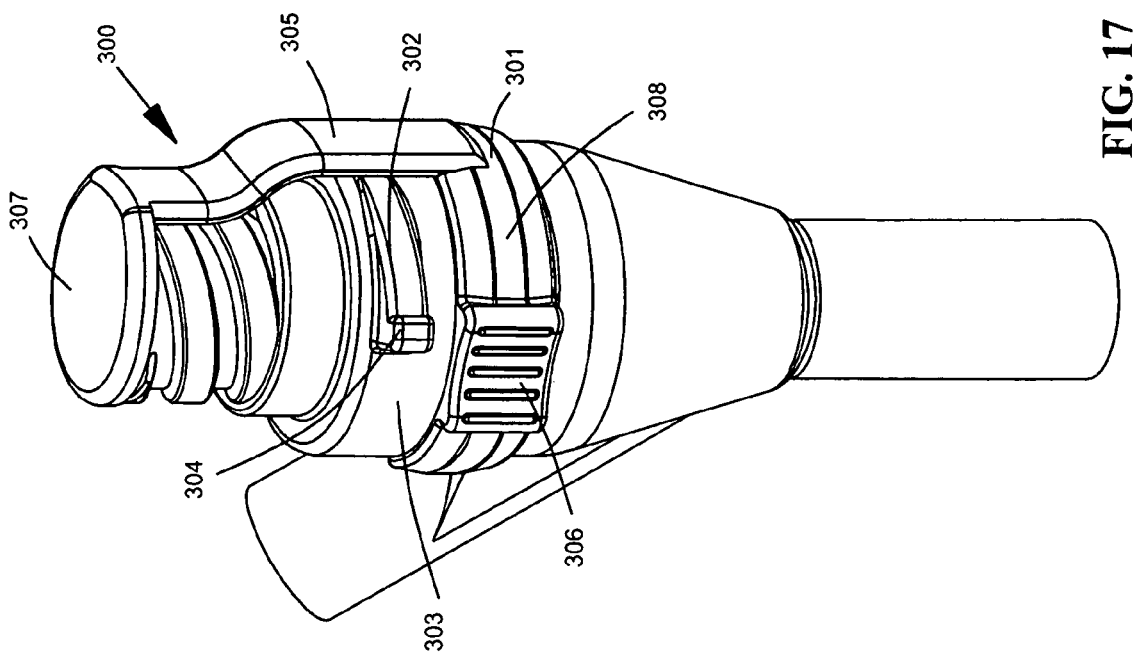
FIG. 17 is a perspective view of an embodiment of the fluid connector cover.

Referring now to FIGS. 17-18, fluid connector cover 300 is shown in an initial state and an activated state, respectively. Collar 308 connects cover adapter body 301 to fluid connector housing 303. Beam-like flexible member 305 connects collar 308 to cover member 307. Rotation about fluid connector housing 303 forces flexible member 305 up ramp 302. Ramp 302 is shown integrated on fluid connector housing 303. Finger grips 306 may be added to the collar for manipulation. Rotation of flexible member may be limited by housing retaining member 304. The ramp provides for flexible member 305 and cover member 307 to expose access site 208. Referring now to FIG. 19, cover adapter body 301 of the fluid connector cover of FIG. 18 without connector housing is shown. Cutout 310 of collar 308 provides for snap-on assembly of cover adapter to a corresponding fluid connector housing.

Figure 20:
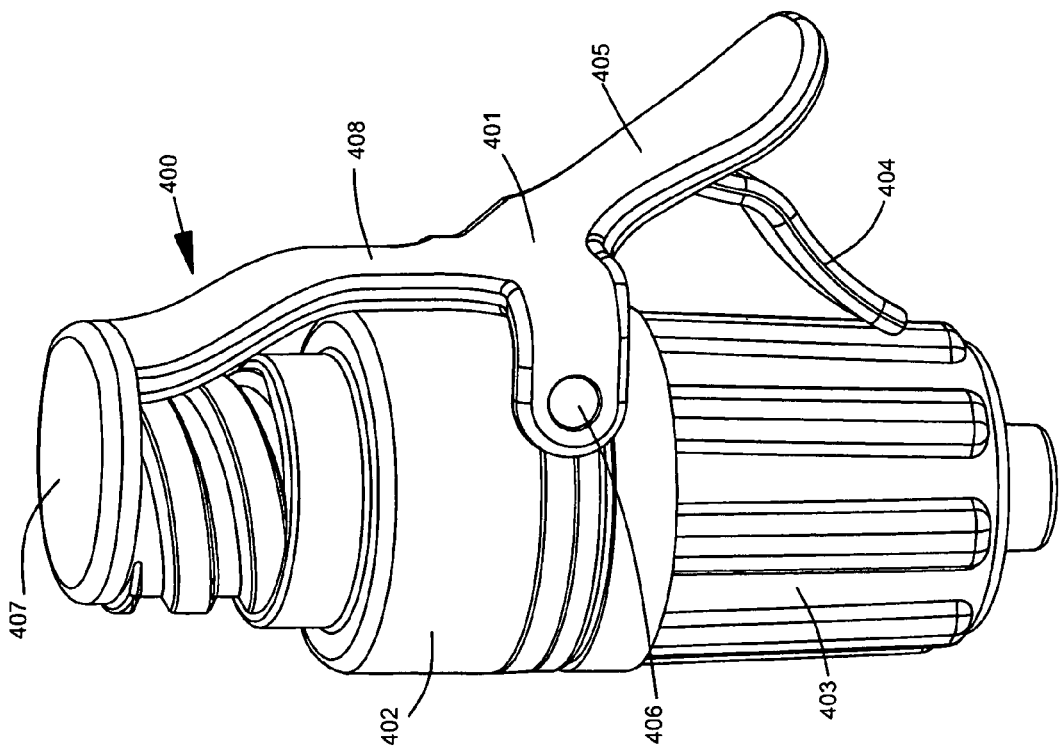
FIG. 20 is a perspective view of an embodiment of the fluid connector cover.

Referring now to FIG. 20, fluid connector cover 400 is shown. Cover adapter body 401 is attached to the fluid connector housing 402 with a peg and hole-like assembly 406, which also acts as a rotation or pivot point. Finger-like flexible member 404 connects to proximal end 405 of rigid arm 408. Flexible member 404 provides load to rigid arm. Digital pressure to proximal end 405 causes flexible member 404 to deflect against lower fluid connector housing 403 and rigid arm 408 to deflect outward, translating cover member 407 from access site.

Figure 21:
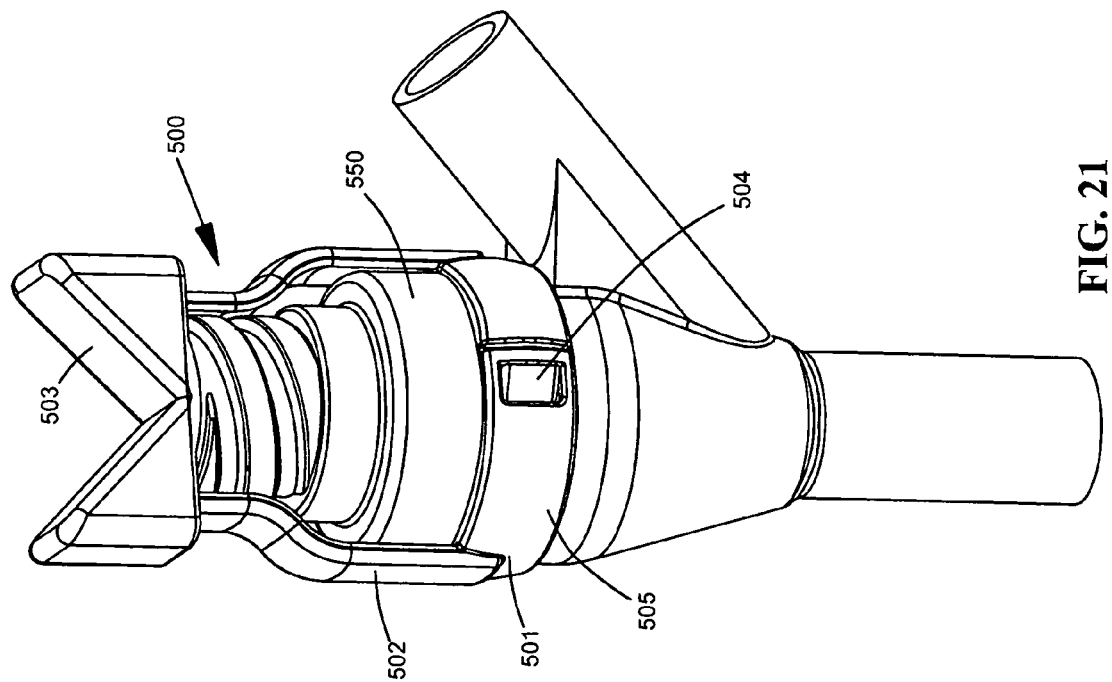
FIG. 21 is a perspective view of an embodiment of the fluid connector cover.

Referring now to FIGS. 21-22, automatic fluid connector cover 500 is shown. Cover adapter body 501 is fastened onto the fluid connector housing 550 by a collar 505 with living hinge 507 and snap-fit element 504. Cover segments 503 connect to flexible member 502 of the cover body. Insertion of external device 506 spreads cover segments apart to allow access to the access site.

Figure 25:
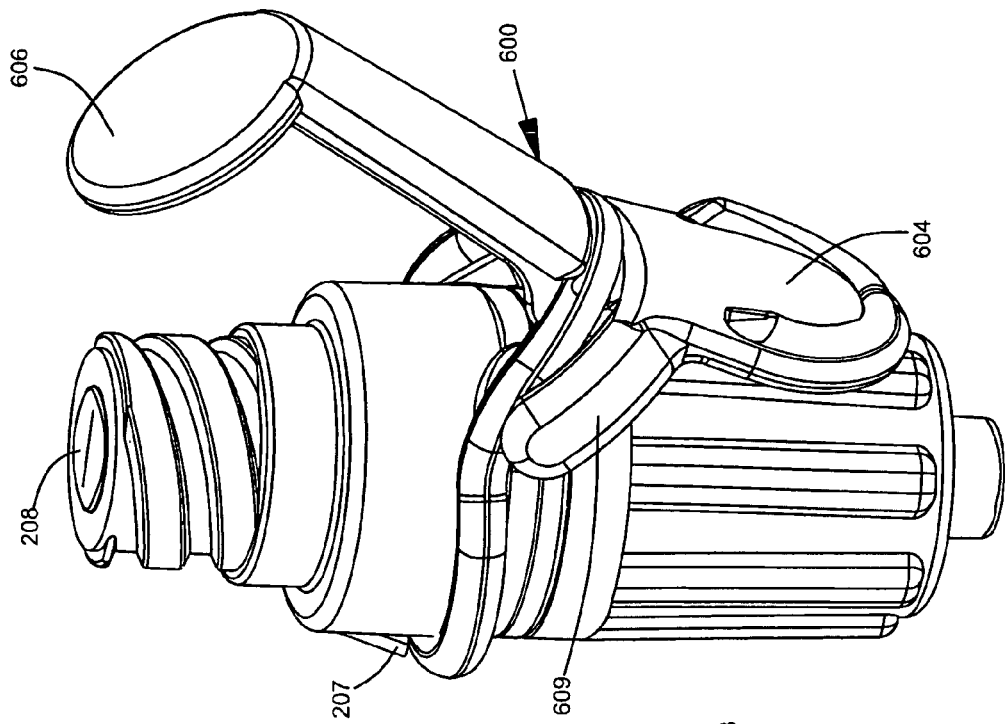
FIG. 25 is a perspective view of the embodiment of the fluid connector cover of FIG. 23 in an activated state.
Figure 24:
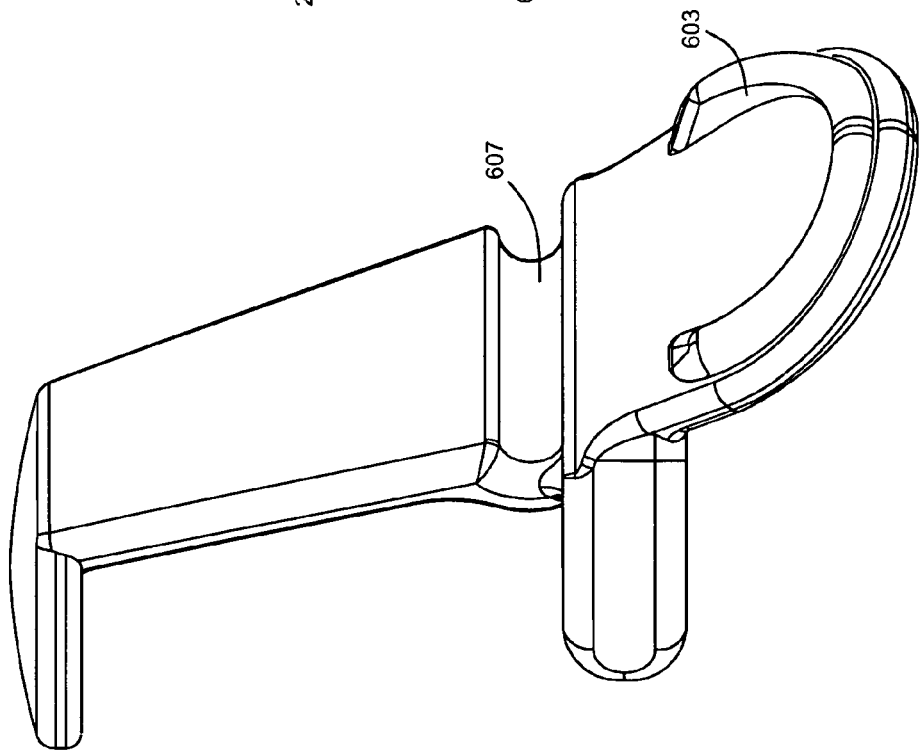
FIG. 24 is a perspective view of an embodiment of a cover adapter.

Referring now to FIG. 23, fluid connector cover 600 comprises cover adapter body 609 connected to the fluid connector housing 650 between rigid arm 605 proximal end 604 and distal end having cover member 606. Elastomeric member 601 holds the cover member 606 adjacent the access site in an initial state. Digital pressure to the proximal end 604 translates cover member 606 from the access site in an arc-like motion to an activated state. Elastomeric member provides force to rigid arm 605 for returning of the cover member to the access site. Housing retaining means 207 may be integrated with the fluid connector housing for retaining elastomeric member and/or preventing slippage. Referring now to FIG. 24, the cover adapter body without the fluid connector housing and without the elastomeric member, is shown. Retaining element 607 receives elastomeric member and provides grip element 603 for finger stability and ergonomic control. Referring now to FIG. 25, fluid connector cover 600 is shown in the activated state. Digital pressure to proximal end 604 of the rigid member translates cover member 606 in an arc-like motion, exposing access site 208. The connector housing and/or the retaining means 207 allows the elastomeric member to stretch providing a load for returning the cover member over the access site 208. Elastomeric member may be continuous or multiple elastomeric members that may be individually retained by housing retaining elements provided on the housing.

Figures 26A, 26B:
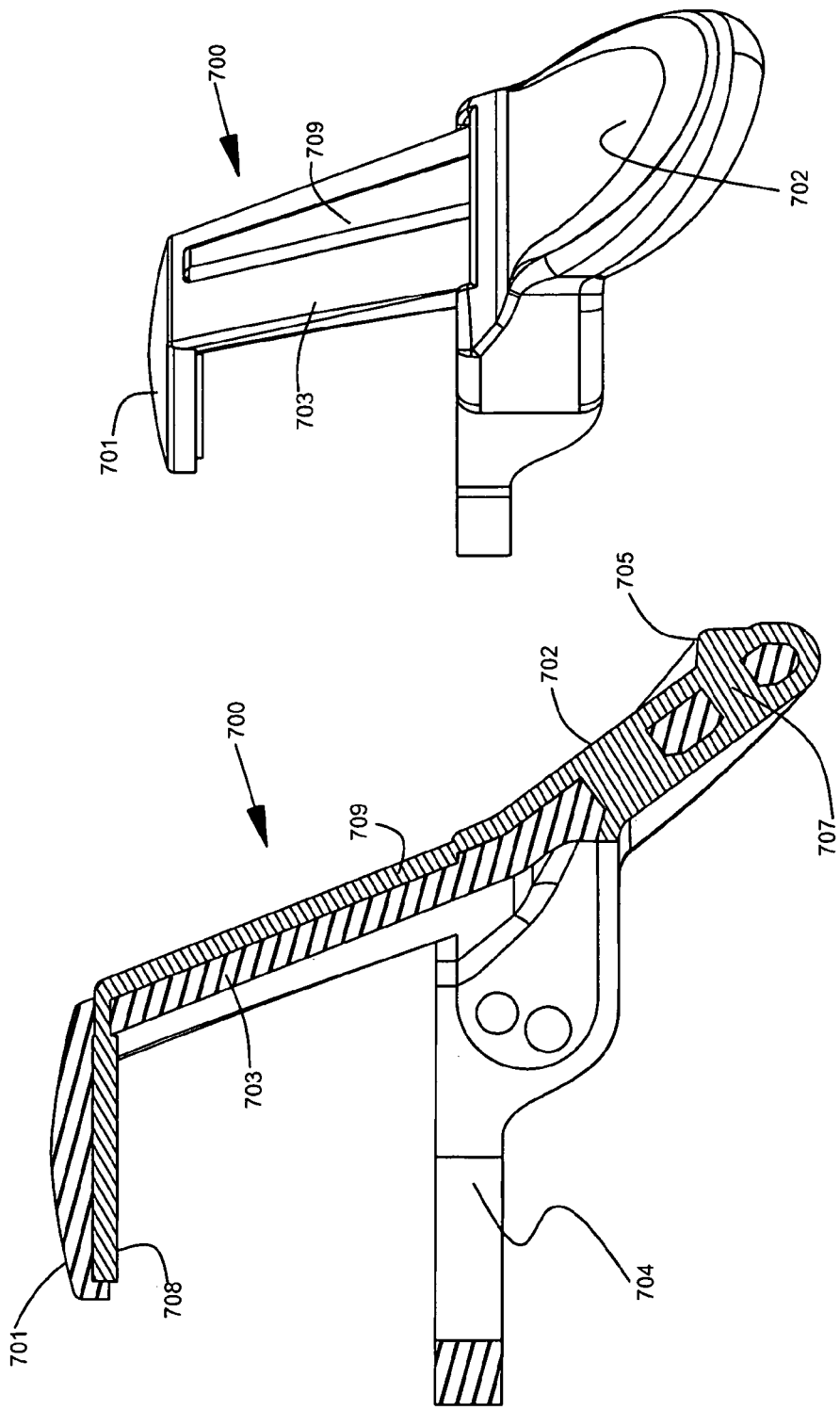
FIGS. 26A and 26B are cross-sectional and perspective views, respectively, of an embodiment of a cover adapter.
Figure 28:
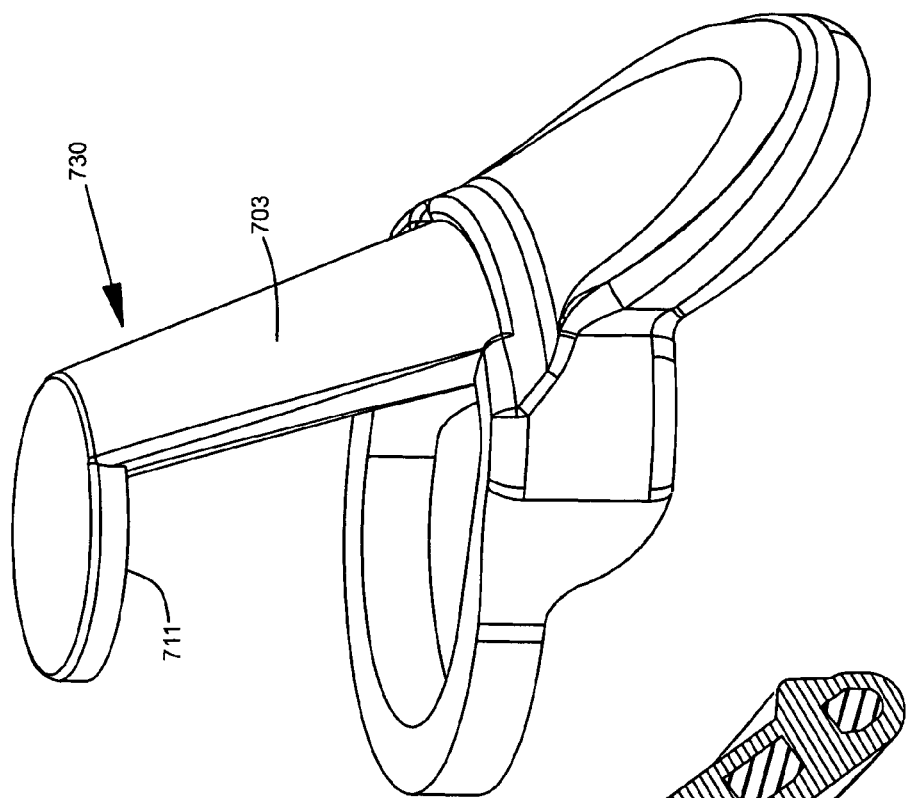
FIG. 28 is a perspective view of an embodiment of a cover adapter.
Figure 27:
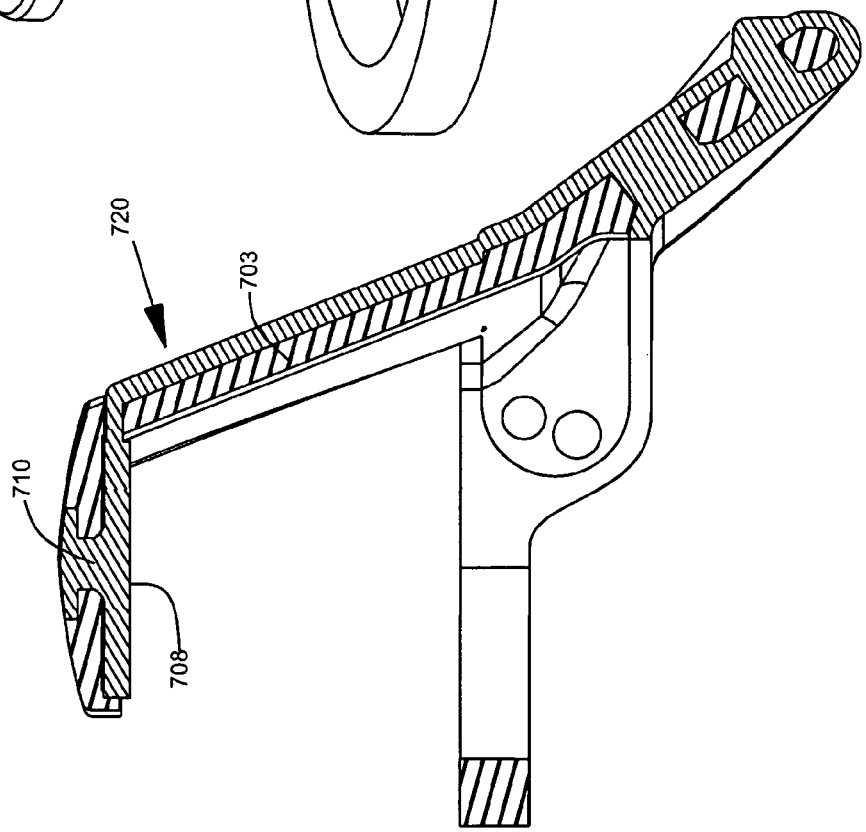
FIG. 27 is a cross-sectional view of an embodiment of a cover adapter.
Figure 30:
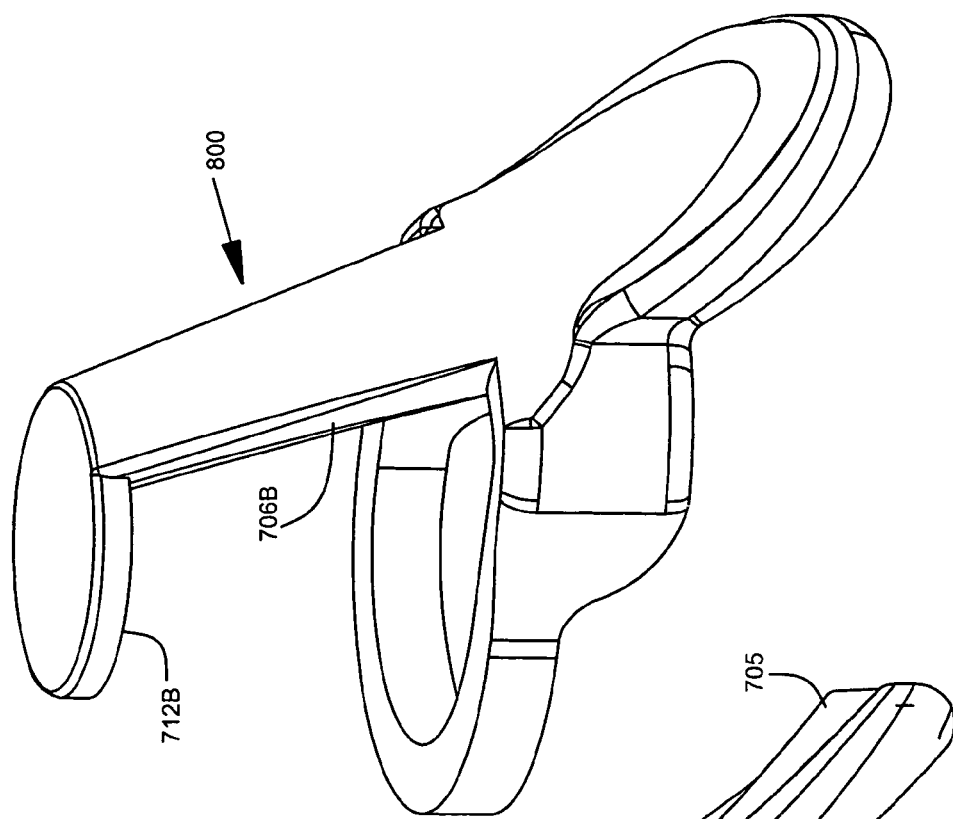
FIG. 30 is a perspective view of an embodiment of a cover adapter.
Figure 29:
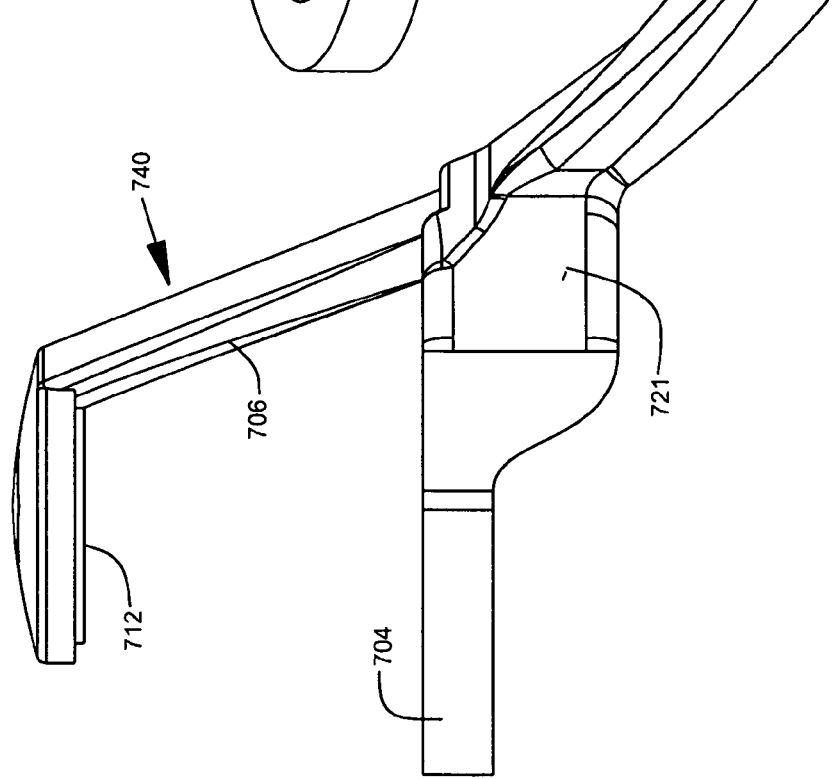
FIG. 29 is a detail side view of an embodiment of a cover adapter.

Referring to FIGS. 26A and 26B, cross-sectional and perspective view, respectively of cover adapter body 700 are shown. Cover adapter 700 comprises integrated elastomeric material. The joining method of the cover adapter may include two-shot co-injection, over-molding or adhesion. Rigid arm 703 distally terminates to cover member 701 that may be seated adjacent the access site in the natural state. Rigid arm 703 between and/or including the cover member 701 and proximal end 702 may contain elastomeric material, for example by overmolding of the cover adapter. Elastomeric covering surface 708 provides for contact with the access site. Material channel 709 provides for connecting the elastomeric covering surface with the flexible member 704. The elastomeric material may cover the proximal end 702 as well as provide gripping elements 705. Elements 707 may be provided in the rigid arm 703 to assist elastomeric material adhesion to the cover adapter. Referring now to FIG. 27, a cross-sectional view of cover adapter body 720 is shown. Retaining element 710 provides for securing elastomeric covering surface 708 to the cover member and may provide a gate location for injecting the elastomer material. Cover adapter body 730, comprising cover member 711 as an extension of the rigid arm 703 without elastomeric material, is shown in FIG. 28. Referring now to FIG. 29, cover adapter body 740 is shown. Cover adapter body 721 comprises rigid member 706 having separate elastomeric bodies; covering surface 712 and flexible member 704. Cover adapter body 721 may include gripping elements 705. Referring now to FIG. 30, cover adapter 800 is shown. Cover member 712B and rigid member 706B may be entirely elastomeric material. Flexibility and rigidity functionality of the adapter may be provided by including thin sections for flexibility and thick sections for rigidity.

Figure 32:
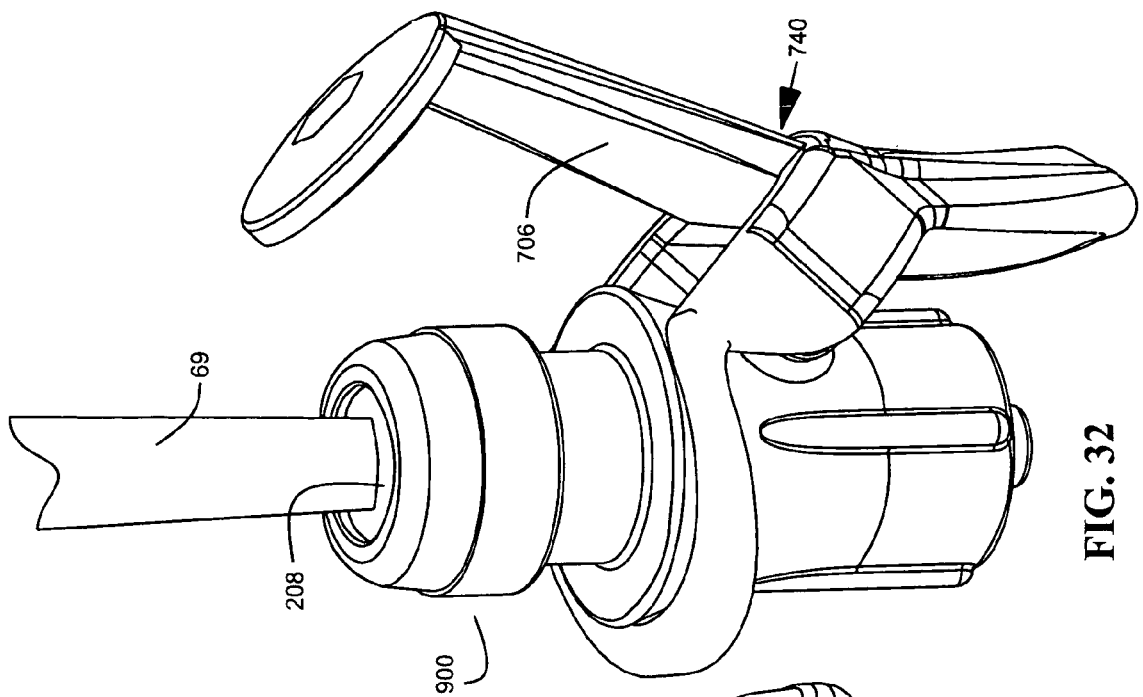
FIG. 32 is a perspective view of an embodiment of a fluid connector cover of FIG. 31 with an engaged external device.
Figure 31:
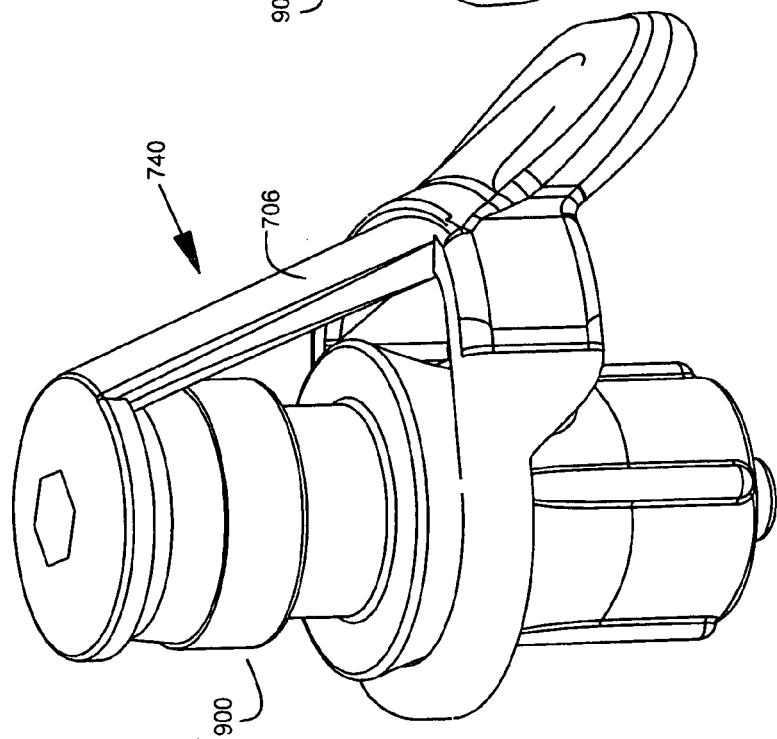
FIG. 31 is a perspective view of an embodiment of a fluid connector cover.
Figure 33B:
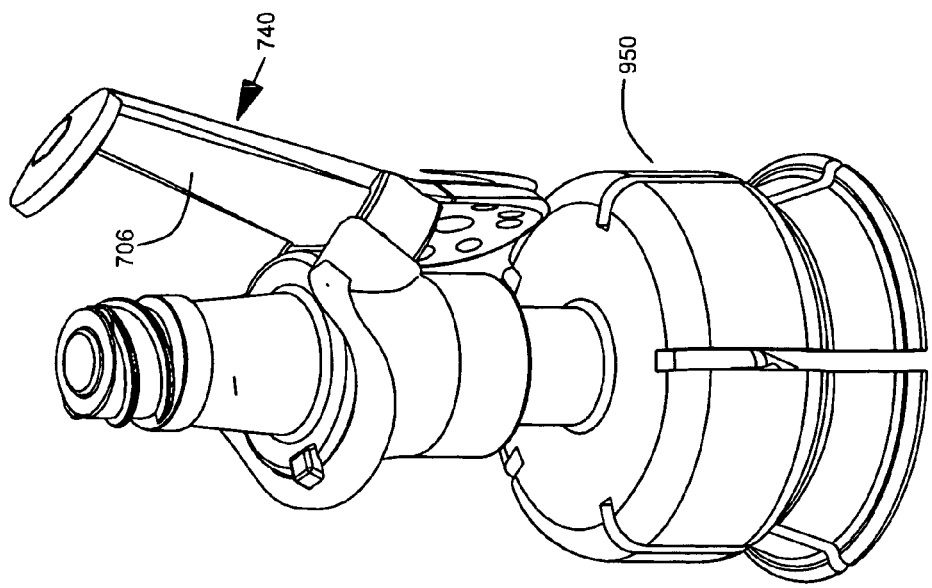
FIGS. 33A and 33B are perspective views of embodiments of a fluid connector cover with a vial adapter in an initial and activated state, respectively.
Figure 33A:
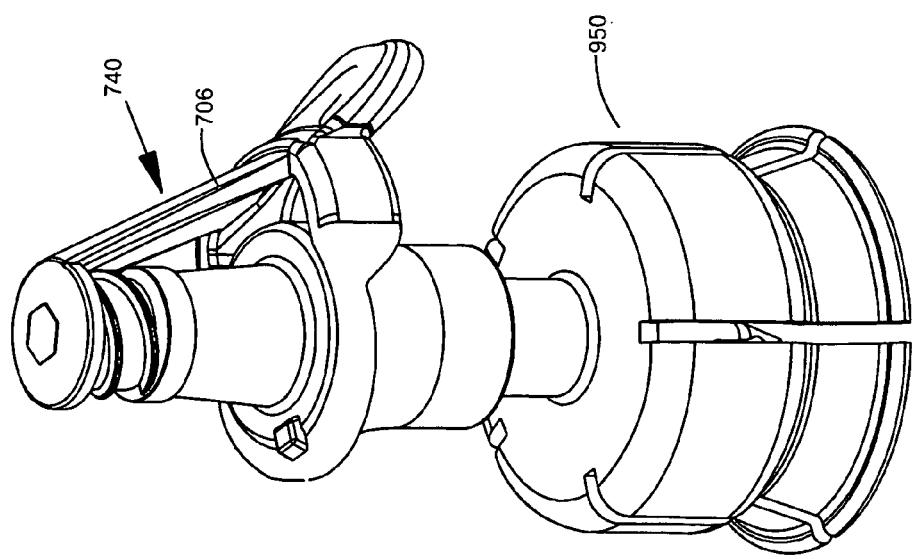

Referring now to FIGS. 31 and 32, cover adapter body 740 is shown in the initial passive state and an activated state. Penetrable septum type connector 900 is shown with attached cover adapter body 740. Penetrating member 69 is provided access to access site 208 when digital force (not shown) is applied to rigid arm 706. Referring now to FIGS. 33A and 33B, cover adapter 740 is shown in the initial passive state and an activated state, adapted to vial adapter 950.

Figure 34B:
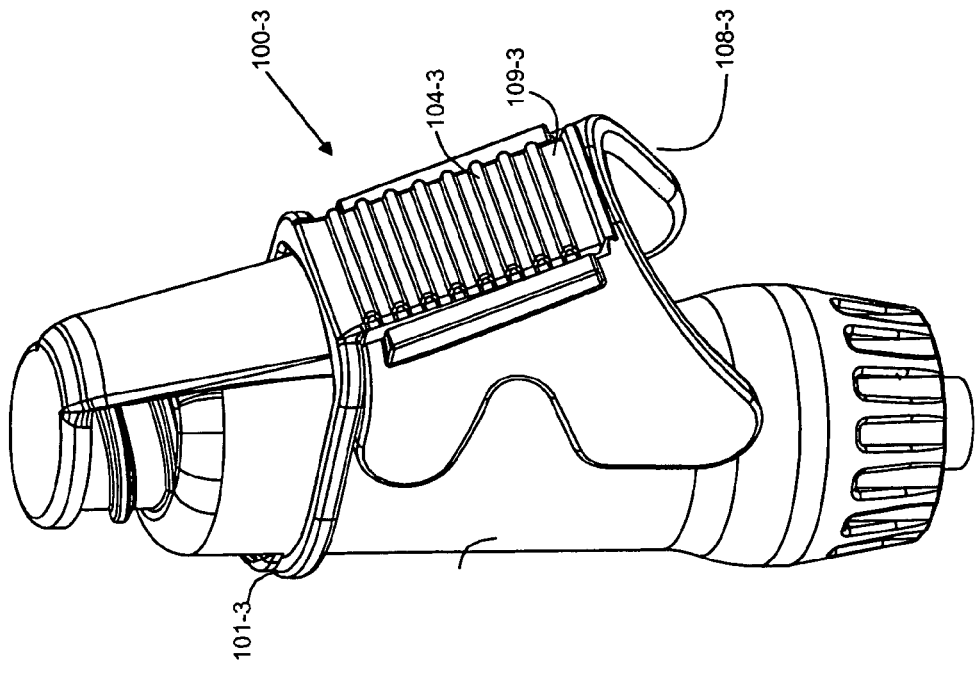
FIGS. 34A and 34B are a perspective view of a cover adapter embodiment and the cover adapter assembled with a connector housing.
Figure 34A:
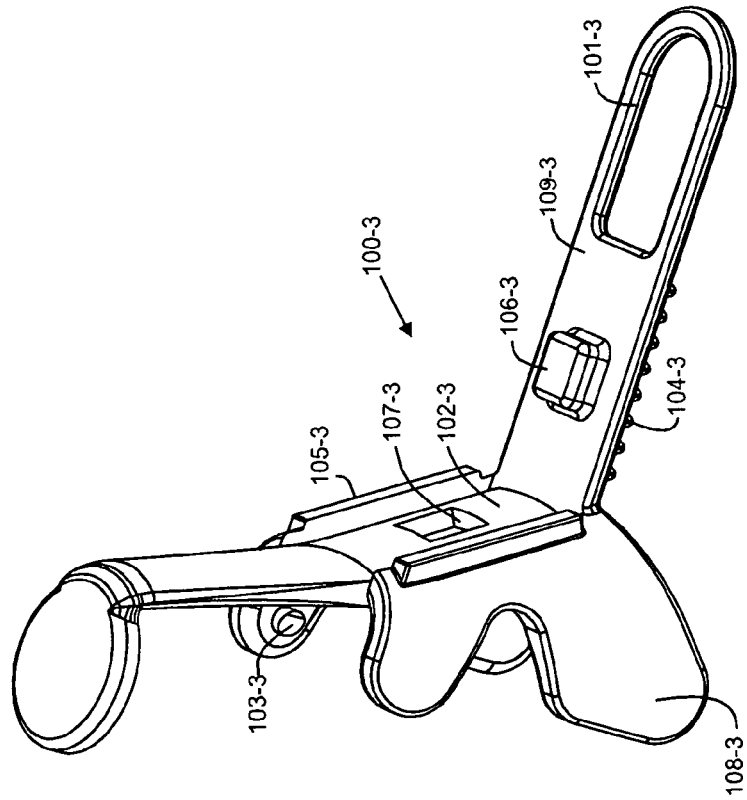

Referring now to FIGS. 34A-34B, fluid connector cover 100-3 has integrated elastomeric member 109-3 extends from the cover adapter body 102-3. Elastomeric member comprises a closed loop 101-3 with grip 104-3. Beveled pegs 103-3 fit into mating receptacles on a connector housing (not shown) to create a pivot point. Retention geometries 106-3, 107-3 integrated into the cover adapter body and elastomeric member to promote a secure attachment in the assembled state and include, but are not limited to, a mating boss and cutout as shown as a coupling means. FIG. 34B depicts assembled state, where elastomeric member 109-3 is engaged to the cover adapter body and the closed loop portion is looped over a fluid connector housing FIG. 34B.

A plurality of closed loops may be used to couple the cover adapter body to a fluid connector housing. This coupling provides both a preload to maintain an adequate seal at the fluid connector housing access site as well as a return force for the cover adapter body when an activation force has been removed. Grip 104-3 of cover adapter body facilitates activation. Protrusions 108-3 extend from the cover adapter body in a generally concave manner toward the fluid connector housing such that they clear the connector port during activation. Thus, when force is applied to grip 104-3, protrusions 108-3 move toward and partially around the fluid connector port as the cover is removed from the access site in an arc-like motion. The closed loop 101-3 couples the cover adapter body to the fluid connector housing such that the covering portion is held against the access site in its natural state. The closed loop also provides a return force to return the cover to its natural state. Raised features 105-3 retain the strap. The strap may also be comprised of a plurality of closed loops. Alternately, they may couple to a feature or set of features integrated with the connector housing rather than encircle it as shown in FIG. 34B. They may surround the fluid connector housing starting on one side of the cover adapter body and coupling to a feature or set of features on the other side of the cover adapter body.

Figure 35A:
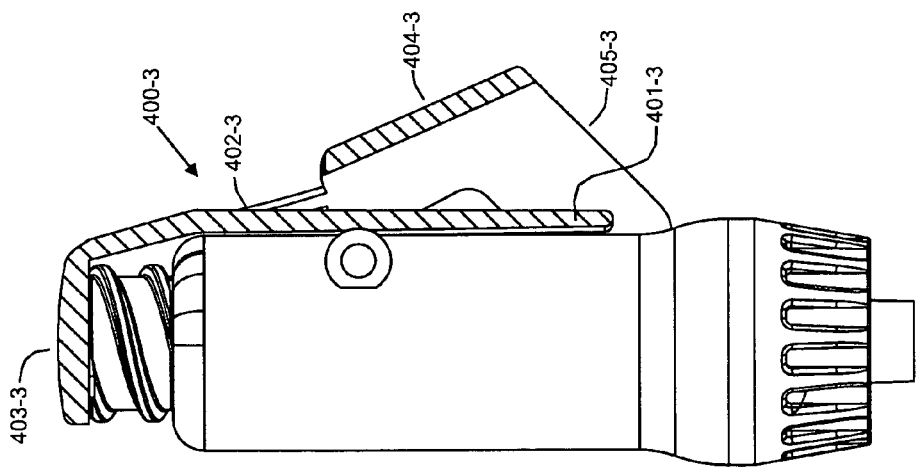
FIGS. 35-35A are section plane and cross-sectional views of a cover adapter embodiment assembled with a connector housing.
Figure 35:
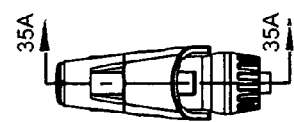

Referring now to FIGS. 35-35A, a cross-section of cover adapter body 400-3 in its natural state and assembled with a fluid connector housing by means of a pivoting interlock, is shown. This embodiment represents a cover adapter body in which a beam extends from the cover adapter body to provide preload for maintaining an adequate seal at the fluid connector housing access site as well as a return force for the cover adapter body when an activation force has been removed. The beam has a free end which contacts the fluid connector housing at a point along its length. Beam 401-3 extends from the neck 402-3 of the cover adapter body providing a preload force in the inactivated state to insure that the cover member 403-3 rests on the fluid connector housing access site. When force is applied at the finger pad portion 404-3, the beam deflects to provide a return force that allows the cover adapter to return to its natural state. Protrusions 405-3 extend in a concave-like direction from the finger pad portion of the cover adapter body clearing the fluid connector port upon activation.

Figure 36:
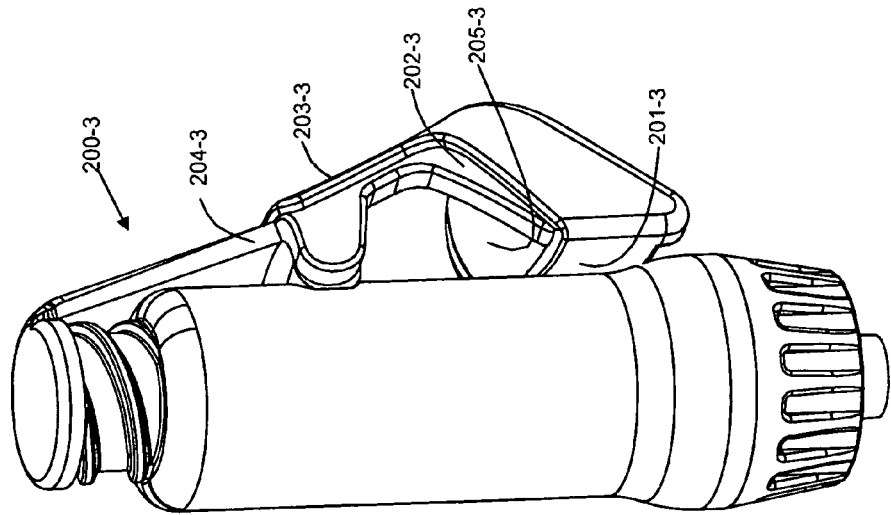
FIG. 36 is a perspective view of a cover adapter embodiment assembled with a connector housing.

Referring now to FIG. 36, cover adapter body 200-3 in its natural state and assembled with a fluid connector housing by means of a pivoting interlock is shown. This embodiment represents a cover adapter body with an integrated elastomeric portion. The elastomeric portion spans concave-like arm extensions from the cover adapter body proximal the finger pad portion. The span acts as a source of preload to maintain an adequate seal at the fluid connector housing access site as well as a return force for the cover adapter body when an activation force has been removed. A plurality of spans may be used to adjust for preload and return force. Elastomeric band 201-3 connects concave-like protrusions 202-3 proximal to finger pad 203-3 of the cover adapter body 204-3. When force is applied to the finger pad portion, the cover is removed from the connector housing access site in an arc-like motion as elastomeric band stores energy as it is elongated about connector port providing a return force that returns the cover adapter body to its natural state. Opening 205-3 provides adequate arc-like motion about connector port. Cover adapter 200-3 can be assembled from one side and in one step, resulting in an easier assembly process.

Referring now to FIGS. 37-38A, two views of an attachment means 1100-3 are shown. The depicted means for reduced separation of the cover adapter body from the fluid connector housing. Lugs 1101-3 integrated with the fluid connector housing mate with cutouts 1102-3 on the cover adapter body. A swaging, staking or similar process creates an interference 1103-3 that reduces detachment of the cover adapter body from the fluid connector housing. The pivot point geometries shown for rotational activation about the attachment means more securely couple the cover adapter body to the fluid connector housing include for example a ball and socket arrangement, a staking or swaging arrangement or a snap-fit arrangement.

Referring now to FIG. 39, cover adapter body 300-3 with anti-snag features in its natural state and assembled with a fluid connector housing by means of a pivoting interlock is shown. This embodiment represents a cover adapter body with an integrated elastomeric portion comprising a closed loop capable of encircling the fluid connector housing to provide preload. The preload provides an adequate seal at the fluid connector housing access site as well as a return force for the cover adapter body when an activation force has been removed. Concave-like protrusions from the cover adapter body act to reduce the possibility of the cover adapter body getting snagged as well as provide a structural backing for the elastomeric shroud that spans them. The shroud further reduces the possibility of the cover adapter body getting snagged. Protrusions 301-3 extend from the finger pad portion 302-3 of the cover adapter body 305-3 in a concave-like manner. Flexible shroud 303-3 extends between the protrusions and may be adhered to the cover adapter body. When the cover adapter body is activated at the finger pad portion, the shroud hinges at 304-3 so as not to prevent/hinder activation. Cover is removed from the fluid connector housing access site in an arc-like motion. Elastomeric band 307-3 provides a return force that allows the cover adapter body to return to its natural state. Gripping means 306-3 may be added at the finger pad. Embodiments that incorporate a finger pad may include concave protrusions as shown in FIG. 39 forming an anti-snagging shroud. The shroud may be fully integrated with the adapter body such that it may deform when the cover adapter body is activated or it may be partially integrated such that it is allowed to deform when the cover adapter body is activated.

Referring now to FIG. 40, an anti-snag modification 600-3 for a cover adapter body is shown. Deflection means 601-3 integrated into the fluid connector housing to reduce or eliminate the possibility of items snagging under the cover adapter body's finger pad portion 602-3. When force is applied at 602-3, the orientation and geometry of this deflector are such that it does not prevent/hinder activation.

Referring now to FIGS. 41-41A a locking means 1200-3 that may reduce the possibility of unintended activation of the cover adapter while in its initial position, is shown. At the pivot point interface of the cover adapter body and fluid connector housing, locking tab 1201-3 and mating locking receptacle 1202-3 allow rotation when they are clear of each other in a specific configuration. To allow activation, the user must push the cover adapter body up 1203-3 enough to free the locking tab from the locking receptacle. To return the cover adapter body to its initial position extrusion 1204-3, extending from the fluid connector housing, allows the elastomeric band to stretch when the user pushes along the vertical path.

Referring now to FIGS. 42-42A, cover adapter body securing means 1000-3 integrated with the fluid connector housing is shown. Lower extrusions 1001-3, 1002-3 retain the elastomeric member. These extrusions may also have geometry 1003-3 to partially surround the band on a third side.

Referring now to FIGS. 43-43A, cover member 800-3 comprising a thin elastomeric membrane 801-3 constrained at its extents is shown. The thin elastomeric membrane may be adhered in part or in whole about a perimeter of the cover member 802-3. Elastomeric cover extents are constrained and its interior is allowed to conform. The extents of the elastomer may adhere to the cover member in part or in whole.

Referring now to FIGS. 44A-B, views of cover member 700-3 comprising an elastomer 701-3 with free edges 703-3 is shown. The elastomer may be joined to the cover adapter body cover member 702-3. FIG. 44B represents an example where the elastomer freely conforms to the fluid connector housing access site. Referring now to FIGS. 44C-D, cover member 900-3 comprising elastomer extending from the cover adapter body cover member 904-3. The elastomer has an exterior portion 901-3 and interior portion 902-3 encircling pocket 903-3. FIG. 44D represents an elastomeric cover where an interior space is created by the elastomer. The elastomer has an interior and exterior portion and is adhered to the cover member of the cover adapter body. The empty space created may allow for any fluid expelled from the fluid connector housing to be trapped therein after activation to be in contact with an aseptically effective agent in the cover. FIGS. 45A-D illustrates several representations of cover adapter body and cover member geometries.

Referring now to FIG. 46, cover adapter body 500-3 is shown. Cover adapter body 500-3 may be assembled to a fluid connector housing by means of a pivoting interlock as described in the previous embodiments above. An elastomeric shroud 501-3 covers the open area under the finger pad portion 502-3 of the adapter body. Shroud portion 503-3 receives a mating fluid connector housing. When the cover is activated by force at finger pad portion 502-3, the shroud deforms so as not to prevent/hinder activation and the cover member is removed from the fluid connector housing access site in an arc-like motion as in the embodiments described above. Elastomeric band 504-3 provides a return force that allows the cover adapter to return to its natural state as in embodiment 300-3 in FIG. 39.

FIGS. 47-47A illustrate fluid connector cover 200-4 having removable lidding 206-4 with pull-tab 207-4 in the as-assembled and removed configuration respectively. Cover adapter body includes elastomeric seal 211-4 integrated with the access site covering means 208-4 of the cover member 203-4 of the cover adapter body. Elastomeric retention/return means 201-4, finger pad portion 202-4, cover member 203-4, anti-snag concave-like protrusions 204-4, rigid arm pivoting means 205-4 and removable lidding 206-4 are shown.

Figure 48:
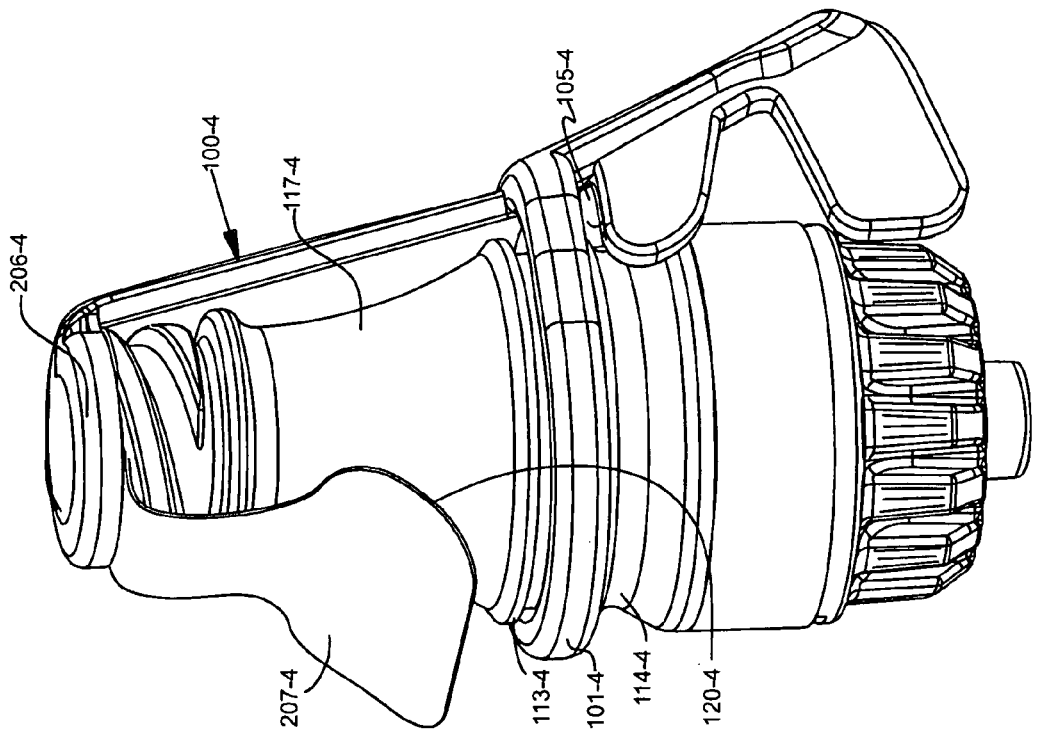
FIG. 48 is a perspective view of the cover adapter embodiment of FIG. 47 assembled to a connector housing.

FIG. 48 illustrates a perspective view of fluid connector cover 100-4 secured to a fluid connector housing 117-4; the cover shown in its closed, assembled state with removable lidding 206-4. Elastomeric return means 101-4 is pre-loaded to bias cover to the closed position. The fluid connector housing may comprise retention features 113-4, which may securably retain the elastomeric return means. Retention features 113-4 allow assembly of the cover adapter body to the fluid connector housing without particular radial alignment with respect to the central flow axis of the fluid connector housing. The fluid connector housing may comprise mating geometry 114-4 for mating with pivoting means 105-4 of the cover adapter body. The mating geometry 114-4 allows assembly of the cover adapter body to the fluid connector housing without particular radial alignment with respect to the central flow axis of the fluid connector housing. Any or all surfaces of the removable lidding may be coated or otherwise treated with disinfectant or antimicrobial agents. The cover may consist of any number of surface effects for sealing with the removable lidding. Surface effects may be, but are not limited to adhesives, texturing and/or ultrasonic welding features. The cover may be saturated wet or dry, rigid or elastomeric, absorbent or non-absorbant. The removable lidding may have a user-removable lidding tab 207-4 and may be sealably adhered to the cover portion to allow for the cover portion to remain saturated or impregnated for its shelf life while packaged prior to its use. Lidding tab may be doubled over on itself or similarly arranged such that when the user pulls the tab, it can be pealed away from the cover portion without needing to open the cover. The user-removable tab can also be affixed to the exterior of the fluid connector housing 120-4 so that user must pull the tab prior to opening the cover to access the underlying access site.

Figure 49:
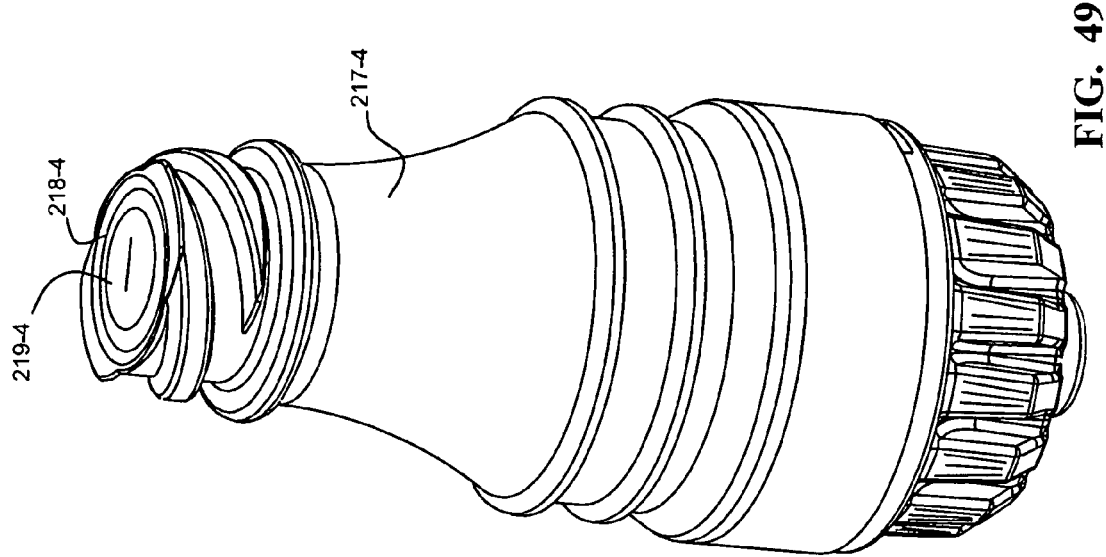
FIG. 49 is a perspective view of a connector housing embodiment.

FIG. 49 illustrates fluid connector housing 217-4 wherein an elastomeric seal 218-4 is positioned about the fluid connector housing's access site 219-4. The elastomeric seal seals the access site of the connector housing after removable lidding is removed and the cover adapter body is in its closed, assembled state. FIGS. 50-50A illustrate a sectional plane and cross-sectional view of fluid connector cover 300-4 comprises reservoir 305-4 filled with disinfectant solution and/or antimicrobial agents. The reservoir may be substantially secured to cover member 303-4, have one or more openings 304-4 to the interior of the reservoir and exiting in proximity to the cover member, and may be rigid or deformable. The covering means have a geometry which may mate with the geometry at the fluid connector housing access site. For example, the fluid connector housing having a concaved injection site surface is mated with a cover member that is convex and conforming. Other geometries may be used, for example, shapes that may or may not mate. The covering means may be, but is not limited to being elastomeric, plastic or absorbable or any combination thereof and may be loaded with aseptically effective agent. Openings in the cover may allow for the solution contained in the reservoir to be in fluid communication with the cover member element 303-4 that may be absorbent, as with hydrophilic foam or sponge-like material. FIGS. 51-51A illustrate sectional plane and cross-sectional view of fluid connector cover 400-4 which may have a cover member 403-4 comprising a reservoir 401-4 which may be filled with disinfectant solution and/or antimicrobial agents. The reservoir may be in direct communication with the cover member 404-4. A rigid reservoir in combination with a foam or sponge-like material may provide for absorption and "pumping" during opening and closing of the cover, allowing for fluid movement through the cover and to the access site. In a deformable reservoir in combination with a foam or sponge-like material, compression provides metering of the solution into the foam or sponge-like material.

Figures 52, 53:
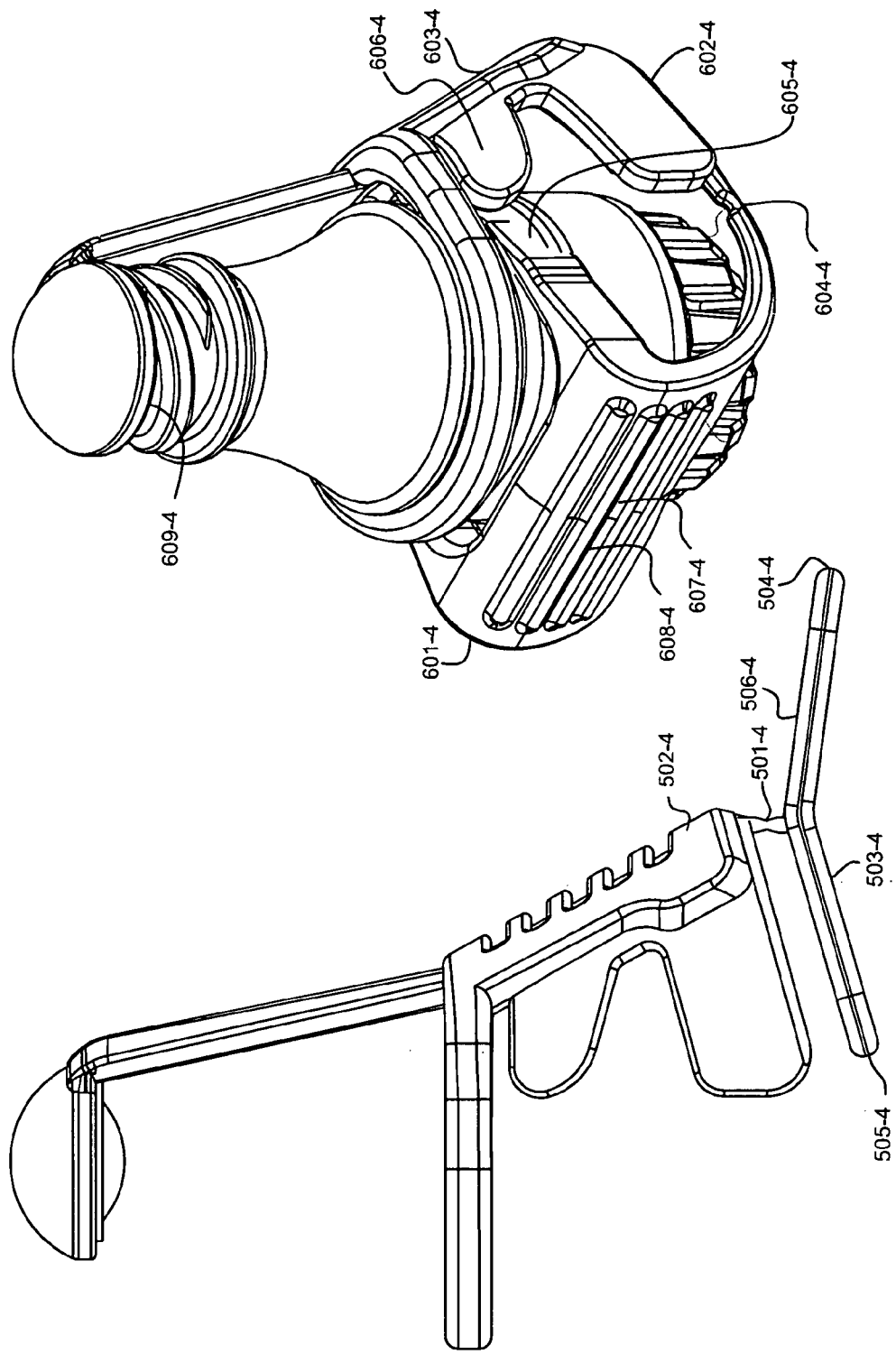
FIG. 52 is a profile view of a cover adapter locking mechanism embodiment.
FIG. 53 is a perspective view of a cover adapter locking mechanism embodiment.

FIG. 52 is a profile view of a locking mechanism which may integrate with any cover adapter body described herein. Hinge 501-4, which may be an elastomer, extends from the distal end of the finger pad portion 502-4, which couples to a locking means 503-4. Locking means comprise a first end 504-4 and a second end 505-4; the first end may have a pad portion 506-4 for moving the locking means about the hinge. The second end may couple with a fluid connector housing or a mating feature on a connector housing to prevent unintended movement of the cover adapter.

FIG. 53 is a perspective view of a wedge-style locking mechanism. Un-locking means 601-4 extends from lower portion 602-4 of finger pad portion 603-4. The un-locking means includes hinge 604-4, at least one wedge portion 605-4, which flexes a lock portion 606-4 when the un-locking means is pressed at gripping means 608-4 of finger pad 607-4. The lock portion may interact with a mating fluid connector housing such that the cover member 609-4 is not substantially moved away from the fluid connector housing access site when force is applied to the finger pad portion.

FIG. 54 illustrates a perspective view of a fluid connector cover 100-5; a fluid cover adapter embodiment comprising an elastomeric loading means 101-5, finger pad portion 102-5, cover member 103-5, anti-snag means 104-5, and a pivoting attachment means 105-5. The loading means may have a plurality of members such that when the finger pad portion is pressed, energy may be stored in the elastomeric return means which may then be used to return the cover adapter to its closed, assembled state.

The cover member comprises seal portion 106-5. The sealing portion has outer portion 107-5 and inner portion 108-5. The seal portion seals the access site of a fluid connector housing when the cover adapter body is in its closed, assembled state. The cover member may be saturated wet or dry, rigid or elastomeric, absorbent or non-absorbent. The cover member may have geometry that mates with corresponding geometry at the fluid connector housing access site. As shown, the fluid connector housing has a concave access site surface and the corresponding cover portion is convex and conforming. Alternately, these can be of various shapes that may or may not mate. The covering means may include a shroud 113-5 extending from the cover member 103-5.

Figure 56:
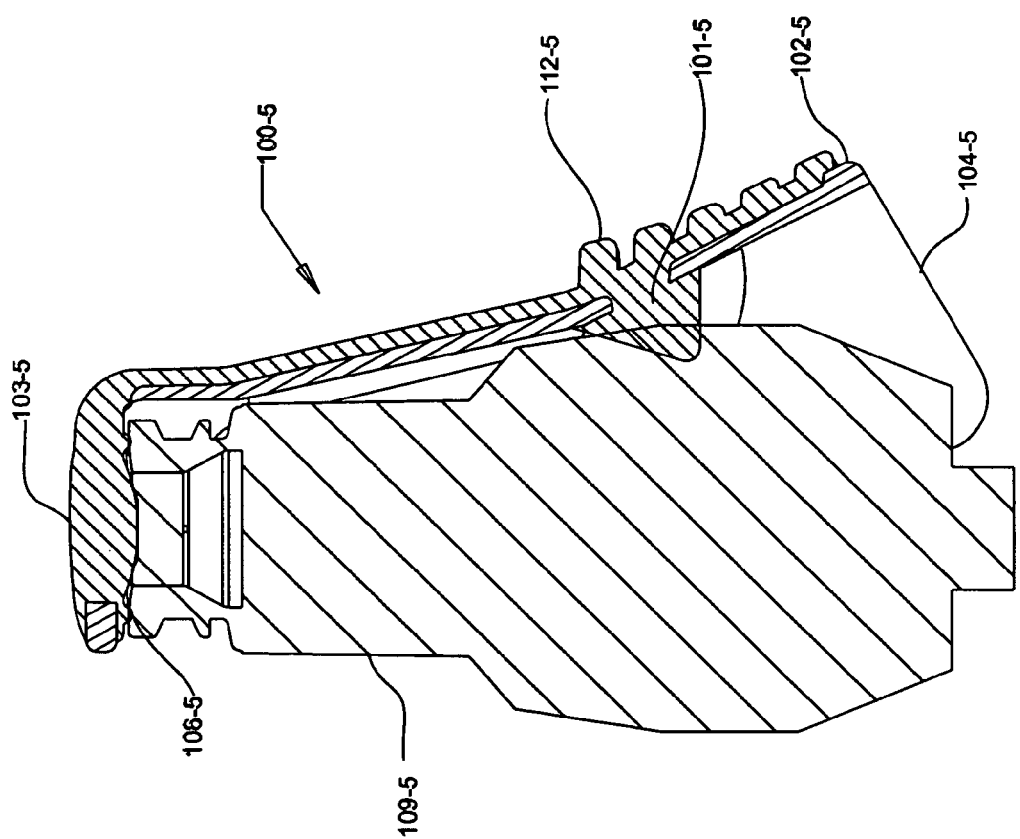
FIG. 56 is a cross-sectional view of a first embodiment cover adapter secured to a connector housing in a closed, assembled state.

FIG. 55 illustrates a perspective view of fluid connector cover 100-5 secured to a fluid connector housing 109-5, the cover shown in its closed, assembled state. The elastomeric loading means (not shown) may be pre-loaded in this state to bias the cover portion to the closed position. The fluid connector housing comprises mating geometry 110-5 for mating with corresponding pivoting means 111-5 on the cover adapter body; the finger pad with gripping means 112-5 for ergonomic control is integrated with the loading means. FIG. 56 illustrates a cross-sectional view of fluid connector cover 100-5 of FIG. 55, secured to fluid connector housing 109-5; the cover member shown in its closed, assembled state. Cover adapter body comprise an elastomeric loading means 101-5, finger pad portion 102-5, cover member 103-5, anti-snag means 104-5 and an elastomeric seal portion 106-5.

Figures 57, 57A:
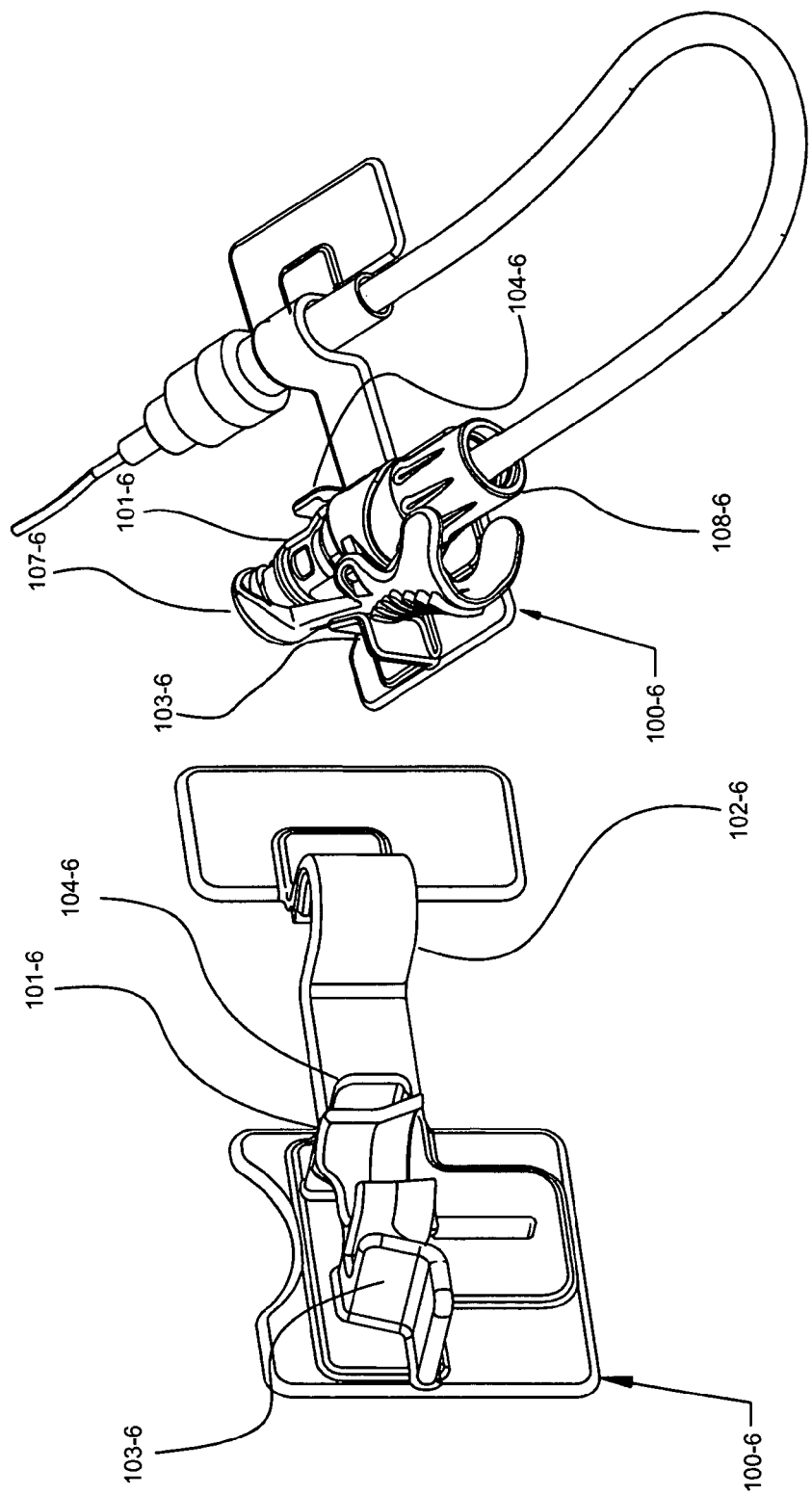
FIGS. 57 and 57A are perspective views of a securement device embodiment and with a fluid connector housing with integrated cover adapter in a locked closed position, respectively.
Figures 58, 59:
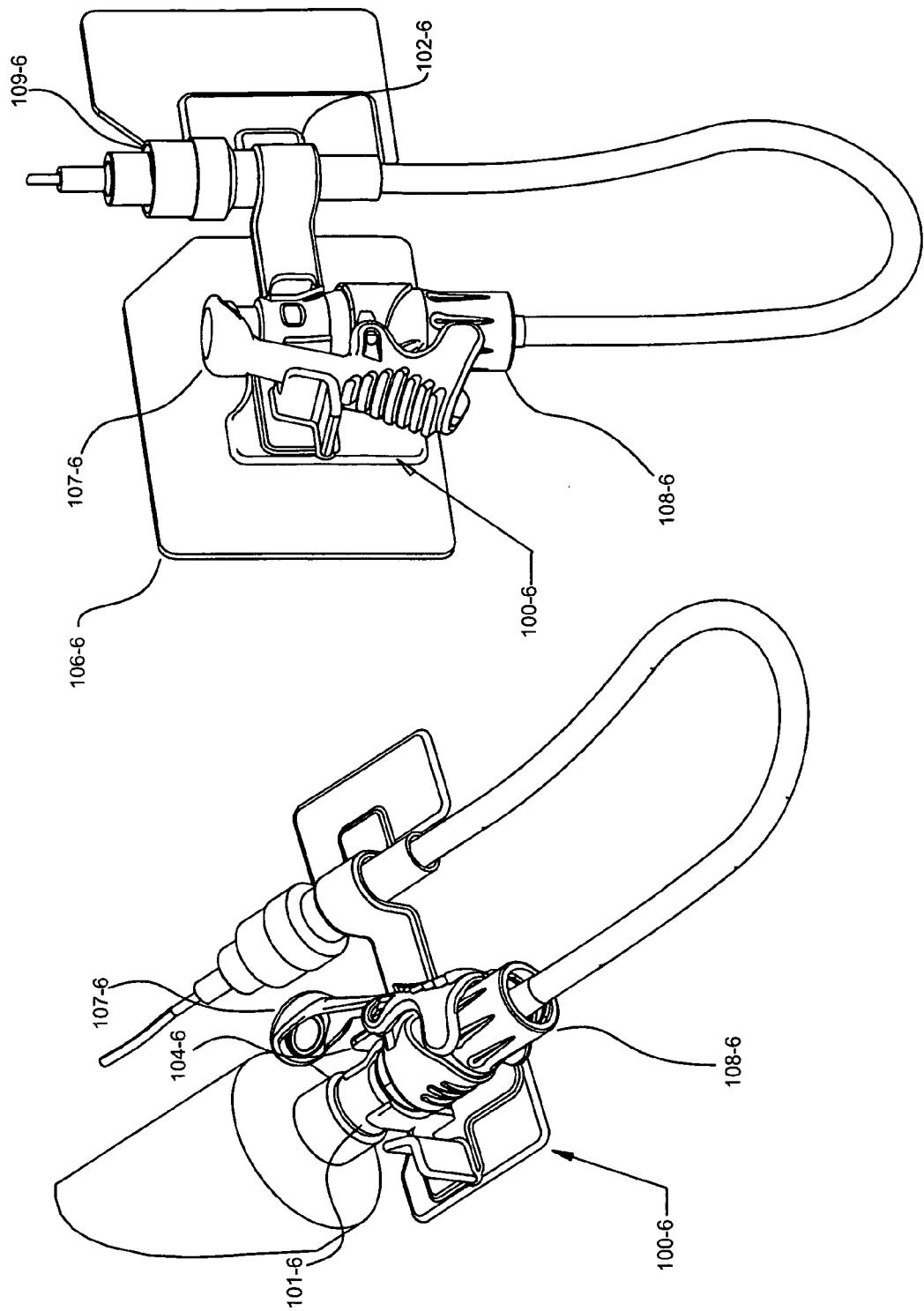
FIG. 58 is a perspective view of a securement device and fluid connector housing with cover adapter combination shown with the cover adapter in an open position.
FIG. 59 is a perspective view of a securement device and fluid connector housing with cover adapter connected to an IV extension set and an adhesive strip.

FIG. 57 illustrates a perspective view of securement device 100-6 for a fluid connector housing with fluid connector cover and IV extension set. Securement device comprises first retention means 101-6 adapted for a fluid connector cover and fluid connector housing as well as second retention means 102-6 adapted for an IV set male luer or catheter hub on the fluid connector cover; first locking means 103-6 adapted for locking the fluid connector cover closed; and second locking means 104-6 adapted for locking the fluid connector cover open. FIG. 57A illustrates a perspective view of securement device 100-6 adapted for fluid connector housing 108-6 with fluid connector cover 107-6 in the locked closed position. The securement device may have a plurality of members such that when the fluid connector housing 108-6 with fluid connector cover 107-6 is engaged with the securement device first retention means 101-6, the fluid connector housing with fluid connector cover 107-6 is securely held. Retention features 101-6 comprise multiple securement positions including but not limited to, first locking means 103-6 that constrain the fluid connector cover 107-6 in a closed position. Likewise, FIG. 58 illustrates a perspective view of securement device 100-6 adapted for fluid connector housing with fluid connector cover 107-6 in the open position. The securement device may have a plurality of members such that when the fluid connector housing 108-6 with fluid connector cover 107-6 is inserted into the securement device retention features 101-6, the fluid connector housing with integrated cover adapter body 107-6 is securely held. Retention features 101-6 comprise multiple securement positions including but not limited to, second locking means 104-6 that constrain the cover adapter 107-6 in an open position.

FIG. 59 illustrates a perspective view of securement device 100-6 adapted for fluid connector housing 108-6 with fluid connector cover 107-6 including IV extension set 109-6 and an adhesive strip 106-6. The securement device may have a plurality of members such that when an IV extension set 109-6 is engaged with the IV extension set retention features 102-6 on the securement device, the IV extension set 109-6 is held securely reducing and/or eliminating pistoning. The securement device may have a plurality of adhesive strips 106-6 in any configuration that affix the securement device to a subject.

The fluid connector cover, fluid connector housing and/or securement device may be provided separately or in combination in a sterile package. The fluid connector cover described above will normally be supplied in assembled form or as a kit, and may be provided sterile. The term "fluid connector cover kit" as used herein is intended to include within its scope the fluid connector cover or cover adapter thereof in partially or fully disassembled form. The fluid connector cover or kit may contain a fluid connector and a separate fluid connector cover assemblage for user-assembly. The fluid connector cover may be secured to or permanently affixed to the fluid connector.

The fluid connector cover described herein is not limited to use with I.V. products, Y-connectors, male/female biers and the like. Touch contamination is an issue with many connection applications. A protective cover, particularly a passive fluid connector cover as herein described, may prevent or eliminate microbial growth and may also minimize particulate and other foreign material from being flushed or otherwise introduced through a fluid connection. Adaptations of the designs could be made to fit the parts to virtually any connection cover adapter.

Any and all of the components of the fluid connector cover may be injection molded, compression molded and/or transfer molded. Formed parts may further be overmolded with elastomeric material. Tooling of simple open/close design may be used. Integration of the fluid connector cover with the connector housing may provide a method to incorporate a cover without increasing the number of components, which may reduce assembly cost. Modification of existing female connector housings to provide for fluid connector covers as herein described may utilize tooling of the same orientation as for molding the existing housing. This may minimize cost in modifying current housings for adaptation of the fluid connector cover.

In this specification and the appended claims, the singular forms "a," "an," and "the" include plural reference unless the context clearly dictates otherwise.

As used herein, "comprising" and grammatical equivalents thereof are inclusive or open-ended terms that do not exclude additional, un-recited elements or method steps. "Comprising" is to be interpreted as including the more restrictive terms "consisting of and "consisting essentially of" As used herein, "consisting of and grammatical equivalents thereof exclude any element, step, or ingredient not specified in the claim. As used herein, "consisting essentially of and grammatical equivalents thereof limit the scope of a claim to the specified materials or steps and those that do not materially affect the basic and novel characteristic or characteristics of the claimed invention.

While the invention has been described in detail and with reference to specific embodiments thereof, it will be apparent to one skilled in the art that various changes and modifications may be made without departing from the spirit and scope of the invention.

What is claimed is:

1. A fluid connector comprising
a housing having an access site;
a rigid arm rotatably and piviotably attached to the housing such that the rigid arm is freely rotatable relative to the housing, the rigid arm having a proximal end and a distal end, the distal end terminating in a cover member, the cover member comprising an aseptically effective agent;
the cover member integral with the distal end of the rigid arm, the cover member reversibly displaceable from an initial position in closed engagement with and covering the access site to a second position uncovering the access site upon displacement of the proximal end of the rigid arm; and
an elastomeric member in positioned entirely between the proximal end and the distal end of the rigid arm and the housing, the elastomeric member in a deformed state providing a bias to the rigid arm;
wherein displacement of the proximal end of the rigid arm:
(i) further deforms the elastomeric member between the rigid arm and the housing; and
(ii) transitions the cover member to the second position;
wherein the further deformed elastomeric member is configured to transition the cover member from the second position back to the initial position.

2. The fluid connector of claim 1, wherein the elastomeric member is integral with the rigid arm.

3. A fluid connector comprising
a housing comprising at least one fluid access site to access an interior of the housing;
a rigid arm having a proximal end and a distal end terminating in a cover member, the rigid arm rotatably attached to the housing with at least one attachment member, positioned between the proximal end and the distal end of the rigid arm that define an axis of rotation such that the rigid arm is freely rotatable about the axis of rotation relative to the housing; and
an elastomeric member positioned between the rigid arm and the housing, and between the distal end and the proximal end of the rigid arm to apply a force on the rigid arm to a side of the axis of rotation opposite that of the cover member, the force biasing the cover member into an initial configuration where the cover is in closed engagement with and covers the at least one fluid access site;
wherein displacement of the proximal end of the rigid arm pivots the rigid arm and moves the cover member from the initial configuration to a disengaged, open configuration with respect to the at least one fluid access site, and deforms the elastomeric member between the rigid arm and the housing wherein deformation of the elastomeric member increases the force on the arm to the side of the axis of rotation opposite that of the cover member for returning the cover member to its initial configuration.

4. The fluid container of claim 3, wherein the cover member comprises an aseptically effective agent.

5. The fluid connector of claim 3, wherein the compressible elastomeric member is applies the force on the rigid arm only to a side of the axis of rotation opposite that of the cover member.

6. The fluid connector of claim 3, wherein the flexible member is an elastomeric loop attached to the fluid connector.

7. The fluid connector of claim 3 wherein the cover member further comprises a reservoir.

8. The fluid connector of claim 7 wherein the reservoir is a foam or sponge.

9. The fluid connector of claim 3, wherein the housing further comprises an elastomeric seal proximal to the access site of the housing.

10. The fluid connector of claim 3, wherein the cover member further comprises an elastomeric seal.

11. The fluid connector of claim 3, further comprising a locking mechanism.

12. The fluid connector of claim 3, further comprising anti-snagging means.

13. A fluid connector comprising:
a housing having a generally cylindrical shape, the housing comprising an access site to access an interior of the housing;
a rigid arm having a proximal end and a distal end terminating to a cover member, the rigid arm extending the length of the housing and pivotally coupled to the housing, the cover member providing an aseptically effective agent to the access site;
elastomeric material integral with the rigid arm and deformed between the rigid arm and the housing providing a bias to the rigid arm
and where cover member is in closed engagement with the access site;
wherein applying a force to the proximal end of the rigid arm transitions the cover member from the closed engagement relationship to an uncovered relationship, and releasing the force from the proximal end of the rigid arm transitions the cover member from the uncovered configuration to the closed engagement configuration.

14. The fluid connector of claim 1, wherein the elastomeric material is configured to circumvent around the perimeter of the housing.

15. The fluid connector of claim 13, wherein the elastomeric material is configured to be further deformed in response to a user engagement with the proximal end of the rigid arm increasing the force applied to the rigid arm.

16. The fluid connector of claim 3, wherein
the housing is selected from filled or unfilled thermoplastic or engineering thermoplastic, polybutylene terephthalate (PBT), cyclic olefinic copolymers (COC's), thermoplastic polyurethanes (TPU), rigid polyvinyl chloride (PVC), and polycarbonate (PC);
wherein the compressible elastomeric member is selected from reaction-injection molded RIM elastomers, silicones, elastomeric polyurethanes, thermoplastic elastomers, synthetic polyisoprenes and rubber.

* * * * *